(12) United States Patent
Kjellman et al.

(10) Patent No.: US 11,524,057 B2
(45) Date of Patent: *Dec. 13, 2022

(54) CYSTEINE PROTEASE

(71) Applicant: HANSA BIOPHARMA AB, Lund (SE)

(72) Inventors: Christian Kjellman, Lund (SE); Sofia Jarnum, Lund (SE); Emma Nordahl, Lund (SE)

(73) Assignee: HANSA BIOPHARMA AB

( * ) Notice: Subject to any disclaimer, the term of this patent is extended or adjusted under 35 U.S.C. 154(b) by 0 days.

This patent is subject to a terminal disclaimer.

(21) Appl. No.: 16/792,747

(22) Filed: Feb. 17, 2020

(65) Prior Publication Data

US 2020/0179497 A1 Jun. 11, 2020

Related U.S. Application Data

(63) Continuation of application No. 15/550,318, filed as application No. PCT/EP2016/053054 on Feb. 12, 2016, now Pat. No. 10,758,597.

(30) Foreign Application Priority Data

Feb. 12, 2015 (GB) .................................. 1502305

(51) Int. Cl.
*A61K 38/48* (2006.01)
*C12N 9/64* (2006.01)
*C12N 9/24* (2006.01)
*A61K 38/00* (2006.01)

(52) U.S. Cl.
CPC ............... *A61K 38/48* (2013.01); *C12N 9/24* (2013.01); *C12N 9/6472* (2013.01); *C12N 9/6475* (2013.01); *C12Y 304/2201* (2013.01); *A61K 38/00* (2013.01); *Y02A 50/30* (2018.01)

(58) Field of Classification Search
CPC .............................. C12N 9/641; C12N 9/6472
USPC .................................................. 435/220, 192
See application file for complete search history.

(56) References Cited

FOREIGN PATENT DOCUMENTS

| WO | 02/50107 | | 6/2002 | | |
|---|---|---|---|---|---|
| WO | 03/051914 | A2 | 6/2003 | | |
| WO | 2006/131347 | A2 | 12/2006 | | |
| WO | 2009/033670 | A2 | 3/2009 | | |
| WO | 2009/075646 | A1 | 6/2009 | | |
| WO | WO-2009075646 | A1 * | 6/2009 | ........... | C07K 14/315 |
| WO | 2009/080278 | A1 | 7/2009 | | |
| WO | 2010/089126 | A2 | 8/2010 | | |
| WO | 2011/149419 | A1 | 12/2011 | | |
| WO | 2013/037824 | A1 | 3/2013 | | |
| WO | 2015/040125 | A1 | 3/2015 | | |
| WO | 2016/012285 | A2 | 1/2016 | | |
| WO | 2016/0128558 | A1 | 8/2016 | | |
| WO | WO-2020016318 | A1 * | 1/2020 | ............... | C12N 9/58 |

OTHER PUBLICATIONS

UniProt database Acc#U2TXC9 Durkin et al, 2013. Alignment with SID17.*
A_Geneseq database Acc#AWW90991, SID11 from Flock et al, WO-2009075646. Alignment with SID4.*
Agniswamy et al., "Crystal Structure of group A *Streptococcus* MAC-1 orthorhombic form" Feb. 28, 2006, Database PDBe accession No. 2aul.
Akesson et al., "IdeS, a Highly Specific Immunoglobulin G (IgG)-Cleaving Enzyme from *Streptococcus pyogenes*, Is Inhibited by Specific IgG Antibodies Generated during Infection" (2006) Infect. Immun. 74:497-503.
IgG-degrading enzyme/Mac-1 IdeZ [*Streptococcus equi*]. NCBI Reference Sequence: WP_014622780.1 Link: https://www.ncbi.nlm.nih.gov/protein/WP_014622780.1?report=genbank&log$=protalign&blast_rank=3&RID=XEYFHFB3015#feature_WP_014622780.1.
Nandakumar et al., "Therapeutic cleavage of IgG: new avenues for treating inflammation" Trends in Immunology 29(4):173-178, Mar. 6, 2008.
NCBI database Acc#WP 014622780, 2013. Alignment with SID 4.
Persson et al., "Proteolytic processing of the streptococcal IgG endopeptidase IdeS modulates the functional properties of the enzyme and results in reduced immunorecognition" Mol Immunol. (2015) 68(2):176-184.
Uni Prot_201902 database Acc#COMGK6 Holden et al, 2009. Alignment with SID14.
Wenig et al., "Structure of the streptococcal endopeptidase IdeS, a cysteine proteinase with strict specificity for IgG" (2004) Proc. Natl. Acad. Sci. USA. 101:17371-17376.
FEMS Microbiol Lett, 2006, vol. 262, p. 230-235.
Lannergard et al., "*Streptococcus equi* subsp. *zooepidemicus* IgG endopeptidase (ideZ) gene, complete cds", GenBank [online], Aug. 22, 2006, Database Accession No. DQ826037, [retrieved on Feb. 21, 2020], https://vww.ncbi.nlm.nih.gov/nuccore/DQ826037.
Hypothetical protein [*Streptococcus pyogenes*]', NCBI Reference Sequence [online], May 15, 2013, Database Accession No. WP_010922160, [retrieved on Feb. 21, 2020], https://ncbi.nlm.nih.gov/protein/WP_010922160.1.
Japanese Office Action dated Feb. 25, 2020 cited during the prosecution of related Japanese Application No. 2017-542900.

* cited by examiner

*Primary Examiner* — Sheridan Swope
(74) *Attorney, Agent, or Firm* — Norton Rose Fulbright US LLP

(57) ABSTRACT

The present invention relates to a novel polypeptide which displays IgG cysteine protease activity, and in vivo and ex vivo uses thereof. Uses of the polypeptide include methods for the prevention or treatment of diseases and conditions mediated by IgG, and methods for the analysis of IgG.

9 Claims, 14 Drawing Sheets

Specification includes a Sequence Listing.

SEQUENCE LISTING

<160> NUMBER OF SEQ ID NOS: 55

<210> SEQ ID NO 1
<211> LENGTH: 339
<212> TYPE: PRT
<213> ORGANISM: Streptococcus pyogenes

<400> SEQUENCE: 1

```
Met Arg Lys Arg Cys Tyr Ser Thr Ser Ala Ala Val Leu Ala Ala Val
1               5                   10                  15

Thr Leu Phe Val Leu Ser Val Asp Arg Gly Val Ile Ala Asp Ser Phe
            20                  25                  30

Ser Ala Asn Gln Glu Ile Arg Tyr Ser Glu Val Thr Pro Tyr His Val
        35                  40                  45

Thr Ser Val Trp Thr Lys Gly Val Thr Pro Ala Asn Phe Thr Gln
    50                  55                  60

Gly Glu Asp Val Phe His Ala Pro Tyr Val Ala Asn Gln Gly Trp Tyr
65                  70                  75                  80

Asp Ile Thr Lys Thr Phe Asn Gly Lys Asp Asp Leu Leu Cys Gly Ala
                85                  90                  95

Ala Thr Ala Gly Asn Met Leu His Trp Trp Phe Asp Gln Asn Lys Asp
            100                 105                 110

Gln Ile Lys Arg Tyr Leu Glu His Pro Glu Lys Gln Lys Ile Asn
        115                 120                 125

Phe Asn Gly Glu Gln Met Phe Asp Val Lys Glu Ala Ile Asp Thr Lys
130                 135                 140

Asn His Gln Leu Asp Ser Lys Leu Phe Glu Tyr Phe Lys Glu Lys Ala
145                 150                 155                 160

Phe Pro Tyr Leu Ser Thr Lys His Leu Gly Val Phe Pro Asp His Val
                165                 170                 175

Ile Asp Met Phe Ile Asn Gly Tyr Arg Leu Ser Leu Thr Asn His Gly
            180                 185                 190

Pro Thr Pro Val Lys Glu Gly Ser Lys Asp Pro Arg Gly Gly Ile Phe
        195                 200                 205

Asp Ala Val Phe Thr Arg Gly Asp Gln Ser Lys Leu Leu Thr Ser Arg
210                 215                 220

His Asp Phe Lys Glu Lys Asn Leu Lys Glu Ile Ser Asp Leu Ile Lys
225                 230                 235                 240

Lys Glu Leu Thr Glu Gly Lys Ala Leu Gly Leu Ser His Thr Tyr Ala
                245                 250                 255

Asn Val Arg Ile Asn His Val Ile Asn Leu Trp Gly Ala Asp Phe Asp
            260                 265                 270

Ser Asn Gly Asn Leu Lys Ala Ile Tyr Val Thr Asp Ser Asp Ser Asn
        275                 280                 285

Ala Ser Ile Gly Met Lys Lys Tyr Phe Val Gly Val Asn Ser Ala Gly
    290                 295                 300

Lys Val Ala Ile Ser Ala Lys Glu Ile Lys Glu Asp Asn Ile Gly Ala
305                 310                 315                 320

Gln Val Leu Gly Leu Phe Thr Leu Ser Thr Gly Gln Asp Ser Trp Asn
                325                 330                 335

Gln Thr Asn
```

<210> SEQ ID NO 2
<211> LENGTH: 310
<212> TYPE: PRT

<213> ORGANISM: Streptococcus pyogenes

<400> SEQUENCE: 2

Asp Ser Phe Ser Ala Asn Gln Glu Ile Arg Tyr Ser Glu Val Thr Pro
1               5                   10                  15

Tyr His Val Thr Ser Val Trp Thr Lys Gly Val Thr Pro Pro Ala Asn
            20                  25                  30

Phe Thr Gln Gly Glu Asp Val Phe His Ala Pro Tyr Val Ala Asn Gln
        35                  40                  45

Gly Trp Tyr Asp Ile Thr Lys Thr Phe Asn Gly Lys Asp Asp Leu Leu
    50                  55                  60

Cys Gly Ala Ala Thr Ala Gly Asn Met Leu His Trp Trp Phe Asp Gln
65                  70                  75                  80

Asn Lys Asp Gln Ile Lys Arg Tyr Leu Glu Glu His Pro Glu Lys Gln
                85                  90                  95

Lys Ile Asn Phe Asn Gly Glu Gln Met Phe Asp Val Lys Glu Ala Ile
            100                 105                 110

Asp Thr Lys Asn His Gln Leu Asp Ser Lys Leu Phe Glu Tyr Phe Lys
        115                 120                 125

Glu Lys Ala Phe Pro Tyr Leu Ser Thr Lys His Leu Gly Val Phe Pro
    130                 135                 140

Asp His Val Ile Asp Met Phe Ile Asn Gly Tyr Arg Leu Ser Leu Thr
145                 150                 155                 160

Asn His Gly Pro Thr Pro Val Lys Glu Gly Ser Lys Asp Pro Arg Gly
                165                 170                 175

Gly Ile Phe Asp Ala Val Phe Thr Arg Gly Asp Gln Ser Lys Leu Leu
            180                 185                 190

Thr Ser Arg His Asp Phe Lys Glu Lys Asn Leu Lys Glu Ile Ser Asp
        195                 200                 205

Leu Ile Lys Lys Glu Leu Thr Glu Gly Lys Ala Leu Gly Leu Ser His
    210                 215                 220

Thr Tyr Ala Asn Val Arg Ile Asn His Val Ile Asn Leu Trp Gly Ala
225                 230                 235                 240

Asp Phe Asp Ser Asn Gly Asn Leu Lys Ala Ile Tyr Val Thr Asp Ser
                245                 250                 255

Asp Ser Asn Ala Ser Ile Gly Met Lys Lys Tyr Phe Val Gly Val Asn
            260                 265                 270

Ser Ala Gly Lys Val Ala Ile Ser Ala Lys Glu Ile Lys Glu Asp Asn
        275                 280                 285

Ile Gly Ala Gln Val Leu Gly Leu Phe Thr Leu Ser Thr Gly Gln Asp
    290                 295                 300

Ser Trp Asn Gln Thr Asn
305                 310

<210> SEQ ID NO 3
<211> LENGTH: 349
<212> TYPE: PRT
<213> ORGANISM: Streptococcus pyogenes

<400> SEQUENCE: 3

Met Lys Thr Ile Ala Tyr Pro Asn Lys Pro His Ser Leu Ser Ala Gly
1               5                   10                  15

Leu Leu Thr Ala Ile Ala Ile Phe Ser Leu Ala Ser Ser Asn Ile Thr
            20                  25                  30

Tyr Ala Asp Asp Tyr Gln Arg Asn Ala Thr Glu Ala Tyr Ala Lys Glu

```
                35                  40                  45
        Val Pro His Gln Ile Thr Ser Val Trp Thr Lys Gly Val Thr Pro Leu
         50                  55                  60

Thr Pro Glu Gln Phe Arg Tyr Asn Asn Glu Asp Val Ile His Ala Pro
         65                  70                  75                  80

Tyr Leu Ala His Gln Gly Trp Tyr Asp Ile Thr Lys Ala Phe Asp Gly
                         85                  90                  95

Lys Asp Asn Leu Leu Cys Gly Ala Ala Thr Ala Gly Asn Met Leu His
                        100                 105                 110

Trp Trp Phe Asp Gln Asn Lys Thr Glu Ile Glu Ala Tyr Leu Ser Lys
                    115                 120                 125

His Pro Glu Lys Gln Lys Ile Ile Phe Asn Asn Gln Glu Leu Phe Asp
                    130                 135                 140

Leu Lys Ala Ala Ile Asp Thr Lys Asp Ser Gln Thr Asn Ser Gln Leu
        145                 150                 155                 160

Phe Asn Tyr Phe Arg Asp Lys Ala Phe Pro Asn Leu Ser Ala Arg Gln
                        165                 170                 175

Leu Gly Val Met Pro Asp Leu Val Leu Asp Met Phe Ile Asn Gly Tyr
                    180                 185                 190

Tyr Leu Asn Val Phe Lys Thr Gln Ser Thr Asp Val Asn Arg Pro Tyr
                    195                 200                 205

Gln Asp Lys Asp Lys Arg Gly Gly Ile Phe Asp Ala Val Phe Thr Arg
        210                 215                 220

Gly Asp Gln Thr Thr Leu Leu Thr Ala Arg His Asp Leu Lys Asn Lys
        225                 230                 235                 240

Gly Leu Asn Asp Ile Ser Thr Ile Ile Lys Gln Glu Leu Thr Glu Gly
                        245                 250                 255

Arg Ala Leu Ala Leu Ser His Thr Tyr Ala Asn Val Ser Ile Ser His
                    260                 265                 270

Val Ile Asn Leu Trp Gly Ala Asp Phe Asn Ala Glu Gly Asn Leu Glu
                    275                 280                 285

Ala Ile Tyr Val Thr Asp Ser Asp Ala Asn Ala Ser Ile Gly Met Lys
                    290                 295                 300

Lys Tyr Phe Val Gly Ile Asn Ala His Gly His Val Ala Ile Ser Ala
        305                 310                 315                 320

Lys Lys Ile Glu Gly Glu Asn Ile Gly Ala Gln Val Leu Gly Leu Phe
                    325                 330                 335

Thr Leu Ser Ser Gly Lys Asp Ile Trp Gln Lys Leu Ser
                    340                 345

<210> SEQ ID NO 4
<211> LENGTH: 315
<212> TYPE: PRT
<213> ORGANISM: Streptococcus pyogenes

<400> SEQUENCE: 4

Asp Asp Tyr Gln Arg Asn Ala Thr Glu Ala Tyr Ala Lys Glu Val Pro
  1               5                  10                  15

His Gln Ile Thr Ser Val Trp Thr Lys Gly Val Thr Pro Leu Thr Pro
             20                  25                  30

Glu Gln Phe Arg Tyr Asn Asn Glu Asp Val Ile His Ala Pro Tyr Leu
         35                  40                  45

Ala His Gln Gly Trp Tyr Asp Ile Thr Lys Ala Phe Asp Gly Lys Asp
     50                  55                  60
```

```
Asn Leu Leu Cys Gly Ala Ala Thr Ala Gly Asn Met Leu His Trp Trp
 65                  70                  75                  80

Phe Asp Gln Asn Lys Thr Glu Ile Glu Ala Tyr Leu Ser Lys His Pro
                 85                  90                  95

Glu Lys Gln Lys Ile Ile Phe Asn Asn Gln Glu Leu Phe Asp Leu Lys
            100                 105                 110

Ala Ala Ile Asp Thr Lys Asp Ser Gln Thr Asn Ser Gln Leu Phe Asn
            115                 120                 125

Tyr Phe Arg Asp Lys Ala Phe Pro Asn Leu Ser Ala Arg Gln Leu Gly
130                 135                 140

Val Met Pro Asp Leu Val Leu Asp Met Phe Ile Asn Gly Tyr Tyr Leu
145                 150                 155                 160

Asn Val Phe Lys Thr Gln Ser Thr Asp Val Asn Arg Pro Tyr Gln Asp
                165                 170                 175

Lys Asp Lys Arg Gly Gly Ile Phe Asp Ala Val Phe Thr Arg Gly Asp
            180                 185                 190

Gln Thr Thr Leu Leu Thr Ala Arg His Asp Leu Lys Asn Lys Gly Leu
            195                 200                 205

Asn Asp Ile Ser Thr Ile Ile Lys Gln Glu Leu Thr Glu Gly Arg Ala
210                 215                 220

Leu Ala Leu Ser His Thr Tyr Ala Asn Val Ser Ile Ser His Val Ile
225                 230                 235                 240

Asn Leu Trp Gly Ala Asp Phe Asn Ala Glu Gly Asn Leu Glu Ala Ile
                245                 250                 255

Tyr Val Thr Asp Ser Asp Ala Asn Ala Ser Ile Gly Met Lys Lys Tyr
            260                 265                 270

Phe Val Gly Ile Asn Ala His Gly His Val Ala Ile Ser Ala Lys Lys
            275                 280                 285

Ile Glu Gly Glu Asn Ile Gly Ala Gln Val Leu Gly Leu Phe Thr Leu
290                 295                 300

Ser Ser Gly Lys Asp Ile Trp Gln Lys Leu Ser
305                 310                 315

<210> SEQ ID NO 5
<211> LENGTH: 313
<212> TYPE: PRT
<213> ORGANISM: Streptococcus pyogenes

<400> SEQUENCE: 5

Asp Asp Tyr Gln Arg Asn Ala Thr Glu Ala Tyr Ala Lys Glu Val Pro
 1               5                  10                  15

His Gln Ile Thr Ser Val Trp Thr Lys Gly Val Thr Pro Leu Thr Pro
                 20                  25                  30

Glu Gln Phe Arg Tyr Asn Asn Glu Asp Val Phe His Ala Pro Tyr Val
             35                  40                  45

Ala Asn Gln Gly Trp Tyr Asp Ile Thr Lys Ala Phe Asp Gly Lys Asp
            50                  55                  60

Asn Leu Leu Cys Gly Ala Ala Thr Ala Gly Asn Met Leu His Trp Trp
 65                  70                  75                  80

Phe Asp Gln Asn Lys Asp Gln Ile Lys Arg Tyr Leu Glu Glu His Pro
                 85                  90                  95

Glu Lys Gln Lys Ile Asn Phe Asn Gly Asp Asn Met Phe Asp Val Lys
            100                 105                 110

Lys Ala Ile Asp Thr Lys Asn His Gln Leu Asp Ser Lys Leu Phe Asn
            115                 120                 125
```

Tyr Phe Lys Glu Lys Ala Phe Pro Gly Leu Ser Ala Arg Arg Ile Gly
            130                 135                 140

Val Phe Pro Asp His Val Ile Asp Met Phe Ile Asn Gly Tyr Arg Leu
145                 150                 155                 160

Ser Leu Thr Asn His Gly Pro Thr Pro Val Lys Glu Gly Ser Lys Asp
            165                 170                 175

Pro Arg Gly Gly Ile Phe Asp Ala Val Phe Thr Arg Gly Asn Gln Ser
            180                 185                 190

Lys Leu Leu Thr Ser Arg His Asp Phe Lys Asn Lys Asn Leu Asn Asp
            195                 200                 205

Ile Ser Thr Ile Ile Lys Gln Glu Leu Thr Lys Gly Lys Ala Leu Gly
210                 215                 220

Leu Ser His Thr Tyr Ala Asn Val Ser Ile Asn His Val Ile Asn Leu
225                 230                 235                 240

Trp Gly Ala Asp Phe Asn Ala Glu Gly Asn Leu Glu Ala Ile Tyr Val
            245                 250                 255

Thr Asp Ser Asp Ser Asn Ala Ser Ile Gly Met Lys Lys Tyr Phe Val
            260                 265                 270

Gly Val Asn Ala His Gly His Val Ala Ile Ser Ala Lys Lys Ile Glu
            275                 280                 285

Gly Glu Asn Ile Gly Ala Gln Val Leu Gly Leu Phe Thr Leu Ser Thr
290                 295                 300

Gly Gln Asp Ser Trp Gln Lys Leu Ser
305                 310

<210> SEQ ID NO 6
<211> LENGTH: 315
<212> TYPE: PRT
<213> ORGANISM: Streptococcus pyogenes

<400> SEQUENCE: 6

Asp Asp Tyr Gln Arg Asn Ala Thr Glu Ala Tyr Ala Lys Glu Val Pro
1               5                   10                  15

His Gln Ile Thr Ser Val Trp Thr Lys Gly Val Thr Pro Leu Thr Pro
            20                  25                  30

Glu Gln Phe Arg Tyr Asn Asn Glu Asp Val Ile His Ala Pro Tyr Leu
        35                  40                  45

Ala Asn Gln Gly Trp Tyr Asp Ile Thr Lys Ala Phe Asp Gly Lys Asp
    50                  55                  60

Asn Leu Leu Cys Gly Ala Ala Thr Ala Gly Asn Met Leu His Trp Trp
65              70                  75                  80

Phe Asp Gln Asn Lys Thr Glu Ile Glu Ala Tyr Leu Ser Lys His Pro
            85                  90                  95

Glu Lys Gln Lys Ile Ile Phe Arg Asn Gln Glu Leu Phe Asp Leu Lys
        100                 105                 110

Glu Ala Ile Arg Thr Lys Asp Ser Gln Thr Asn Ser Gln Leu Phe Glu
    115                 120                 125

Tyr Phe Arg Asp Lys Ala Phe Pro Tyr Leu Ser Ala Arg Gln Leu Gly
            130                 135                 140

Val Met Pro Asp Leu Val Leu Asp Met Phe Ile Asn Gly Tyr Tyr Leu
145                 150                 155                 160

Asn Val Phe Lys Thr Gln Ser Thr Asp Val Lys Arg Pro Tyr Gln Asp
            165                 170                 175

Lys Asp Lys Arg Gly Gly Ile Phe Asp Ala Val Phe Thr Arg Gly Asn

```
                180                 185                 190
Gln Thr Thr Leu Leu Thr Ala Arg His Asp Leu Lys Asn Lys Gly Leu
            195                 200                 205

Asn Asp Ile Ser Thr Ile Ile Lys Glu Glu Leu Thr Lys Gly Arg Ala
210                 215                 220

Leu Ala Leu Ser His Thr Tyr Ala Asn Val Ser Ile Ser His Val Ile
225                 230                 235                 240

Asn Leu Trp Gly Ala Asp Phe Asn Ala Glu Gly Asn Leu Glu Ala Ile
                245                 250                 255

Tyr Val Thr Asp Ser Asp Ala Asn Ala Ser Ile Gly Met Lys Lys Tyr
            260                 265                 270

Phe Val Gly Ile Asn Lys His Gly His Val Ala Ile Ser Ala Lys Lys
        275                 280                 285

Ile Glu Gly Glu Asn Ile Gly Ala Gln Val Leu Gly Leu Phe Thr Leu
    290                 295                 300

Ser Ser Gly Lys Asp Ile Trp Gln Lys Leu Asn
305                 310                 315

<210> SEQ ID NO 7
<211> LENGTH: 315
<212> TYPE: PRT
<213> ORGANISM: Streptococcus pyogenes

<400> SEQUENCE: 7

Asp Asp Tyr Gln Arg Asn Ala Thr Glu Ala Tyr Ala Lys Glu Val Pro
1               5                   10                  15

His Gln Ile Thr Ser Val Trp Thr Lys Gly Val Thr Pro Leu Thr Pro
            20                  25                  30

Glu Gln Phe Arg Tyr Asn Asn Glu Asp Val Ile His Ala Pro Tyr Leu
        35                  40                  45

Ala His Gln Gly Trp Tyr Asp Ile Thr Lys Thr Phe Asn Gly Lys Asp
    50                  55                  60

Asn Leu Leu Cys Gly Ala Ala Thr Ala Gly Asn Met Leu His Trp Trp
65                  70                  75                  80

Phe Asp Gln Asn Lys Thr Glu Ile Glu Ala Tyr Leu Ser Lys His Pro
                85                  90                  95

Glu Lys Gln Lys Ile Ile Phe Asn Asn Glu Glu Leu Phe Asp Leu Lys
            100                 105                 110

Ala Ala Ile Asp Thr Lys Asp Ser Gln Thr Asn Ser Gln Leu Phe Asn
        115                 120                 125

Tyr Phe Lys Glu Lys Ala Phe Pro Asn Leu Ser Thr Arg Gln Leu Gly
    130                 135                 140

Val Met Pro Asp Leu Val Leu Asp Met Phe Ile Asn Gly Tyr Tyr Leu
145                 150                 155                 160

Asn Val Phe Lys Thr Gln Ser Thr Asp Val Asn Arg Pro Tyr Gln Asp
                165                 170                 175

Lys Asp Lys Arg Gly Gly Ile Phe Asp Ala Val Phe Thr Arg Gly Asn
            180                 185                 190

Gln Thr Thr Leu Leu Thr Ala Arg His Asp Phe Lys Glu Lys Gly Leu
        195                 200                 205

Lys Asp Ile Ser Thr Ile Ile Lys Gln Glu Leu Thr Glu Gly Arg Ala
    210                 215                 220

Leu Ala Leu Ser His Thr Tyr Ala Asn Val Ser Ile Ser His Val Ile
225                 230                 235                 240
```

```
Asn Leu Trp Gly Ala Asp Phe Asp Ala Glu Gly Asn Leu Lys Ala Ile
                245                 250                 255

Tyr Val Thr Asp Ser Asp Ala Asn Ala Ser Ile Gly Met Lys Lys Tyr
            260                 265                 270

Phe Val Gly Ile Asn Ala His Gly Lys Val Ala Ile Ser Ala Lys Lys
            275                 280                 285

Ile Glu Gly Glu Asn Ile Gly Ala Gln Val Leu Gly Leu Phe Thr Leu
            290                 295                 300

Ser Ser Gly Lys Asp Ile Trp Gln Gln Leu Ser
305                 310                 315

<210> SEQ ID NO 8
<211> LENGTH: 315
<212> TYPE: PRT
<213> ORGANISM: Streptococcus pyogenes

<400> SEQUENCE: 8

Asp Ser Phe Ser Ala Asn Gln Glu Ile Arg Tyr Ser Glu Val Thr Pro
1               5                   10                  15

Tyr His Val Thr Ser Val Trp Thr Lys Gly Val Thr Pro Leu Thr Pro
            20                  25                  30

Glu Gln Phe Arg Tyr Asn Asn Glu Asp Val Ile His Ala Pro Tyr Leu
        35                  40                  45

Ala His Gln Gly Trp Tyr Asp Ile Thr Lys Ala Phe Asp Gly Lys Asp
    50                  55                  60

Asn Leu Leu Cys Gly Ala Ala Thr Ala Gly Asn Met Leu His Trp Trp
65                  70                  75                  80

Phe Asp Gln Asn Lys Thr Glu Ile Glu Ala Tyr Leu Ser Lys His Pro
                85                  90                  95

Glu Lys Gln Lys Ile Ile Phe Asn Asn Gln Glu Leu Phe Asp Leu Lys
            100                 105                 110

Ala Ala Ile Asp Thr Lys Asp Ser Gln Thr Asn Ser Gln Leu Phe Asn
            115                 120                 125

Tyr Phe Arg Asp Lys Ala Phe Pro Asn Leu Ser Ala Arg Gln Leu Gly
        130                 135                 140

Val Met Pro Asp Leu Val Leu Asp Met Phe Ile Asn Gly Tyr Tyr Leu
145                 150                 155                 160

Asn Val Phe Lys Thr Gln Ser Thr Asp Val Asn Arg Pro Tyr Gln Asp
                165                 170                 175

Lys Asp Lys Arg Gly Gly Ile Phe Asp Ala Val Phe Thr Arg Gly Asp
            180                 185                 190

Gln Thr Thr Leu Leu Thr Ala Arg His Asp Leu Lys Asn Lys Gly Leu
        195                 200                 205

Asn Asp Ile Ser Thr Ile Ile Lys Gln Glu Leu Thr Glu Gly Arg Ala
    210                 215                 220

Leu Ala Leu Ser His Thr Tyr Ala Asn Val Ser Ile Ser His Val Ile
225                 230                 235                 240

Asn Leu Trp Gly Ala Asp Phe Asn Ala Glu Gly Asn Leu Glu Ala Ile
                245                 250                 255

Tyr Val Thr Asp Ser Asp Ala Asn Ala Ser Ile Gly Met Lys Lys Tyr
            260                 265                 270

Phe Val Gly Ile Asn Ala His Gly His Val Ala Ile Ser Ala Lys Lys
            275                 280                 285

Ile Glu Gly Glu Asn Ile Gly Ala Gln Val Leu Gly Leu Phe Thr Leu
            290                 295                 300
```

```
Ser Ser Gly Lys Asp Ile Trp Gln Lys Leu Ser
305                 310                 315

<210> SEQ ID NO 9
<211> LENGTH: 295
<212> TYPE: PRT
<213> ORGANISM: Streptococcus pyogenes

<400> SEQUENCE: 9

Ser Val Trp Thr Lys Gly Val Thr Pro Leu Thr Pro Glu Gln Phe Arg
1               5                   10                  15

Tyr Asn Asn Glu Asp Val Ile His Ala Pro Tyr Leu Ala His Gln Gly
            20                  25                  30

Trp Tyr Asp Ile Thr Lys Ala Phe Asp Gly Lys Asp Asn Leu Leu Cys
        35                  40                  45

Gly Ala Ala Thr Ala Gly Asn Met Leu His Trp Trp Phe Asp Gln Asn
    50                  55                  60

Lys Thr Glu Ile Glu Ala Tyr Leu Ser Lys His Pro Glu Lys Gln Lys
65                  70                  75                  80

Ile Ile Phe Asn Asn Gln Glu Leu Phe Asp Leu Lys Ala Ala Ile Asp
                85                  90                  95

Thr Lys Asp Ser Gln Thr Asn Ser Gln Leu Phe Asn Tyr Phe Arg Asp
            100                 105                 110

Lys Ala Phe Pro Asn Leu Ser Ala Arg Gln Leu Gly Val Met Pro Asp
        115                 120                 125

Leu Val Leu Asp Met Phe Ile Asn Gly Tyr Tyr Leu Asn Val Phe Lys
    130                 135                 140

Thr Gln Ser Thr Asp Val Asn Arg Pro Tyr Gln Asp Lys Asp Lys Arg
145                 150                 155                 160

Gly Gly Ile Phe Asp Ala Val Phe Thr Arg Gly Asp Gln Thr Thr Leu
                165                 170                 175

Leu Thr Ala Arg His Asp Leu Lys Asn Lys Gly Leu Asn Asp Ile Ser
            180                 185                 190

Thr Ile Ile Lys Gln Glu Leu Thr Glu Gly Arg Ala Leu Ala Leu Ser
        195                 200                 205

His Thr Tyr Ala Asn Val Ser Ile Ser His Val Ile Asn Leu Trp Gly
    210                 215                 220

Ala Asp Phe Asn Ala Glu Gly Asn Leu Glu Ala Ile Tyr Val Thr Asp
225                 230                 235                 240

Ser Asp Ala Asn Ala Ser Ile Gly Met Lys Lys Tyr Phe Val Gly Ile
                245                 250                 255

Asn Ala His Gly His Val Ala Ile Ser Ala Lys Lys Ile Glu Gly Glu
            260                 265                 270

Asn Ile Gly Ala Gln Val Leu Gly Leu Phe Thr Leu Ser Ser Gly Lys
        275                 280                 285

Asp Ile Trp Gln Lys Leu Ser
    290                 295

<210> SEQ ID NO 10
<211> LENGTH: 314
<212> TYPE: PRT
<213> ORGANISM: Streptococcus pyogenes

<400> SEQUENCE: 10

Asp Asp Tyr Gln Arg Asn Ala Thr Glu Ala Tyr Ala Lys Glu Val Pro
1               5                   10                  15
```

His Gln Ile Thr Ser Val Trp Thr Lys Gly Val Thr Pro Leu Thr Pro
        20                  25                  30

Glu Gln Phe Thr Gln Gly Glu Asp Val Ile His Ala Pro Tyr Leu Ala
                35                  40                  45

His Gln Gly Trp Tyr Asp Ile Thr Lys Ala Phe Asp Gly Lys Asp Asn
    50                  55                  60

Leu Leu Cys Gly Ala Ala Thr Ala Gly Asn Met Leu His Trp Trp Phe
65                  70                  75                  80

Asp Gln Asn Lys Thr Glu Ile Glu Ala Tyr Leu Ser Lys His Pro Glu
                85                  90                  95

Lys Gln Lys Ile Ile Phe Asn Asn Gln Glu Leu Phe Asp Leu Lys Ala
            100                 105                 110

Ala Ile Asp Thr Lys Asp Ser Gln Thr Asn Ser Gln Leu Phe Asn Tyr
        115                 120                 125

Phe Arg Asp Lys Ala Phe Pro Asn Leu Ser Ala Arg Gln Leu Gly Val
130                 135                 140

Met Pro Asp Leu Val Leu Asp Met Phe Ile Asn Gly Tyr Tyr Leu Asn
145                 150                 155                 160

Val Phe Lys Thr Gln Ser Thr Asp Val Asn Arg Pro Tyr Gln Asp Lys
                165                 170                 175

Asp Lys Arg Gly Gly Ile Phe Asp Ala Val Phe Thr Arg Gly Asp Gln
            180                 185                 190

Thr Thr Leu Leu Thr Ala Arg His Asp Leu Lys Asn Lys Gly Leu Asn
        195                 200                 205

Asp Ile Ser Thr Ile Ile Lys Gln Glu Leu Thr Glu Gly Arg Ala Leu
    210                 215                 220

Ala Leu Ser His Thr Tyr Ala Asn Val Ser Ile Ser His Val Ile Asn
225                 230                 235                 240

Leu Trp Gly Ala Asp Phe Asn Ala Glu Gly Asn Leu Glu Ala Ile Tyr
                245                 250                 255

Val Thr Asp Ser Asp Ala Asn Ala Ser Ile Gly Met Lys Lys Tyr Phe
            260                 265                 270

Val Gly Ile Asn Ala His Gly His Val Ala Ile Ser Ala Lys Lys Ile
        275                 280                 285

Glu Gly Glu Asn Ile Gly Ala Gln Val Leu Gly Leu Phe Thr Leu Ser
    290                 295                 300

Ser Gly Lys Asp Ile Trp Gln Lys Leu Ser
305                 310

<210> SEQ ID NO 11
<211> LENGTH: 312
<212> TYPE: PRT
<213> ORGANISM: Streptococcus pyogenes

<400> SEQUENCE: 11

Asp Asp Tyr Gln Arg Asn Ala Thr Glu Ala Tyr Ala Lys Glu Val Pro
1               5                   10                  15

His Gln Ile Thr Ser Val Trp Thr Lys Gly Val Thr Pro Pro Glu Gln
        20                  25                  30

Phe Thr Gln Gly Glu Asp Val Ile His Ala Pro Tyr Leu Ala His Gln
                35                  40                  45

Gly Trp Tyr Asp Ile Thr Lys Ala Phe Asp Gly Lys Asp Asn Leu Leu
    50                  55                  60

Cys Gly Ala Ala Thr Ala Gly Asn Met Leu His Trp Trp Phe Asp Gln

```
                 65                  70                  75                  80
Asn Lys Thr Glu Ile Glu Ala Tyr Leu Ser Lys His Pro Glu Lys Gln
                 85                  90                  95

Lys Ile Ile Phe Asn Asn Gln Glu Leu Phe Asp Leu Lys Ala Ala Ile
                100                 105                 110

Asp Thr Lys Asp Ser Gln Thr Asn Ser Gln Leu Phe Asn Tyr Phe Arg
                115                 120                 125

Asp Lys Ala Phe Pro Asn Leu Ser Ala Arg Gln Leu Gly Val Met Pro
            130                 135                 140

Asp Leu Val Leu Asp Met Phe Ile Asn Gly Tyr Tyr Leu Asn Val Phe
145                 150                 155                 160

Lys Thr Gln Ser Thr Asp Val Asn Arg Pro Tyr Gln Asp Lys Asp Lys
                165                 170                 175

Arg Gly Gly Ile Phe Asp Ala Val Phe Thr Arg Gly Asp Gln Thr Thr
            180                 185                 190

Leu Leu Thr Ala Arg His Asp Leu Lys Asn Lys Gly Leu Asn Asp Ile
            195                 200                 205

Ser Thr Ile Ile Lys Gln Glu Leu Thr Glu Gly Arg Ala Leu Ala Leu
            210                 215                 220

Ser His Thr Tyr Ala Asn Val Ser Ile Ser His Val Ile Asn Leu Trp
225                 230                 235                 240

Gly Ala Asp Phe Asn Ala Glu Gly Asn Leu Glu Ala Ile Tyr Val Thr
                245                 250                 255

Asp Ser Asp Ala Asn Ala Ser Ile Gly Met Lys Lys Tyr Phe Val Gly
            260                 265                 270

Ile Asn Ala His Gly His Val Ala Ile Ser Ala Lys Lys Ile Glu Gly
            275                 280                 285

Glu Asn Ile Gly Ala Gln Val Leu Gly Leu Phe Thr Leu Ser Ser Gly
            290                 295                 300

Lys Asp Ile Trp Gln Lys Leu Ser
305                 310

<210> SEQ ID NO 12
<211> LENGTH: 313
<212> TYPE: PRT
<213> ORGANISM: Streptococcus pyogenes

<400> SEQUENCE: 12

Asp Asp Tyr Gln Arg Asn Ala Thr Glu Ala Tyr Ala Lys Glu Val Pro
1               5                   10                  15

His Gln Ile Thr Ser Val Trp Thr Lys Gly Val Thr Pro Pro Glu Gln
                20                  25                  30

Phe Arg Tyr Asn Asn Glu Asp Val Ile His Ala Pro Tyr Leu Ala His
            35                  40                  45

Gln Gly Trp Tyr Asp Ile Thr Lys Ala Phe Asp Gly Lys Asp Asn Leu
        50                  55                  60

Leu Cys Gly Ala Ala Thr Ala Gly Asn Met Leu His Trp Trp Phe Asp
65                  70                  75                  80

Gln Asn Lys Thr Glu Ile Glu Ala Tyr Leu Ser Lys His Pro Glu Lys
                85                  90                  95

Gln Lys Ile Ile Phe Asn Asn Gln Glu Leu Phe Asp Leu Lys Ala Ala
                100                 105                 110

Ile Asp Thr Lys Asp Ser Gln Thr Asn Ser Gln Leu Phe Asn Tyr Phe
            115                 120                 125
```

Arg Asp Lys Ala Phe Pro Asn Leu Ser Ala Arg Gln Leu Gly Val Met
130                 135                 140

Pro Asp Leu Val Leu Asp Met Phe Ile Asn Gly Tyr Tyr Leu Asn Val
145                 150                 155                 160

Phe Lys Thr Gln Ser Thr Asp Val Asn Arg Pro Tyr Gln Asp Lys Asp
                165                 170                 175

Lys Arg Gly Gly Ile Phe Asp Ala Val Phe Thr Arg Gly Asp Gln Thr
            180                 185                 190

Thr Leu Leu Thr Ala Arg His Asp Leu Lys Asn Lys Gly Leu Asn Asp
        195                 200                 205

Ile Ser Thr Ile Ile Lys Gln Glu Leu Thr Glu Gly Arg Ala Leu Ala
210                 215                 220

Leu Ser His Thr Tyr Ala Asn Val Ser Ile Ser His Val Ile Asn Leu
225                 230                 235                 240

Trp Gly Ala Asp Phe Asn Ala Glu Gly Asn Leu Glu Ala Ile Tyr Val
                245                 250                 255

Thr Asp Ser Asp Ala Asn Ala Ser Ile Gly Met Lys Lys Tyr Phe Val
            260                 265                 270

Gly Ile Asn Ala His Gly His Val Ala Ile Ser Ala Lys Lys Ile Glu
        275                 280                 285

Gly Glu Asn Ile Gly Ala Gln Val Leu Gly Leu Phe Thr Leu Ser Ser
290                 295                 300

Gly Lys Asp Ile Trp Gln Lys Leu Ser
305                 310

<210> SEQ ID NO 13
<211> LENGTH: 312
<212> TYPE: PRT
<213> ORGANISM: Streptococcus pyogenes

<400> SEQUENCE: 13

Asp Asp Tyr Gln Arg Asn Ala Thr Glu Ala Tyr Ala Lys Glu Val Pro
1               5                   10                  15

His Gln Ile Thr Ser Val Trp Thr Lys Gly Val Thr Pro Pro Glu Gln
                20                  25                  30

Phe Thr Gln Gly Glu Asp Val Ile His Ala Pro Tyr Leu Ala His Gln
            35                  40                  45

Gly Trp Tyr Asp Ile Thr Lys Ala Phe Asp Gly Lys Asp Asn Leu Leu
        50                  55                  60

Cys Gly Ala Ala Thr Ala Gly Asn Met Leu His Trp Trp Phe Asp Gln
65                  70                  75                  80

Asn Lys Thr Glu Ile Glu Ala Tyr Leu Ser Lys His Pro Glu Lys Gln
                85                  90                  95

Lys Ile Ile Ile Asn Asn Gln Glu Leu Phe Asp Leu Lys Ala Ala Ile
            100                 105                 110

Asp Thr Lys Asp Ser Gln Thr Asn Ser Gln Leu Phe Asn Tyr Phe Arg
        115                 120                 125

Asp Lys Ala Phe Pro Asn Leu Ser Ala Arg Gln Leu Gly Val Met Pro
130                 135                 140

Asp Leu Val Leu Asp Met Phe Ile Asn Gly Tyr Tyr Leu Asn Val Phe
145                 150                 155                 160

Lys Thr Gln Ser Thr Asp Val Asn Arg Pro Tyr Gln Asp Lys Asp Lys
                165                 170                 175

Arg Gly Gly Ile Phe Asp Ala Val Phe Thr Arg Gly Asp Gln Thr Thr
            180                 185                 190

```
Leu Leu Thr Ala Arg His Asp Leu Lys Asn Lys Gly Leu Asn Asp Ile
            195                 200                 205

Ser Thr Ile Ile Lys Gln Glu Leu Thr Glu Gly Arg Ala Leu Ala Leu
210                 215                 220

Ser His Thr Tyr Ala Asn Val Ser Ile Ser His Val Ile Asn Leu Trp
225                 230                 235                 240

Gly Ala Asp Phe Asn Ala Glu Gly Asn Leu Glu Ala Ile Tyr Val Thr
            245                 250                 255

Asp Ser Asp Ala Asn Ala Ser Ile Gly Met Lys Lys Tyr Phe Val Gly
            260                 265                 270

Ile Asn Ala His Gly His Val Ala Ile Ser Ala Lys Lys Ile Glu Gly
            275                 280                 285

Glu Asn Ile Gly Ala Gln Val Leu Gly Leu Phe Thr Leu Ser Ser Gly
            290                 295                 300

Lys Asp Ile Trp Gln Lys Leu Ser
305                 310

<210> SEQ ID NO 14
<211> LENGTH: 312
<212> TYPE: PRT
<213> ORGANISM: Streptococcus pyogenes

<400> SEQUENCE: 14

Asp Asp Tyr Gln Arg Asn Ala Thr Glu Ala Tyr Ala Lys Glu Val Pro
1               5                   10                  15

His Gln Ile Thr Ser Val Trp Thr Lys Gly Val Thr Pro Pro Glu Gln
            20                  25                  30

Phe Thr Gln Gly Glu Asp Val Ile His Ala Pro Tyr Leu Ala His Gln
        35                  40                  45

Gly Trp Tyr Asp Ile Thr Lys Ala Phe Asp Gly Lys Asp Asn Leu Leu
    50                  55                  60

Cys Gly Ala Ala Thr Ala Gly Asn Met Leu His Trp Trp Phe Asp Gln
65                  70                  75                  80

Asn Lys Thr Glu Ile Glu Ala Tyr Leu Ser Lys His Pro Glu Lys Gln
                85                  90                  95

Lys Ile Ile Phe Arg Asn Gln Glu Leu Phe Asp Leu Lys Ala Ala Ile
            100                 105                 110

Asp Thr Lys Asp Ser Gln Thr Asn Ser Gln Leu Phe Asn Tyr Phe Arg
            115                 120                 125

Asp Lys Ala Phe Pro Asn Leu Ser Ala Arg Gln Leu Gly Val Met Pro
130                 135                 140

Asp Leu Val Leu Asp Met Phe Ile Asn Gly Tyr Tyr Leu Asn Val Phe
145                 150                 155                 160

Lys Thr Gln Ser Thr Asp Val Asn Arg Pro Tyr Gln Asp Lys Asp Lys
                165                 170                 175

Arg Gly Gly Ile Phe Asp Ala Val Phe Thr Arg Gly Asp Gln Thr Thr
            180                 185                 190

Leu Leu Thr Ala Arg His Asp Leu Lys Asn Lys Gly Leu Asn Asp Ile
            195                 200                 205

Ser Thr Ile Ile Lys Gln Glu Leu Thr Glu Gly Arg Ala Leu Ala Leu
210                 215                 220

Ser His Thr Tyr Ala Asn Val Ser Ile Ser His Val Ile Asn Leu Trp
225                 230                 235                 240

Gly Ala Asp Phe Asn Ala Glu Gly Asn Leu Glu Ala Ile Tyr Val Thr
```

```
                       245                 250                 255
Asp Ser Asp Ala Asn Ala Ser Ile Gly Met Lys Lys Tyr Phe Val Gly
            260                 265                 270

Ile Asn Ala His Gly His Val Ala Ile Ser Ala Lys Lys Ile Glu Gly
            275                 280                 285

Glu Asn Ile Gly Ala Gln Val Leu Gly Leu Phe Thr Leu Ser Ser Gly
            290                 295                 300

Lys Asp Ile Trp Gln Lys Leu Ser
305                 310

<210> SEQ ID NO 15
<211> LENGTH: 312
<212> TYPE: PRT
<213> ORGANISM: Streptococcus pyogenes

<400> SEQUENCE: 15

Asp Asp Tyr Gln Arg Asn Ala Thr Glu Ala Tyr Ala Lys Glu Val Pro
1               5                   10                  15

His Gln Ile Thr Ser Val Trp Thr Lys Gly Val Thr Pro Pro Glu Gln
            20                  25                  30

Phe Thr Gln Gly Glu Asp Val Ile His Ala Pro Tyr Leu Ala His Gln
        35                  40                  45

Gly Trp Tyr Asp Ile Thr Lys Ala Phe Asp Gly Lys Asp Asn Leu Leu
    50                  55                  60

Cys Gly Ala Ala Thr Ala Gly Asn Met Leu His Trp Trp Phe Asp Gln
65                  70                  75                  80

Asn Lys Thr Glu Ile Glu Ala Tyr Leu Ser Lys His Pro Glu Lys Gln
                85                  90                  95

Lys Ile Ile Ile Arg Asn Gln Glu Leu Phe Asp Leu Lys Ala Ala Ile
            100                 105                 110

Asp Thr Lys Asp Ser Gln Thr Asn Ser Gln Leu Phe Asn Tyr Phe Arg
        115                 120                 125

Asp Lys Ala Phe Pro Asn Leu Ser Ala Arg Gln Leu Gly Val Met Pro
    130                 135                 140

Asp Leu Val Leu Asp Met Phe Ile Asn Gly Tyr Tyr Leu Asn Val Phe
145                 150                 155                 160

Lys Thr Gln Ser Thr Asp Val Asn Arg Pro Tyr Gln Asp Lys Asp Lys
                165                 170                 175

Arg Gly Gly Ile Phe Asp Ala Val Phe Thr Arg Gly Asp Gln Thr Thr
            180                 185                 190

Leu Leu Thr Ala Arg His Asp Leu Lys Asn Lys Gly Leu Asn Asp Ile
        195                 200                 205

Ser Thr Ile Ile Lys Gln Glu Leu Thr Glu Gly Arg Ala Leu Ala Leu
    210                 215                 220

Ser His Thr Tyr Ala Asn Val Ser Ile Ser His Val Ile Asn Leu Trp
225                 230                 235                 240

Gly Ala Asp Phe Asn Ala Glu Gly Asn Leu Glu Ala Ile Tyr Val Thr
                245                 250                 255

Asp Ser Asp Ala Asn Ala Ser Ile Gly Met Lys Lys Tyr Phe Val Gly
            260                 265                 270

Ile Asn Ala His Gly His Val Ala Ile Ser Ala Lys Lys Ile Glu Gly
            275                 280                 285

Glu Asn Ile Gly Ala Gln Val Leu Gly Leu Phe Thr Leu Ser Ser Gly
            290                 295                 300
```

Lys Asp Ile Trp Gln Lys Leu Ser
305                 310

<210> SEQ ID NO 16
<211> LENGTH: 312
<212> TYPE: PRT
<213> ORGANISM: Streptococcus pyogenes

<400> SEQUENCE: 16

Asp Asp Tyr Gln Arg Asn Ala Thr Glu Ala Tyr Ala Lys Glu Val Pro
1               5                   10                  15

His Gln Ile Thr Ser Val Trp Thr Lys Gly Val Thr Pro Pro Glu Gln
            20                  25                  30

Phe Thr Gln Gly Glu Asp Val Ile His Ala Pro Tyr Leu Ala Asn Gln
        35                  40                  45

Gly Trp Tyr Asp Ile Thr Lys Ala Phe Asp Gly Lys Asp Asn Leu Leu
    50                  55                  60

Cys Gly Ala Ala Thr Ala Gly Asn Met Leu His Trp Trp Phe Asp Gln
65                  70                  75                  80

Asn Lys Thr Glu Ile Glu Ala Tyr Leu Ser Lys His Pro Glu Lys Gln
                85                  90                  95

Lys Ile Ile Phe Arg Asn Gln Glu Leu Phe Asp Leu Lys Glu Ala Ile
            100                 105                 110

Arg Thr Lys Asp Ser Gln Thr Asn Ser Gln Leu Phe Glu Tyr Phe Arg
        115                 120                 125

Asp Lys Ala Phe Pro Tyr Leu Ser Ala Arg Gln Leu Gly Val Met Pro
    130                 135                 140

Asp Leu Val Leu Asp Met Phe Ile Asn Gly Tyr Tyr Leu Asn Val Phe
145                 150                 155                 160

Lys Thr Gln Ser Thr Asp Val Lys Arg Pro Tyr Gln Asp Lys Asp Lys
                165                 170                 175

Arg Gly Gly Ile Phe Asp Ala Val Phe Thr Arg Gly Asn Gln Thr Thr
            180                 185                 190

Leu Leu Thr Ala Arg His Asp Leu Lys Asn Lys Gly Leu Asn Asp Ile
        195                 200                 205

Ser Thr Ile Ile Lys Glu Glu Leu Thr Lys Gly Arg Ala Leu Ala Leu
    210                 215                 220

Ser His Thr Tyr Ala Asn Val Ser Ile Ser His Val Ile Asn Leu Trp
225                 230                 235                 240

Gly Ala Asp Phe Asn Ala Glu Gly Asn Leu Glu Ala Ile Tyr Val Thr
                245                 250                 255

Asp Ser Asp Ala Asn Ala Ser Ile Gly Met Lys Lys Tyr Phe Val Gly
            260                 265                 270

Ile Asn Lys His Gly His Val Ala Ile Ser Ala Lys Lys Ile Glu Gly
        275                 280                 285

Glu Asn Ile Gly Ala Gln Val Leu Gly Leu Phe Thr Leu Ser Ser Gly
    290                 295                 300

Lys Asp Ile Trp Gln Lys Leu Asn
305                 310

<210> SEQ ID NO 17
<211> LENGTH: 292
<212> TYPE: PRT
<213> ORGANISM: Streptococcus pyogenes

<400> SEQUENCE: 17

Ser Val Trp Thr Lys Gly Val Thr Pro Pro Glu Gln Phe Thr Gln Gly
1               5                   10                  15

Glu Asp Val Ile His Ala Pro Tyr Leu Ala His Gln Gly Trp Tyr Asp
            20                  25                  30

Ile Thr Lys Ala Phe Asp Gly Lys Asp Asn Leu Leu Cys Gly Ala Ala
        35                  40                  45

Thr Ala Gly Asn Met Leu His Trp Trp Phe Asp Gln Asn Lys Thr Glu
50                  55                  60

Ile Glu Ala Tyr Leu Ser Lys His Pro Glu Lys Gln Lys Ile Ile Phe
65                  70                  75                  80

Arg Asn Gln Glu Leu Phe Asp Leu Lys Ala Ala Ile Asp Thr Lys Asp
                85                  90                  95

Ser Gln Thr Asn Ser Gln Leu Phe Asn Tyr Phe Arg Asp Lys Ala Phe
            100                 105                 110

Pro Asn Leu Ser Ala Arg Gln Leu Gly Val Met Pro Asp Leu Val Leu
        115                 120                 125

Asp Met Phe Ile Asn Gly Tyr Tyr Leu Asn Val Phe Lys Thr Gln Ser
    130                 135                 140

Thr Asp Val Asn Arg Pro Tyr Gln Asp Lys Asp Lys Arg Gly Gly Ile
145                 150                 155                 160

Phe Asp Ala Val Phe Thr Arg Gly Asn Gln Thr Thr Leu Leu Thr Ala
                165                 170                 175

Arg His Asp Leu Lys Asn Lys Gly Leu Asn Asp Ile Ser Thr Ile Ile
            180                 185                 190

Lys Gln Glu Leu Thr Glu Gly Arg Ala Leu Ala Leu Ser His Thr Tyr
        195                 200                 205

Ala Asn Val Ser Ile Ser His Val Ile Asn Leu Trp Gly Ala Asp Phe
210                 215                 220

Asn Ala Glu Gly Asn Leu Glu Ala Ile Tyr Val Thr Asp Ser Asp Ala
225                 230                 235                 240

Asn Ala Ser Ile Gly Met Lys Lys Tyr Phe Val Gly Ile Asn Ala His
                245                 250                 255

Gly His Val Ala Ile Ser Ala Lys Lys Ile Glu Gly Glu Asn Ile Gly
            260                 265                 270

Ala Gln Val Leu Gly Leu Phe Thr Leu Ser Ser Gly Lys Asp Ile Trp
        275                 280                 285

Gln Lys Leu Ser
    290

<210> SEQ ID NO 18
<211> LENGTH: 312
<212> TYPE: PRT
<213> ORGANISM: Streptococcus pyogenes

<400> SEQUENCE: 18

Asp Asp Tyr Gln Arg Asn Ala Thr Glu Ala Tyr Ala Lys Glu Val Pro
1               5                   10                  15

His Gln Ile Thr Ser Val Trp Thr Lys Gly Val Thr Pro Pro Glu Gln
            20                  25                  30

Phe Thr Gln Gly Glu Asp Val Ile His Ala Pro Tyr Leu Ala His Gln
        35                  40                  45

Gly Trp Tyr Asp Ile Thr Lys Ala Phe Asp Gly Ala Asp Asn Leu Leu
50                  55                  60

Cys Gly Ala Ala Thr Ala Gly Asn Met Leu His Trp Trp Phe Asp Gln
65                  70                  75                  80

```
Asn Lys Thr Glu Ile Glu Ala Tyr Leu Ser Lys His Pro Glu Lys Gln
                 85                  90                  95

Lys Ile Ile Phe Arg Asn Gln Glu Leu Phe Asp Leu Lys Ala Ala Ile
            100                 105                 110

Asp Thr Lys Asp Ser Gln Thr Asn Ser Gln Leu Phe Asn Tyr Phe Arg
            115                 120                 125

Asp Lys Ala Phe Pro Asn Leu Ser Ala Arg Gln Leu Gly Val Met Pro
            130                 135                 140

Asp Leu Val Leu Asp Met Phe Ile Asn Gly Tyr Tyr Leu Asn Val Phe
145                 150                 155                 160

Lys Thr Gln Ser Thr Asp Val Asn Arg Pro Tyr Gln Asp Lys Asp Lys
                165                 170                 175

Arg Gly Gly Ile Phe Asp Ala Val Phe Thr Arg Gly Asn Gln Thr Thr
            180                 185                 190

Leu Leu Thr Ala Arg His Asp Leu Lys Asn Lys Gly Leu Asn Asp Ile
            195                 200                 205

Ser Thr Ile Ile Lys Gln Glu Leu Thr Glu Gly Arg Ala Leu Ala Leu
            210                 215                 220

Ser His Thr Tyr Ala Asn Val Ser Ile Ser His Val Ile Asn Leu Trp
225                 230                 235                 240

Gly Ala Asp Phe Asn Ala Glu Gly Asn Leu Glu Ala Ile Tyr Val Thr
            245                 250                 255

Asp Ser Asp Ala Asn Ala Ser Ile Gly Met Lys Lys Tyr Phe Val Gly
            260                 265                 270

Ile Asn Ala His Gly His Val Ala Ile Ser Ala Lys Lys Ile Glu Gly
            275                 280                 285

Glu Asn Ile Gly Ala Gln Val Leu Gly Leu Phe Thr Leu Ser Ser Gly
            290                 295                 300

Lys Asp Ile Trp Gln Lys Leu Ser
305                 310

<210> SEQ ID NO 19
<211> LENGTH: 292
<212> TYPE: PRT
<213> ORGANISM: Streptococcus pyogenes

<400> SEQUENCE: 19

Ser Val Trp Thr Lys Gly Val Thr Pro Pro Glu Gln Phe Thr Gln Gly
1               5                   10                  15

Glu Asp Val Ile His Ala Pro Tyr Leu Ala His Gln Gly Trp Tyr Asp
            20                  25                  30

Ile Thr Lys Ala Phe Asp Gly Ala Asp Asn Leu Leu Cys Gly Ala Ala
            35                  40                  45

Thr Ala Gly Asn Met Leu His Trp Trp Phe Asp Gln Asn Lys Thr Glu
        50                  55                  60

Ile Glu Ala Tyr Leu Ser Lys His Pro Glu Lys Gln Lys Ile Ile Phe
65                  70                  75                  80

Arg Asn Gln Glu Leu Phe Asp Leu Lys Ala Ala Ile Asp Thr Lys Asp
                85                  90                  95

Ser Gln Thr Asn Ser Gln Leu Phe Asn Tyr Phe Arg Asp Lys Ala Phe
            100                 105                 110

Pro Asn Leu Ser Ala Arg Gln Leu Gly Val Met Pro Asp Leu Val Leu
            115                 120                 125

Asp Met Phe Ile Asn Gly Tyr Tyr Leu Asn Val Phe Lys Thr Gln Ser
```

```
                    130                 135                 140
Thr Asp Val Asn Arg Pro Tyr Gln Asp Lys Asp Lys Arg Gly Gly Ile
145                 150                 155                 160

Phe Asp Ala Val Phe Thr Arg Gly Asn Gln Thr Thr Leu Leu Thr Ala
                    165                 170                 175

Arg His Asp Leu Lys Asn Lys Gly Leu Asn Asp Ile Ser Thr Ile Ile
                180                 185                 190

Lys Gln Glu Leu Thr Glu Gly Arg Ala Leu Ala Leu Ser His Thr Tyr
                195                 200                 205

Ala Asn Val Ser Ile Ser His Val Ile Asn Leu Trp Gly Ala Asp Phe
                210                 215                 220

Asn Ala Glu Gly Asn Leu Glu Ala Ile Tyr Val Thr Asp Ser Asp Ala
225                 230                 235                 240

Asn Ala Ser Ile Gly Met Lys Lys Tyr Phe Val Gly Ile Asn Ala His
                245                 250                 255

Gly His Val Ala Ile Ser Ala Lys Lys Ile Glu Gly Glu Asn Ile Gly
                260                 265                 270

Ala Gln Val Leu Gly Leu Phe Thr Leu Ser Ser Gly Lys Asp Ile Trp
                275                 280                 285

Gln Lys Leu Ser
            290

<210> SEQ ID NO 20
<211> LENGTH: 312
<212> TYPE: PRT
<213> ORGANISM: Streptococcus pyogenes

<400> SEQUENCE: 20

Asp Asp Tyr Gln Arg Asn Ala Thr Glu Ala Tyr Ala Lys Glu Val Pro
1               5                   10                  15

His Gln Ile Thr Ser Val Trp Thr Lys Gly Val Thr Pro Pro Glu Gln
                20                  25                  30

Phe Thr Gln Gly Glu Asp Val Ile His Ala Pro Tyr Leu Ala His Gln
                35                  40                  45

Gly Trp Tyr Asp Ile Thr Lys Ala Phe Asp Gly Lys Asp Asn Leu Leu
            50                  55                  60

Cys Gly Ala Ala Thr Ala Gly Asn Met Leu His Trp Trp Phe Asp Gln
65                  70                  75                  80

Asn Lys Thr Glu Ile Glu Ala Tyr Leu Ser Lys His Pro Glu Lys Gln
                85                  90                  95

Lys Ile Ile Phe Arg Asn Gln Glu Leu Phe Asp Leu Lys Ala Ala Ile
                100                 105                 110

Asp Thr Lys Asp Ser Gln Thr Asn Ser Gln Leu Phe Asn Tyr Phe Arg
                115                 120                 125

Asp Lys Ala Phe Pro Asn Leu Ser Ala Arg Gln Leu Gly Val Met Pro
            130                 135                 140

Asp Leu Val Leu Asp Met Phe Ile Asn Gly Tyr Tyr Leu Asn Val Phe
145                 150                 155                 160

Lys Thr Gln Ser Thr Asp Val Asn Arg Pro Tyr Gln Asp Lys Asp Lys
                165                 170                 175

Arg Gly Gly Ile Phe Asp Ala Val Phe Thr Arg Gly Asn Gln Thr Thr
            180                 185                 190

Leu Leu Thr Ala Arg His Asp Leu Lys Asn Lys Gly Leu Asn Asp Ile
            195                 200                 205
```

```
Ser Thr Ile Ile Lys Gln Glu Leu Thr Glu Gly Arg Ala Leu Ala Leu
210                 215                 220

Ser His Thr Tyr Ala Asn Val Ser Ile Ser His Val Ile Asn Leu Trp
225                 230                 235                 240

Gly Ala Asp Phe Asn Ala Glu Gly Asn Leu Glu Ala Ile Tyr Val Thr
                245                 250                 255

Asp Ser Asp Ala Asn Ala Ser Ile Gly Met Lys Lys Tyr Phe Val Gly
                260                 265                 270

Ile Asn Ala His Gly His Val Ala Ile Ser Ala Lys Lys Ile Glu Gly
                275                 280                 285

Glu Asn Ile Gly Ala Gln Val Leu Gly Leu Phe Thr Leu Ser Ser Gly
290                 295                 300

Lys Asp Ile Trp Gln Lys Leu Ser
305                 310

<210> SEQ ID NO 21
<211> LENGTH: 312
<212> TYPE: PRT
<213> ORGANISM: Streptococcus pyogenes

<400> SEQUENCE: 21

Asp Asp Tyr Gln Arg Asn Ala Thr Glu Ala Tyr Ala Lys Glu Val Pro
1               5                   10                  15

His Gln Ile Thr Ser Val Trp Thr Lys Gly Val Thr Pro Leu Thr Pro
                20                  25                  30

Glu Gln Phe Thr Gln Gly Glu Asp Val Phe His Ala Pro Tyr Val Ala
            35                  40                  45

Asn Gln Gly Trp Tyr Asp Ile Thr Lys Ala Phe Asp Gly Lys Asp Asn
50                  55                  60

Leu Leu Cys Gly Ala Ala Thr Ala Gly Asn Met Leu His Trp Trp Phe
65                  70                  75                  80

Asp Gln Asn Lys Asp Gln Ile Lys Arg Tyr Leu Glu Glu His Pro Glu
                85                  90                  95

Lys Gln Lys Ile Asn Phe Asn Gly Glu Asn Met Phe Asp Val Lys Lys
                100                 105                 110

Ala Ile Asp Thr Lys Asn His Gln Leu Asp Ser Lys Leu Phe Asn Tyr
                115                 120                 125

Phe Lys Glu Lys Ala Phe Pro Tyr Leu Ser Ala Lys His Leu Gly Val
            130                 135                 140

Phe Pro Asp His Val Ile Asp Met Phe Ile Asn Gly Tyr Arg Leu Ser
145                 150                 155                 160

Leu Thr Asn His Gly Pro Thr Pro Val Lys Glu Gly Ser Lys Asp Pro
                165                 170                 175

Arg Gly Gly Ile Phe Asp Ala Val Phe Thr Arg Gly Asn Gln Ser Lys
                180                 185                 190

Leu Leu Thr Ser Arg His Asp Phe Lys Asn Lys Asn Leu Asn Asp Ile
            195                 200                 205

Ser Thr Ile Ile Lys Gln Glu Leu Thr Lys Gly Lys Ala Leu Gly Leu
210                 215                 220

Ser His Thr Tyr Ala Asn Val Arg Ile Asn His Val Ile Asn Leu Trp
225                 230                 235                 240

Gly Ala Asp Phe Asn Ala Glu Gly Asn Leu Glu Ala Ile Tyr Val Thr
                245                 250                 255

Asp Ser Asp Ser Asn Ala Ser Ile Gly Met Lys Lys Tyr Phe Val Gly
                260                 265                 270
```

Val Asn Ala His Gly His Val Ala Ile Ser Ala Lys Lys Ile Glu Gly
        275                 280                 285

Glu Asn Ile Gly Ala Gln Val Leu Gly Leu Phe Thr Leu Ser Thr Gly
290                 295                 300

Gln Asp Ser Trp Gln Lys Leu Ser
305                 310

<210> SEQ ID NO 22
<211> LENGTH: 312
<212> TYPE: PRT
<213> ORGANISM: Streptococcus pyogenes

<400> SEQUENCE: 22

Asp Asp Tyr Gln Arg Asn Ala Thr Glu Ala Tyr Ala Lys Glu Val Pro
1               5                   10                  15

His Gln Ile Thr Ser Val Trp Thr Lys Gly Val Thr Pro Leu Thr Pro
            20                  25                  30

Glu Gln Phe Thr Gln Gly Glu Asp Val Phe His Ala Pro Tyr Val Ala
        35                  40                  45

Asn Gln Gly Trp Tyr Asp Ile Thr Lys Ala Phe Asp Gly Lys Asp Asn
    50                  55                  60

Leu Leu Cys Gly Ala Ala Thr Ala Gly Asn Met Leu His Trp Trp Phe
65                  70                  75                  80

Asp Gln Asn Lys Asp Gln Ile Lys Arg Tyr Leu Glu Glu His Pro Glu
                85                  90                  95

Lys Gln Lys Ile Asn Phe Arg Gly Glu Asn Met Phe Asp Val Lys Glu
            100                 105                 110

Ala Ile Arg Thr Lys Asn His Gln Leu Asp Ser Lys Leu Phe Glu Tyr
        115                 120                 125

Phe Lys Glu Lys Ala Phe Pro Tyr Leu Ser Ala Lys His Leu Gly Val
    130                 135                 140

Phe Pro Asp His Val Ile Asp Met Phe Ile Asn Gly Tyr Arg Leu Ser
145                 150                 155                 160

Leu Thr Asn His Gly Pro Thr Pro Val Lys Lys Gly Ser Lys Asp Pro
                165                 170                 175

Arg Gly Gly Ile Phe Asp Ala Val Phe Thr Arg Gly Asn Gln Ser Lys
            180                 185                 190

Leu Leu Thr Ser Arg His Asp Phe Lys Asn Lys Asn Leu Asn Asp Ile
        195                 200                 205

Ser Thr Ile Ile Lys Ser Glu Leu Thr Asn Gly Lys Ala Leu Gly Leu
    210                 215                 220

Ser His Thr Tyr Ala Asn Val Arg Ile Asn His Val Ile Asn Leu Trp
225                 230                 235                 240

Gly Ala Asp Phe Asn Ala Glu Gly Asn Leu Glu Ala Ile Tyr Val Thr
                245                 250                 255

Asp Ser Asp Ser Asn Ala Ser Ile Gly Met Lys Lys Tyr Phe Val Gly
            260                 265                 270

Val Asn Lys His Gly His Val Ala Ile Ser Ala Lys Lys Ile Glu Gly
        275                 280                 285

Glu Asn Ile Gly Ala Gln Val Leu Gly Leu Phe Thr Leu Ser Thr Gly
    290                 295                 300

Gln Asp Ser Trp Gln Lys Leu Asn
305                 310

<210> SEQ ID NO 23
<211> LENGTH: 312
<212> TYPE: PRT
<213> ORGANISM: Streptococcus pyogenes

<400> SEQUENCE: 23

Asp Asp Tyr Gln Arg Asn Ala Thr Glu Ala Tyr Ala Lys Glu Val Pro
1               5                   10                  15

His Gln Ile Thr Ser Val Trp Thr Lys Gly Val Thr Pro Leu Thr Pro
            20                  25                  30

Glu Gln Phe Thr Gln Gly Glu Asp Val Phe His Ala Pro Tyr Val Ala
        35                  40                  45

Asn Gln Gly Trp Tyr Asp Ile Thr Lys Thr Phe Asn Gly Lys Asp Asp
    50                  55                  60

Leu Leu Cys Gly Ala Ala Thr Ala Gly Asn Met Leu His Trp Trp Phe
65                  70                  75                  80

Asp Gln Asn Lys Asp Gln Ile Lys Arg Tyr Leu Glu Glu His Pro Glu
                85                  90                  95

Lys Gln Lys Ile Asn Phe Asn Gly Glu Gln Met Phe Asp Val Lys Glu
            100                 105                 110

Ala Ile Asp Thr Lys Asn His Gln Leu Asp Ser Lys Leu Phe Glu Tyr
        115                 120                 125

Phe Lys Glu Lys Ala Phe Pro Tyr Leu Ser Thr Lys His Leu Gly Val
    130                 135                 140

Phe Pro Asp His Val Ile Asp Met Phe Ile Asn Gly Tyr Arg Leu Ser
145                 150                 155                 160

Leu Thr Asn His Gly Pro Thr Pro Val Lys Glu Gly Ser Lys Asp Pro
                165                 170                 175

Arg Gly Gly Ile Phe Asp Ala Val Phe Thr Arg Gly Asn Gln Ser Lys
            180                 185                 190

Leu Leu Thr Ser Arg His Asp Phe Lys Glu Lys Asn Leu Lys Glu Ile
        195                 200                 205

Ser Asp Leu Ile Lys Gln Glu Leu Thr Glu Gly Lys Ala Leu Gly Leu
    210                 215                 220

Ser His Thr Tyr Ala Asn Val Arg Ile Asn His Val Ile Asn Leu Trp
225                 230                 235                 240

Gly Ala Asp Phe Asp Ala Glu Gly Asn Leu Lys Ala Ile Tyr Val Thr
                245                 250                 255

Asp Ser Asp Ser Asn Ala Ser Ile Gly Met Lys Lys Tyr Phe Val Gly
            260                 265                 270

Val Asn Ala Ala Gly Lys Val Ala Ile Ser Ala Lys Lys Ile Glu Gly
        275                 280                 285

Glu Asn Ile Gly Ala Gln Val Leu Gly Leu Phe Thr Leu Ser Thr Gly
    290                 295                 300

Gln Asp Ser Trp Asn Gln Thr Ser
305                 310

<210> SEQ ID NO 24
<211> LENGTH: 312
<212> TYPE: PRT
<213> ORGANISM: Streptococcus pyogenes

<400> SEQUENCE: 24

Asp Asp Tyr Gln Arg Asn Ala Thr Glu Ala Tyr Ala Lys Glu Val Pro
1               5                   10                  15

His Gln Ile Thr Ser Val Trp Thr Lys Gly Val Thr Pro Leu Thr Pro

```
            20                  25                  30
Glu Gln Phe Thr Gln Gly Glu Asp Val Phe His Ala Pro Tyr Val Ala
         35                  40                  45

Asn Gln Gly Trp Tyr Asp Ile Thr Lys Thr Phe Asn Gly Lys Asp Asp
 50                  55                  60

Leu Leu Cys Gly Ala Ala Thr Ala Gly Asn Met Leu His Trp Trp Phe
65                  70                  75                  80

Asp Gln Asn Lys Asp Gln Ile Lys Arg Tyr Leu Glu Glu His Pro Glu
                 85                  90                  95

Lys Gln Lys Ile Asn Phe Arg Gly Glu Gln Met Phe Asp Val Lys Glu
            100                 105                 110

Ala Ile Arg Thr Lys Asn His Gln Leu Asp Ser Lys Leu Phe Glu Tyr
        115                 120                 125

Phe Lys Glu Lys Ala Phe Pro Tyr Leu Ser Thr Lys His Leu Gly Val
    130                 135                 140

Phe Pro Asp His Val Ile Asp Met Phe Ile Asn Gly Tyr Arg Leu Ser
145                 150                 155                 160

Leu Thr Asn His Gly Pro Thr Pro Val Lys Lys Gly Ser Lys Asp Pro
                165                 170                 175

Arg Gly Gly Ile Phe Asp Ala Val Phe Thr Arg Gly Asn Gln Ser Lys
            180                 185                 190

Leu Leu Thr Ser Arg His Asp Phe Lys Glu Lys Asn Leu Lys Glu Ile
        195                 200                 205

Ser Asp Leu Ile Lys Glu Glu Leu Thr Lys Gly Lys Ala Leu Gly Leu
    210                 215                 220

Ser His Thr Tyr Ala Asn Val Arg Ile Asn His Val Ile Asn Leu Trp
225                 230                 235                 240

Gly Ala Asp Phe Asp Ala Glu Gly Asn Leu Lys Ala Ile Tyr Val Thr
                245                 250                 255

Asp Ser Asp Ser Asn Ala Ser Ile Gly Met Lys Lys Tyr Phe Val Gly
            260                 265                 270

Val Asn Lys Ala Gly Lys Val Ala Ile Ser Ala Lys Lys Ile Glu Gly
        275                 280                 285

Glu Asn Ile Gly Ala Gln Val Leu Gly Leu Phe Thr Leu Ser Thr Gly
    290                 295                 300

Gln Asp Ser Trp Asn Gln Thr Asn
305                 310

<210> SEQ ID NO 25
<211> LENGTH: 310
<212> TYPE: PRT
<213> ORGANISM: Streptococcus pyogenes

<400> SEQUENCE: 25

Asp Asp Tyr Gln Arg Asn Ala Thr Glu Ala Tyr Ala Lys Glu Val Pro
1               5                   10                  15

His Gln Ile Thr Ser Val Trp Thr Lys Gly Val Thr Pro Pro Glu Gln
            20                  25                  30

Phe Thr Gln Gly Glu Asp Val Ile His Ala Pro Tyr Val Ala Asn Gln
        35                  40                  45

Gly Trp Tyr Asp Ile Thr Lys Ala Phe Asp Gly Lys Asp Asn Leu Leu
    50                  55                  60

Cys Gly Ala Ala Thr Ala Gly Asn Met Leu His Trp Trp Phe Asp Gln
65                  70                  75                  80
```

```
Asn Lys Asp Gln Ile Lys Arg Tyr Leu Glu Glu His Pro Glu Lys Gln
                85                  90                  95

Lys Ile Asn Phe Arg Gly Glu Gln Met Phe Asp Val Lys Lys Ala Ile
            100                 105                 110

Asp Thr Lys Asn His Gln Leu Asp Ser Lys Leu Phe Asn Tyr Phe Lys
            115                 120                 125

Glu Lys Ala Phe Pro Gly Leu Ser Ala Arg Arg Ile Gly Val Phe Pro
130                 135                 140

Asp His Val Ile Asp Met Phe Ile Asn Gly Tyr Arg Leu Ser Leu Thr
145                 150                 155                 160

Asn His Gly Pro Thr Pro Val Lys Glu Gly Ser Lys Asp Pro Arg Gly
                165                 170                 175

Gly Ile Phe Asp Ala Val Phe Thr Arg Gly Asn Gln Ser Lys Leu Leu
            180                 185                 190

Thr Ser Arg His Asp Phe Lys Asn Lys Asn Leu Asn Asp Ile Ser Thr
            195                 200                 205

Ile Ile Lys Gln Glu Leu Thr Lys Gly Lys Ala Leu Gly Leu Ser His
        210                 215                 220

Thr Tyr Ala Asn Val Ser Ile Asn His Val Ile Asn Leu Trp Gly Ala
225                 230                 235                 240

Asp Phe Asn Ala Glu Gly Asn Leu Glu Ala Ile Tyr Val Thr Asp Ser
                245                 250                 255

Asp Ser Asn Ala Ser Ile Gly Met Lys Lys Tyr Phe Val Gly Val Asn
            260                 265                 270

Ala His Gly His Val Ala Ile Ser Ala Lys Lys Ile Glu Gly Glu Asn
            275                 280                 285

Ile Gly Ala Gln Val Leu Gly Leu Phe Thr Leu Ser Thr Gly Gln Asp
        290                 295                 300

Ser Trp Gln Lys Leu Ser
305                 310

<210> SEQ ID NO 26
<211> LENGTH: 320
<212> TYPE: PRT
<213> ORGANISM: Streptococcus pyogenes

<400> SEQUENCE: 26

Met Asp Ser Phe Ser Ala Asn Gln Glu Ile Arg Tyr Ser Glu Val Thr
1               5                   10                  15

Pro Tyr His Val Thr Ser Val Trp Thr Lys Gly Val Thr Pro Pro Ala
            20                  25                  30

Asn Phe Thr Gln Gly Glu Asp Val Phe His Ala Pro Tyr Val Ala Asn
        35                  40                  45

Gln Gly Trp Tyr Asp Ile Thr Lys Thr Phe Asn Gly Lys Asp Asp Leu
    50                  55                  60

Leu Cys Gly Ala Ala Thr Ala Gly Asn Met Leu His Trp Trp Phe Asp
65                  70                  75                  80

Gln Asn Lys Asp Gln Ile Lys Arg Tyr Leu Glu Glu His Pro Glu Lys
                85                  90                  95

Gln Lys Ile Asn Phe Asn Gly Glu Gln Met Phe Asp Val Lys Glu Ala
            100                 105                 110

Ile Asp Thr Lys Asn His Gln Leu Asp Ser Lys Leu Phe Glu Tyr Phe
        115                 120                 125

Lys Glu Lys Ala Phe Pro Tyr Leu Ser Thr Lys His Leu Gly Val Phe
130                 135                 140
```

```
Pro Asp His Val Ile Asp Met Phe Ile Asn Gly Tyr Arg Leu Ser Leu
145                 150                 155                 160

Thr Asn His Gly Pro Thr Pro Val Lys Glu Gly Ser Lys Asp Pro Arg
            165                 170                 175

Gly Gly Ile Phe Asp Ala Val Phe Thr Arg Gly Asp Gln Ser Lys Leu
            180                 185                 190

Leu Thr Ser Arg His Asp Phe Lys Glu Lys Asn Leu Lys Glu Ile Ser
            195                 200                 205

Asp Leu Ile Lys Lys Glu Leu Thr Glu Gly Lys Ala Leu Gly Leu Ser
            210                 215                 220

His Thr Tyr Ala Asn Val Arg Ile Asn His Val Ile Asn Leu Trp Gly
225                 230                 235                 240

Ala Asp Phe Asp Ser Asn Gly Asn Leu Lys Ala Ile Tyr Val Thr Asp
                245                 250                 255

Ser Asp Ser Asn Ala Ser Ile Gly Met Lys Lys Tyr Phe Val Gly Val
            260                 265                 270

Asn Ser Ala Gly Lys Val Ala Ile Ser Ala Lys Glu Ile Lys Glu Asp
            275                 280                 285

Asn Ile Gly Ala Gln Val Leu Gly Leu Phe Thr Leu Ser Thr Gly Gln
            290                 295                 300

Asp Ser Trp Asn Gln Thr Asn Gly Gly Gly His His His His His His
305                 310                 315                 320

<210> SEQ ID NO 27
<211> LENGTH: 325
<212> TYPE: PRT
<213> ORGANISM: Streptococcus pyogenes

<400> SEQUENCE: 27

Met Asp Asp Tyr Gln Arg Asn Ala Thr Glu Ala Tyr Ala Lys Glu Val
1               5                   10                  15

Pro His Gln Ile Thr Ser Val Trp Thr Lys Gly Val Thr Pro Leu Thr
            20                  25                  30

Pro Glu Gln Phe Arg Tyr Asn Asn Glu Asp Val Ile His Ala Pro Tyr
        35                  40                  45

Leu Ala His Gln Gly Trp Tyr Asp Ile Thr Lys Ala Phe Asp Gly Lys
    50                  55                  60

Asp Asn Leu Leu Cys Gly Ala Ala Thr Ala Gly Asn Met Leu His Trp
65                  70                  75                  80

Trp Phe Asp Gln Asn Lys Thr Glu Ile Glu Ala Tyr Leu Ser Lys His
                85                  90                  95

Pro Glu Lys Gln Lys Ile Ile Phe Asn Asn Gln Glu Leu Phe Asp Leu
            100                 105                 110

Lys Ala Ala Ile Asp Thr Lys Asp Ser Gln Thr Asn Ser Gln Leu Phe
        115                 120                 125

Asn Tyr Phe Arg Asp Lys Ala Phe Pro Asn Leu Ser Ala Arg Gln Leu
    130                 135                 140

Gly Val Met Pro Asp Leu Val Leu Asp Met Phe Ile Asn Gly Tyr Tyr
145                 150                 155                 160

Leu Asn Val Phe Lys Thr Gln Ser Thr Asp Val Asn Arg Pro Tyr Gln
                165                 170                 175

Asp Lys Asp Lys Arg Gly Gly Ile Phe Asp Ala Val Phe Thr Arg Gly
            180                 185                 190

Asp Gln Thr Thr Leu Leu Thr Ala Arg His Asp Leu Lys Asn Lys Gly
```

-continued

```
            195                 200                 205

Leu Asn Asp Ile Ser Thr Ile Ile Lys Gln Glu Leu Thr Glu Gly Arg
210                 215                 220

Ala Leu Ala Leu Ser His Thr Tyr Ala Asn Val Ser Ile Ser His Val
225                 230                 235                 240

Ile Asn Leu Trp Gly Ala Asp Phe Asn Ala Glu Gly Asn Leu Glu Ala
                    245                 250                 255

Ile Tyr Val Thr Asp Ser Asp Ala Asn Ala Ser Ile Gly Met Lys Lys
                260                 265                 270

Tyr Phe Val Gly Ile Asn Ala His Gly His Val Ala Ile Ser Ala Lys
                275                 280                 285

Lys Ile Glu Gly Glu Asn Ile Gly Ala Gln Val Leu Gly Leu Phe Thr
290                 295                 300

Leu Ser Ser Gly Lys Asp Ile Trp Gln Lys Leu Ser Gly Gly His
305                 310                 315                 320

His His His His His
                325

<210> SEQ ID NO 28
<211> LENGTH: 323
<212> TYPE: PRT
<213> ORGANISM: Streptococcus pyogenes

<400> SEQUENCE: 28

Met Asp Asp Tyr Gln Arg Asn Ala Thr Glu Ala Tyr Ala Lys Glu Val
1               5                   10                  15

Pro His Gln Ile Thr Ser Val Trp Thr Lys Gly Val Thr Pro Leu Thr
                20                  25                  30

Pro Glu Gln Phe Arg Tyr Asn Asn Glu Asp Val Phe His Ala Pro Tyr
            35                  40                  45

Val Ala Asn Gln Gly Trp Tyr Asp Ile Thr Lys Ala Phe Asp Gly Lys
        50                  55                  60

Asp Asn Leu Leu Cys Gly Ala Ala Thr Ala Gly Asn Met Leu His Trp
65                  70                  75                  80

Trp Phe Asp Gln Asn Lys Asp Gln Ile Lys Arg Tyr Leu Glu Glu His
                85                  90                  95

Pro Glu Lys Gln Lys Ile Asn Phe Asn Gly Asp Asn Met Phe Asp Val
            100                 105                 110

Lys Lys Ala Ile Asp Thr Lys Asn His Gln Leu Asp Ser Lys Leu Phe
        115                 120                 125

Asn Tyr Phe Lys Glu Lys Ala Phe Pro Gly Leu Ser Ala Arg Arg Ile
130                 135                 140

Gly Val Phe Pro Asp His Val Ile Asp Met Phe Ile Asn Gly Tyr Arg
145                 150                 155                 160

Leu Ser Leu Thr Asn His Gly Pro Thr Pro Val Lys Glu Gly Ser Lys
                165                 170                 175

Asp Pro Arg Gly Gly Ile Phe Asp Ala Val Phe Thr Arg Gly Asn Gln
            180                 185                 190

Ser Lys Leu Leu Thr Ser Arg His Asp Phe Lys Asn Lys Asn Leu Asn
        195                 200                 205

Asp Ile Ser Thr Ile Ile Lys Gln Glu Leu Thr Lys Gly Lys Ala Leu
210                 215                 220

Gly Leu Ser His Thr Tyr Ala Asn Val Ser Ile Asn His Val Ile Asn
225                 230                 235                 240
```

```
Leu Trp Gly Ala Asp Phe Asn Ala Glu Gly Asn Leu Glu Ala Ile Tyr
            245                 250                 255

Val Thr Asp Ser Asp Ser Asn Ala Ser Ile Gly Met Lys Lys Tyr Phe
        260                 265                 270

Val Gly Val Asn Ala His Gly His Val Ala Ile Ser Ala Lys Lys Ile
    275                 280                 285

Glu Gly Glu Asn Ile Gly Ala Gln Val Leu Gly Leu Phe Thr Leu Ser
290                 295                 300

Thr Gly Gln Asp Ser Trp Gln Lys Leu Ser Gly Gly His His His
305                 310                 315                 320

His His His

<210> SEQ ID NO 29
<211> LENGTH: 11
<212> TYPE: PRT
<213> ORGANISM: Streptococcus pyogenes

<400> SEQUENCE: 29

Pro Leu Thr Pro Glu Gln Phe Arg Tyr Asn Asn
1               5                   10

<210> SEQ ID NO 30
<211> LENGTH: 8
<212> TYPE: PRT
<213> ORGANISM: Streptococcus pyogenes

<400> SEQUENCE: 30

Pro Pro Ala Asn Phe Thr Gln Gly
1               5

<210> SEQ ID NO 31
<211> LENGTH: 20
<212> TYPE: PRT
<213> ORGANISM: Streptococcus pyogenes

<400> SEQUENCE: 31

Asp Asp Tyr Gln Arg Asn Ala Thr Glu Ala Tyr Ala Lys Glu Val Pro
1               5                   10                  15

His Gln Ile Thr
            20

<210> SEQ ID NO 32
<211> LENGTH: 20
<212> TYPE: PRT
<213> ORGANISM: Streptococcus pyogenes

<400> SEQUENCE: 32

Asp Ser Phe Ser Ala Asn Gln Glu Ile Arg Tyr Ser Glu Val Thr Pro
1               5                   10                  15

Tyr His Val Thr
            20

<210> SEQ ID NO 33
<211> LENGTH: 963
<212> TYPE: DNA
<213> ORGANISM: Streptococcus pyogenes

<400> SEQUENCE: 33
atggatagtt tttctgctaa tcaagagatt agatattcgg aagtaacacc ttatcacgtt     60
acttccgttt ggaccaaagg agttactcct ccagcaaact tcactcaagg tgaagatgtt    120
```

```
tttcacgctc cttatgttgc taaccaagga tggtatgata ttaccaaaac attcaatgga      180
aaagacgatc ttctttgcgg ggctgccaca gcagggaata tgcttcactg gtggttcgat      240
caaaacaaag accaaattaa acgttatttg aagagcatc cagaaaagca aaaataaac        300 ttcaatggcg aacagatgtt tgacgtaaaa gaagctatcg acactaaaaa ccaccagcta      360
gatagtaaat tatttgaata ttttaaagaa aaagctttcc cttatctatc tactaaacac      420
ctaggagttt tccctgatca tgtaattgat atgttcatta acggctaccg ccttagtcta     480
actaaccacg gtccaacgcc agtaaaagaa ggtagtaaag atccccgagg tggtattttt      540
gacgccgtat ttacaagagg tgatcaaagt aagctattga caagtcgtca tgattttaaa      600
gaaaaaaatc tcaaagaaat cagtgatctc attaagaaag agttaaccga aggcaaggct      660
ctaggcctat cacacaccta cgctaacgta cgcatcaacc atgttataaa cctgtgggga      720
gctgactttg attctaacgg gaaccttaaa gctatttatg taacagactc tgatagtaat      780
gcatctattg gtatgaagaa atactttgtt ggtgttaatt ccgctggaaa agtagctatt      840
tctgctaaag aaataaaaga agataatata ggtgctcaag tactagggtt atttacactt      900
tcaacagggc aagatagttg gaatcagacc aatggcggtg ccatcatca ccatcaccac      960 taa                                                                    963

<210> SEQ ID NO 34
<211> LENGTH: 978
<212> TYPE: DNA
<213> ORGANISM: Streptococcus pyogenes

<400> SEQUENCE: 34
atggacgatt accaaaggaa tgctacggaa gcttatgcca agaagtacc acatcagatc       60 acttctgtat ggaccaaagg tgttacacca ctaacacccg agcagtttcg atataataac      120
gaagatgtga tccatgcgcc atatcttgct catcaaggct ggtacgatat caccaaggcc      180
ttcgatggga aggataatct cttgtgtggc gcagcaacgg caggtaatat gctgcattgg      240
tggtttgatc aaaataaaac agagattgaa gcctatttaa gtaaacaccc tgaaaagcaa      300
aaaatcattt ttaacaacca agagctattt gatttgaaag ctgctatcga taccaaggac      360
agtcaaacca atagtcagct ttttaattat tttagagata aagccttttcc aaatctatca      420 gcacgtcaac tcggggttat gcctgatctt gttctagata tgtttatcaa tggttactac      480
ttaaatgtgt ttaaaacaca gtctactgat gtcaatcgac cttatcagga caaggacaaa      540
cgaggtggta ttttcgatgc tgttttcacc agaggagatc agacaacgct cttgacagct      600
cgtcatgatt taaaaaataa aggactaaat gacatcagca ccattatcaa gcaagaactg      660
actgaaggaa gagcccttgc tttatcacat acctacgcca atgttagcat tagccatgtg      720
attaacttgt ggggagctga ttttaatgct gaaggaaacc ttgaggccat ctatgtcaca      780
gactcagatg ctaatgcgtc tattggtatg aaaaaatatt ttgtcggcat taatgctcat      840
ggacatgtcg ccatttctgc caagaaaata gaaggagaaa acattggcgc tcaagtatta      900
ggcttattta cgctttccag tggcaaggac atttggcaga aactgagcgg cggtggccat      960
catcaccatc accactaa                                                    978

<210> SEQ ID NO 35
<211> LENGTH: 972
<212> TYPE: DNA
<213> ORGANISM: Streptococcus pyogenes

<400> SEQUENCE: 35
```

```
atggatgatt atcagcgcaa cgcgaccgaa gcgtatgcga aagaagtgcc gcatcagatt    60
accagcgtgt ggaccaaagg cgtgaccccg ctgaccccgg aacagtttcg ctataacaac   120
gaagatgtgt tcatgcgcc gtatgtggcg aaccagggct ggtatgatat taccaaagcg   180
tttgatggca aagataacct gctgtgcggc gcggcgaccg cgggcaacat gctgcattgg   240
tggtttgatc agaacaaaga tcagattaaa cgctatctgg aagaacatcc ggaaaaacag   300
aaaattaact ttaacggcga taacatgttt gatgtgaaaa agcgattga taccaaaaac   360
catcagctgg atagcaaact gtttaactat ttaaagaaa aagcgttcc gggcctgagc   420
gcgcgccgca ttggcgtgtt tccggatcat gtgattgata tgtttattaa cggctatcgc   480
ctgagcctga ccaaccatgg cccgaccccg gtgaagaag cagcaaaga tccgcgcggc   540
ggcattttg atgcggtgtt tacccgcggc aaccagagca aactgctgac cagccgccat   600
gattttaaaa acaaaaacct gaacgatatt agcaccatta ttaaacagga actgaccaaa   660
ggcaaagcgc tgggcctgag ccataccat gcgaacgtga gcattaacca tgtgattaac   720
ctgtggggcg cggattttaa cgcggaaggc aacctggaag cgatttatgt gaccgatagc   780
gatagcaacg cgagcattgg catgaaaaaa tattttgtgg gcgtgaacgc gcatggccat   840
gtggcgatta gcgcgaaaaa aattgaaggc gaaaacattg gcgcgcaggt gctgggcctg   900
tttaccctga gcaccggcca ggatagctgg cagaaactga gcggcggtgg ccatcatcac   960
catcaccact aa                                                      972

<210> SEQ ID NO 36
<211> LENGTH: 978
<212> TYPE: DNA
<213> ORGANISM: Streptococcus pyogenes

<400> SEQUENCE: 36
atggatgatt atcagcgcaa cgcgaccgaa gcgtatgcga aagaagtgcc gcatcagatt    60
accagcgtgt ggaccaaagg cgtgaccccg ctgaccccgg aacagtttcg ctataacaac   120
gaagatgtga ttcatgcgcc gtatctggcg aaccagggct ggtatgatat taccaaagcg   180
tttgatggca aagataacct gctgtgcggc gcggcgaccg cgggcaacat gctgcattgg   240
tggtttgatc agaacaaaac cgaaattgaa gcgtatctga gcaaacatcc ggaaaaacag   300
aaaattattt ttcgcaacca ggaactgttt gatctgaaag aagcgattcg caccaaagat   360
agccagacca acagccagct gtttgaatat tttcgcgata aagcgttcc gtatctgagc   420
gcgcgccagc tgggcgtgat gccggatctg gtgctggata tgtttattaa cggctattat   480
ctgaacgtgt ttaaaaccca gagcaccgat gtgaaacgcc cgtatcagga taaagataaa   540
cgcggcggca ttttgatgc ggtgtttacc cgcggcaacc agaccaccct gctgaccgcg   600
cgccatgatc tgaaaaacaa aggcctgaac gatattagca ccattattaa agaagaactg   660
accaaaggcc gcgcgctggc gctgagccat acctatgcga acgtgagcat tagccatgtg   720
attaacctgt ggggcgcgga ttttaacgcg gaaggcaacc tggaagcgat ttatgtgacc   780
gatagcgatg cgaacgcgag cattggcatg aaaaatatt ttgtgggcat taacaaacat   840
ggccatgtgg cgattagcgc gaaaaaaatt gaaggcgaaa acattggcgc gcaggtgctg   900
ggcctgttta cccctgagcag cggcaaagat atttggcaga aactgaacgg cggtggccat   960
catcaccatc accactaa                                                978

<210> SEQ ID NO 37
```

```
<211> LENGTH: 978
<212> TYPE: DNA
<213> ORGANISM: Streptococcus pyogenes

<400> SEQUENCE: 37
atggatgatt atcagcgcaa cgcgaccgaa gcgtatgcga aagaagtgcc gcatcagatt      60
accagcgtgt ggaccaaagg cgtgaccccg ctgaccccgg aacagtttcg ctataacaac     120
gaagatgtga ttcatgcgcc gtatctggcg catcagggct ggtatgatat taccaaaacc     180
tttaacggca aagataacct gctgtgcggc gcggcgaccg cgggcaacat gctgcattgg     240
tggtttgatc agaacaaaac cgaaattgaa gcgtatctga gcaaacatcc ggaaaaacag     300
aaaattattt taacaacga gaactgtttt gatctgaaag cggcgattga taccaaagat     360
agccagacca acagccagct gtttaactat tttaaagaaa aagcgtttcc gaacctgagc     420
acccgccagc tgggcgtgat gccggatctg gtgctggata tgtttattaa cggctattat     480
ctgaacgtgt ttaaacccca gagcaccgat gtgaaccgcc cgtatcagga taaagataaa     540
cgcggcggca tttttgatgc ggtgtttacc cgcggcaacc agaccaccct gctgaccgcg     600
cgccatgatt ttaaagaaaa aggcctgaaa gatattagca ccattattaa acaggaactg     660
accgaaggcc gcgcgctggc gctgagccat acctatgcga acgtgagcat tagccatgtg     720
attaacctgt ggggcgcgga ttttgatgcg gaaggcaacc tgaaagcgat ttatgtgacc     780
gatagcgatg cgaacgcgag cattggcatg aaaaaaatatt ttgtgggcat taacgcgcat     840
ggcaaagtgg cgattagcgc gaaaaaaatt gaaggcgaaa acattggcgc gcaggtgctg     900
ggcctgttta ccctgagcag cggcaaagat atttggcagc agctgagcgg cggtggccat     960
catcaccatc accactaa                                                  978

<210> SEQ ID NO 38
<211> LENGTH: 978
<212> TYPE: DNA
<213> ORGANISM: Streptococcus pyogenes

<400> SEQUENCE: 38
atggatagct ttagcgcgaa ccaggaaatt cgctatagcg aagtgacccc gtatcatgtg      60
accagcgtgt ggaccaaagg cgtgaccccg ctgaccccgg aacagtttcg ctataacaac     120
gaagatgtga ttcatgcgcc gtatctggcg catcagggct ggtatgatat taccaaagcg     180
tttgatggca aagataacct gctgtgcggc gcggcgaccg cgggcaacat gctgcattgg     240
tggtttgatc agaacaaaac cgaaattgaa gcgtatctga gcaaacatcc ggaaaaacag     300
aaaattattt taacaacca ggaactgttt gatctgaaag cggcgattga taccaaagat     360
agccagacca acagccagct gtttaactat tttcgcgata aagcgtttcc gaacctgagc     420
gcgcgccagc tgggcgtgat gccggatctg gtgctggata tgtttattaa cggctattat     480
ctgaacgtgt ttaaacccca gagcaccgat gtgaaccgcc cgtatcagga taaagataaa     540
cgcggcggca tttttgatgc ggtgtttacc cgcggcgatc agaccaccct gctgaccgcg     600
cgccatgatc tgaaaaacaa aggcctgaac gatattagca ccattattaa acaggaactg     660
accgaaggcc gcgcgctggc gctgagccat acctatgcga acgtgagcat tagccatgtg     720
attaacctgt ggggcgcgga ttttaacgcg gaaggcaacc tggaagcgat ttatgtgacc     780
gatagcgatg cgaacgcgag cattggcatg aaaaaaatatt ttgtgggcat taacgcgcat     840
ggccatgtgg cgattagcgc gaaaaaaatt gaaggcgaaa acattggcgc gcaggtgctg     900
ggcctgttta ccctgagcag cggcaaagat atttggcaga aactgagcgg cggtggccat     960
```

| | |
|---|---|
| catcaccatc accactaa | 978 |

<210> SEQ ID NO 39
<211> LENGTH: 918
<212> TYPE: DNA
<213> ORGANISM: Streptococcus pyogenes

<400> SEQUENCE: 39

| | |
|---|---|
| atgagcgtgt ggaccaaagg cgtgaccccg ctgaccccgg aacagtttcg ctataacaac | 60 |
| gaagatgtga ttcatgcgcc gtatctggcg catcagggct ggtatgatat taccaaagcg | 120 |
| tttgatggca agataacct gctgtgcggc gcggcgaccg cgggcaacat gctgcattgg | 180 |
| tggtttgatc agaacaaaac cgaaattgaa gcgtatctga gcaaacatcc ggaaaaacag | 240 |
| aaaattattt ttaacaacca ggaactgttt gatctgaaag cggcgattga taccaaagat | 300 |
| agccagacca cagccagct gtttaactat tttcgcgata aagcgttttcc gaacctgagc | 360 |
| gcgcgccagc tgggcgtgat gccggatctg gtgctggata tgtttattaa cggctattat | 420 |
| ctgaacgtgt ttaaaaccca gagcaccgat gtgaaccgcc cgtatcagga taaagataaa | 480 |
| cgcggcggca tttttgatgc ggtgtttacc cgcggcgatc agaccaccct gctgaccgcg | 540 |
| cgccatgatc tgaaaaacaa aggcctgaac gatattagca ccattattaa acaggaactg | 600 |
| accgaaggcc gcgcgctggc gctgagccat acctatgcga acgtgagcat agccatgtg | 660 |
| attaacctgt ggggcgcgga ttttaacgcg gaaggcaacc tggaagcgat ttatgtgacc | 720 |
| gatagcgatg cgaacgcgag cattggcatg aaaaaaatatt ttgtgggcat taacgcgcat | 780 |
| ggccatgtgg cgattagcgc gaaaaaaatt gaaggcgaaa acattggcgc gcaggtgctg | 840 |
| ggcctgttta ccctgagcag cggcaaagat atttggcaga aactgagcgg cggtggccat | 900 |
| catcaccatc accactaa | 918 |

<210> SEQ ID NO 40
<211> LENGTH: 975
<212> TYPE: DNA
<213> ORGANISM: Streptococcus pyogenes

<400> SEQUENCE: 40

| | |
|---|---|
| atggacgatt accaaaggaa tgctacggaa gcttatgcca agaagtacc acatcagatc | 60 |
| acttctgtat ggaccaaagg tgttacacca ctaacacccg agcagtttac tcaaggtgaa | 120 |
| gatgtgatcc atgcgccata tcttgctcat caaggctggt acgatatcac caaggccttc | 180 |
| gatgggaagg ataatctctt gtgtggcgca gcaacggcag gtaatatgct gcattggtgg | 240 |
| tttgatcaaa ataaaacaga gattgaagcc tatttaagta acaccctga aaagcaaaaa | 300 |
| atcatttta acaaccaaga gctatttgat ttgaaagctg ctatcgatac caaggacagt | 360 |
| caaaccaata gtcagctttt taattatttt agagataaag cctttccaaa tctatcagca | 420 |
| cgtcaactcg gggttatgcc tgatcttgtt ctagatatgt ttatcaatgg ttactactta | 480 |
| aatgtgttta aaacacagtc tactgatgtc aatcgacctt atcaggacaa ggacaaacga | 540 |
| ggtggtattt tcgatgctgt tttcaccaga ggagatcaga caacgctctt gacagctcgt | 600 |
| catgatttaa aaaataaagg actaaatgac atcagcacca ttatcaagca agaactgact | 660 |
| gaaggaagag cccttgcttt atcacatacc tacgccaatg ttagcattag ccatgtgatt | 720 |
| aacttgtggg gagctgattt taatgctgaa ggaaaccttg aggccatcta tgtcacagac | 780 |
| tcagatgcta atgcgtctat tggtatgaaa aaatattttg tcggcattaa tgctcatgga | 840 |

| | | |
|---|---|---|
| catgtcgcca tttctgccaa gaaaatagaa ggagaaaaca ttggcgctca agtattaggc | | 900 |
| ttatttacgc tttccagtgg caaggacatt tggcagaaac tgagcggcgg tggccatcat | | 960 |
| caccatcacc actaa | | 975 |

<210> SEQ ID NO 41
<211> LENGTH: 969
<212> TYPE: DNA
<213> ORGANISM: Streptococcus pyogenes

<400> SEQUENCE: 41

| | | |
|---|---|---|
| atggacgatt accaaaggaa tgctacggaa gcttatgcca agaagtacc acatcagatc | | 60 |
| acttctgtat ggaccaaagg tgttacacca cccgagcagt ttactcaagg tgaagatgtg | | 120 |
| atccatgcgc catatcttgc tcatcaaggc tggtacgata tcaccaaggc cttcgatggg | | 180 |
| aaggataatc tcttgtgtgg cgcagcaacg gcaggtaata tgctgcattg gtggtttgat | | 240 |
| caaaataaaa cagagattga agcctattta agtaaacacc ctgaaaagca aaaaatcatt | | 300 |
| tttaacaacc aagagctatt tgatttgaaa gctgctatcg ataccaagga cagtcaaacc | | 360 |
| aatagtcagc ttttaatta ttttagagat aaagcctttc caaatctatc agcacgtcaa | | 420 |
| ctcggggtta tgcctgatct tgttctagat atgtttatca tggttacta cttaaatgtg | | 480 |
| tttaaaacac agtctactga tgtcaatcga ccttatcagg acaaggacaa acgaggtggt | | 540 |
| attttcgatg ctgttttcac cagaggagat cagacaacgc tcttgacagc tcgtcatgat | | 600 |
| ttaaaaaata aaggactaaa tgacatcagc accattatca gcaagaact gactgaagga | | 660 |
| agagcccttg cttatcaca tacctacgcc aatgttagca ttagccatgt gattaacttg | | 720 |
| tggggagctg attttaatgc tgaaggaaac cttgaggcca tctatgtcac agactcagat | | 780 |
| gctaatgcgt ctattggtat gaaaaaatat tttgtcggca ttaatgctca tggacatgtc | | 840 |
| gccatttctg ccagaaaat agaaggagaa acattggcg ctcaagtatt aggcttattt | | 900 |
| acgctttcca gtggcaagga catttggcag aaactgagcg gcggtggcca tcatccat | | 960 |
| caccactaa | | 969 |

<210> SEQ ID NO 42
<211> LENGTH: 972
<212> TYPE: DNA
<213> ORGANISM: Streptococcus pyogenes

<400> SEQUENCE: 42

| | | |
|---|---|---|
| atggacgatt accaaaggaa tgctacggaa gcttatgcca agaagtacc acatcagatc | | 60 |
| acttctgtat ggaccaaagg tgttacacca cccgagcagt ttcgatataa taacgaagat | | 120 |
| gtgatccatg cgccatatct tgctcatcaa ggctggtacg atatcaccaa ggccttcgat | | 180 |
| gggaaggata atctcttgtg tggcgcagca acggcaggta atatgctgca ttggtggttt | | 240 |
| gatcaaaata aaacagagat tgaagcctat ttaagtaaac ccctgaaaa gcaaaaaatc | | 300 |
| atttttaaca accaagagct atttgatttg aaagctgcta tcgataccaa ggacagtcaa | | 360 |
| accaatagtc agcttttaa ttattttaga gataaagcct ttccaaatct atcagcacgt | | 420 |
| caactcgggg ttatgcctga tcttgttcta gatatgttta tcaatggtta ctacttaaat | | 480 |
| gtgtttaaaa cacagtctac tgatgtcaat cgaccttatc aggacaagga caaacgaggt | | 540 |
| ggtattttcg atgctgtttt caccagagga gatcagacaa cgctcttgac agctcgtcat | | 600 |
| gatttaaaaa ataaaggact aaatgacatc agcaccatta tcaagcaaga actgactgaa | | 660 |
| ggaagagccc ttgctttatc acatacctac gccaatgtta gcattagcca tgtgattaac | | 720 |

```
ttgtggggag ctgatttaa tgctgaagga aaccttgagg ccatctatgt cacagactca    780
gatgctaatg cgtctattgg tatgaaaaaa tattttgtcg gcattaatgc tcatggacat    840
gtcgccattt ctgccaagaa aatagaagga gaaaacattg gcgctcaagt attaggctta    900
tttacgcttt ccagtggcaa ggacatttgg cagaaactga gcggcggtgg ccatcatcac    960
catcaccact aa                                                         972
```

<210> SEQ ID NO 43
<211> LENGTH: 969
<212> TYPE: DNA
<213> ORGANISM: Streptococcus pyogenes

<400> SEQUENCE: 43

```
atggacgatt accaaaggaa tgctacggaa gcttatgcca agaagtacc acatcagatc     60 acttctgtat ggaccaaagg tgttacacca cccgagcagt ttactcaagg tgaagatgtg    120
atccatgcgc catatcttgc tcatcaaggc tggtacgata tcaccaaggc cttcgatggg    180
aaggataatc tcttgtgtgg cgcagcaacg gcaggtaata tgctgcattg gtggtttgat    240
caaaataaaa cagagattga agcctattta agtaaacacc ctgaaaagca aaaaatcatt    300
attaacaacc aagagctatt tgatttgaaa gctgctatcg ataccaagga cagtcaaacc    360
aatagtcagc tttttaatta ttttagagat aaagcctttc caaatctatc agcacgtcaa    420
ctcggggtta tgcctgatct tgttctagat atgtttatca atggttacta cttaaatgtg    480
tttaaaacac agtctactga tgtcaatcga cctttatcagg acaaggacaa acgaggtggt    540
attttcgatg ctgttttcac cagaggagat cagacaacgc tcttgacagc tcgtcatgat    600
ttaaaaaata aaggactaaa tgacatcagc accattatca gcaagaact gactgaagga    660 agagcccttg ctttatcaca tacctacgcc aatgttagca ttagccatgt gattaacttg    720
tggggagctg atttaatgc tgaaggaaac cttgaggcca tctatgtcac agactcagat    780
gctaatgcgt ctattggtat gaaaaaatat tttgtcggca ttaatgctca tggacatgtc    840 gccattctg ccaagaaaat agaaggagaa aacattggcg ctcaagtatt aggcttattt    900
acgctttcca gtggcaagga catttggcag aaactgagcg cggtggcca tcatcaccat    960 caccactaa                                                             969
```

<210> SEQ ID NO 44
<211> LENGTH: 969
<212> TYPE: DNA
<213> ORGANISM: Streptococcus pyogenes

<400> SEQUENCE: 44

```
atggacgatt accaaaggaa tgctacggaa gcttatgcca agaagtacc acatcagatc     60 acttctgtat ggaccaaagg tgttacacca cccgagcagt ttactcaagg tgaagatgtg    120
atccatgcgc catatcttgc tcatcaaggc tggtacgata tcaccaaggc cttcgatggg    180
aaggataatc tcttgtgtgg cgcagcaacg gcaggtaata tgctgcattg gtggtttgat    240
caaaataaaa cagagattga agcctattta agtaaacacc ctgaaaagca aaaaatcatt    300
tttcgtaacc aagagctatt tgatttgaaa gctgctatcg ataccaagga cagtcaaacc    360
aatagtcagc tttttaatta ttttagagat aaagcctttc caaatctatc agcacgtcaa    420
ctcggggtta tgcctgatct tgttctagat atgtttatca atggttacta cttaaatgtg    480
tttaaaacac agtctactga tgtcaatcga cctttatcagg acaaggacaa acgaggtggt    540
```

```
attttcgatg ctgttttcac cagaggagat cagacaacgc tcttgacagc tcgtcatgat    600
ttaaaaaata aaggactaaa tgacatcagc accattatca agcaagaact gactgaagga    660
agagcccttg ctttatcaca tacctacgcc aatgttagca ttagccatgt gattaacttg    720
tggggagctg attttaatgc tgaaggaaac cttgaggcca tctatgtcac agactcagat    780
gctaatgcgt ctattggtat gaaaaaatat tttgtcggca ttaatgctca tggacatgtc    840
gccatttctg ccaagaaaat agaaggagaa aacattggcg ctcaagtatt aggcttattt    900
acgctttcca gtggcaagga catttggcag aaactgagcg gcggtggcca tcatcaccat    960
caccactaa                                                            969
```

<210> SEQ ID NO 45
<211> LENGTH: 969
<212> TYPE: DNA
<213> ORGANISM: Streptococcus pyogenes

<400> SEQUENCE: 45

```
atggacgatt accaaaggaa tgctacggaa gcttatgcca agaagtacc acatcagatc      60 acttctgtat ggaccaaagg tgttacacca cccgagcagt ttactcaagg tgaagatgtg    120
atccatgcgc catatcttgc tcatcaaggc tggtacgata tcaccaaggc cttcgatggg    180
aaggataatc tcttgtgtgg cgcagcaacg gcaggtaata tgctgcattg gtggtttgat    240
caaaataaaa cagagattga agcctattta agtaaacacc ctgaaaagca aaaaatcatt    300
attcgtaacc aagagctatt tgatttgaaa gctgctatcg ataccaagga cagtcaaacc    360
aatagtcagc tttttaatta ttttagagat aaagcctttc caaatctatc agcacgtcaa    420
ctcggggtta tgcctgatct tgttctagat atgtttatca atggttacta cttaaatgtg    480
tttaaaacac agtctactga tgtcaatcga ccttatcagg acaaggacaa acgaggtggt    540
attttcgatg ctgttttcac cagaggagat cagacaacgc tcttgacagc tcgtcatgat    600
ttaaaaaata aaggactaaa tgacatcagc accattatca agcaagaact gactgaagga    660
agagcccttg ctttatcaca tacctacgcc aatgttagca ttagccatgt gattaacttg    720
tggggagctg attttaatgc tgaaggaaac cttgaggcca tctatgtcac agactcagat    780
gctaatgcgt ctattggtat gaaaaaatat tttgtcggca ttaatgctca tggacatgtc    840
gccatttctg ccaagaaaat agaaggagaa aacattggcg ctcaagtatt aggcttattt    900
acgctttcca gtggcaagga catttggcag aaactgagcg gcggtggcca tcatcaccat    960
caccactaa                                                            969
```

<210> SEQ ID NO 46
<211> LENGTH: 969
<212> TYPE: DNA
<213> ORGANISM: Streptococcus pyogenes

<400> SEQUENCE: 46

```
atggatgatt atcagcgcaa cgcgaccgaa gcgtatgcga agaagtgcc gcatcagatt      60 accagcgtgt ggaccaaagg cgtgaccccg ccggaacagt ttactcaagg tgaagatgtg    120
attcatgcgc cgtatctggc gaaccagggc tggtatgata ttaccaaagc gtttgatggc    180
aaagataacc tgctgtgcgg cgcggcgacc gcgggcaaca tgctgcattg gtggtttgat    240
cagaacaaaa ccgaaattga agcgtatctg agcaaacatc cggaaaaaca gaaaattatt    300
tttcgcaacc aggaactgtt tgatctgaaa gaagcgattg caccaaagda tagccagacc    360
aacagccagc tgtttgaata ttttcgcgat aaagcgtttc cgtatctgag cgcgcgccag    420
```

```
ctgggcgtga tgccggatct ggtgctggat atgtttatta acggctatta tctgaacgtg    480
tttaaaaccc agagcaccga tgtgaaacgc ccgtatcagg ataaagataa acgcggcggc    540 attttttgatg cggtgtttac ccgcggcaac cagaccaccc tgctgaccgc gcgccatgat    600
ctgaaaaaca aaggcctgaa cgatattagc accattatta agaagaact gaccaaaggc    660 cgcgcgctgg cgctgagcca tacctatgcg aacgtgagca ttagccatgt gattaacctg    720
tggggcgcgg attttaacgc ggaaggcaac ctggaagcga tttatgtgac cgatagcgat    780
gcgaacgcga gcattggcat gaaaaaatat tttgtgggca ttaacaaaca tggccatgtg    840
gcgattagcg cgaaaaaaat tgaaggcgaa acattggcg cgcaggtgct gggcctgttt    900
accctgagca gcggcaaaga tatttggcag aaactgaacg gcggtggcca tcatcaccat    960
caccactaa    969

<210> SEQ ID NO 47
<211> LENGTH: 909
<212> TYPE: DNA
<213> ORGANISM: Streptococcus pyogenes

<400> SEQUENCE: 47
atgtctgtat ggaccaaagg tgttacacca cccgagcagt ttactcaagg tgaagatgtg     60
atccatgcgc catatcttgc tcatcaaggc tggtacgata tcaccaaggc cttcgatggg    120
aaggataatc tcttgtgtgg cgcagcaacg gcaggtaata tgctgcattg gtggtttgat    180
caaaataaaa cagagattga agcctattta agtaaacacc ctgaaaagca aaaaatcatt    240
tttcgtaacc aagagctatt tgatttgaaa gctgctatcg ataccaagga cagtcaaacc    300
aatagtcagc tttttaatta ttttagagat aaagcctttc caaatctatc agcacgtcaa    360
ctcggggtta tgcctgatct tgttctagat atgtttatca atggttacta cttaaatgtg    420
tttaaaacac agtctactga tgtcaatcga ccttatcagg acaaggacaa acgaggtggt    480
attttcgatg ctgttttcac cagaggaaac cagacaacgc tcttgacagc tcgtcatgat    540
ttaaaaaata aaggactaaa tgacatcagc accattatca gcaagaact gactgaagga    600 agagcccttg ctttatcaca tacctacgcc aatgttagca ttagccatgt gattaacttg    660
tggggagctg attttaatgc tgaaggaaac cttgaggcca tctatgtcac agactcagat    720
gctaatgcgt ctattggtat gaaaaaatat tttgtcggca ttaatgctca tggacatgtc    780
gccatttctg ccaagaaaat agaaggagaa acattggcg ctcaagtatt aggcttattt    840
acgctttcca gtggcaagga catttggcag aaactgagcg gcggtggcca tcatcaccat    900
caccactaa    909

<210> SEQ ID NO 48
<211> LENGTH: 969
<212> TYPE: DNA
<213> ORGANISM: Streptococcus pyogenes

<400> SEQUENCE: 48
atggacgatt accaaaggaa tgctacggaa gcttatgcca agaagtacc acatcagatc      60 acttctgtat ggaccaaagg tgttacacca cccgagcagt ttactcaagg tgaagatgtg    120
atccatgcgc catatcttgc tcatcaaggc tggtacgata tcaccaaggc cttcgatggg    180
gcggataatc tcttgtgtgg cgcagcaacg gcaggtaata tgctgcattg gtggtttgat    240
caaaataaaa cagagattga agcctattta agtaaacacc ctgaaaagca aaaaatcatt    300
```

```
tttcgtaacc aagagctatt tgatttgaaa gctgctatcg ataccaagga cagtcaaacc      360
aatagtcagc ttttaatta ttttagagat aaagcctttc caaatctatc agcacgtcaa      420
ctcggggtta tgcctgatct tgttctagat atgtttatca atggttacta cttaaatgtg      480
tttaaaacac agtctactga tgtcaatcga ccttatcagg acaaggacaa acgaggtggt      540
attttcgatg ctgttttcac cagaggaaat cagacaacgc tcttgacagc tcgtcatgat      600
ttaaaaaata aaggactaaa tgacatcagc accattatca agcaagaact gactgaagga      660
agagcccttg ctttatcaca tacctacgcc aatgttagca ttagccatgt gattaacttg      720
tggggagctg attttaatgc tgaaggaaac cttgaggcca tctatgtcac agactcagat      780
gctaatgcgt ctattggtat gaaaaaatat tttgtcggca ttaatgctca tggacatgtc      840 gccattctg ccaagaaaat agaaggagaa acattggcg ctcaagtatt aggcttattt      900
acgctttcca gtggcaagga catttggcag aaactgagcg gcggtggcca tcatcaccat      960
caccactaa                                                             969

<210> SEQ ID NO 49
<211> LENGTH: 909
<212> TYPE: DNA
<213> ORGANISM: Streptococcus pyogenes

<400> SEQUENCE: 49
atgtctgtat ggaccaaagg tgttacacca cccgagcagt ttactcaagg tgaagatgtg       60
atccatgcgc catatcttgc tcatcaaggc tggtacgata tcaccaaggc cttcgatggg      120
gcggataatc tcttgtgtgg cgcagcaacg gcaggtaata tgctgcattg gtggtttgat      180
caaaataaaa cagagattga agcctattta agtaaacacc ctgaaaagca aaaaatcatt      240
tttcgtaacc aagagctatt tgatttgaaa gctgctatcg ataccaagga cagtcaaacc      300
aatagtcagc ttttaatta ttttagagat aaagcctttc caaatctatc agcacgtcaa      360
ctcggggtta tgcctgatct tgttctagat atgtttatca atggttacta cttaaatgtg      420
tttaaaacac agtctactga tgtcaatcga ccttatcagg acaaggacaa acgaggtggt      480
attttcgatg ctgttttcac cagaggaaat cagacaacgc tcttgacagc tcgtcatgat      540
ttaaaaaata aaggactaaa tgacatcagc accattatca agcaagaact gactgaagga      600
agagcccttg ctttatcaca tacctacgcc aatgttagca ttagccatgt gattaacttg      660
tggggagctg attttaatgc tgaaggaaac cttgaggcca tctatgtcac agactcagat      720
gctaatgcgt ctattggtat gaaaaaatat tttgtcggca ttaatgctca tggacatgtc      780 gccattctg ccaagaaaat agaaggagaa acattggcg ctcaagtatt aggcttattt      840
acgctttcca gtggcaagga catttggcag aaactgagcg gcggtggcca tcatcaccat      900
caccactaa                                                             909

<210> SEQ ID NO 50
<211> LENGTH: 969
<212> TYPE: DNA
<213> ORGANISM: Streptococcus pyogenes

<400> SEQUENCE: 50
atggacgatt accaaaggaa tgctacggaa gcttatgcca agaagtacc acatcagatc       60 acttctgtat ggaccaaagg tgttacacca cccgagcagt ttactcaagg tgaagatgtg      120
atccatgcgc catatcttgc tcatcaaggc tggtacgata tcaccaaggc cttcgatggg      180
aaggataatc tcttgtgtgg cgcagcaacg gcaggtaata tgctgcattg gtggtttgat      240
```

```
caaaataaaa cagagattga agcctatttta agtaaacacc ctgaaaagca aaaaatcatt    300
tttcgtaacc aagagctatt tgatttgaaa gctgctatcg ataccaagga cagtcaaacc    360
aatagtcagc tttttaatta ttttagagat aaagcctttc caaatctatc agcacgtcaa    420
ctcggggtta tgcctgatct tgttctagat atgtttatca atggttacta cttaaatgtg    480
tttaaaacac agtctactga tgtcaatcga ccttatcagg acaaggacaa acgaggtggt    540
attttcgatg ctgttttcac cagaggaaac cagacaacgc tcttgacagc tcgtcatgat    600
ttaaaaaata aaggactaaa tgacatcagc accattatca agcaagaact gactgaagga    660
agagcccttg ctttatcaca tacctacgcc aatgttagca ttagccatgt gattaacttg    720
tggggagctg attttaatgc tgaaggaaac cttgaggcca tctatgtcac agactcagat    780
gctaatgcgt ctattggtat gaaaaaatat tttgtcggca ttaatgctca tggacatgtc    840
gccatttctg ccaagaaaat agaaggagaa acattggcg ctcaagtatt aggcttattt    900
acgctttcca gtggcaagga catttggcag aaactgagcg gcggtggcca tcatcaccat    960
caccactaa                                                            969

<210> SEQ ID NO 51
<211> LENGTH: 969
<212> TYPE: DNA
<213> ORGANISM: Streptococcus pyogenes

<400> SEQUENCE: 51
atggatgatt atcagcgcaa cgcgaccgaa gcgtatgcga aagaagtgcc gcatcagatt     60
accagcgtgt ggaccaaagg cgtgaccccg ctgaccccgg aacagtttac ccagggcgaa    120
gatgtgtttc atgcgccgta tgtggcgaac cagggctggt atgatattac caaagcgttt    180
gatggcaaag ataacctgct gtgcggcgcg gcgaccgcgg caacatgct gcattggtgg    240 tttgatcaga caaagatca gattaaacgc tatctggaag aacatccgga aaaacagaaa    300
attaacttta acggcgaaaa catgtttgat gtgaaaaaag cgattgatac caaaaaccat    360
cagctggata gcaaactgtt taactatttt aaagaaaaag cgtttccgta tctgagcgcg    420
aaacatctgg gcgtgttttcc ggatcatgtg attgatatgt ttattaacgg ctatcgcctg    480
agcctgacca ccatggccc gaccccggtg aaagaaggca gcaaagatcc gcgcggcggc    540 attttgatg cggtgtttac ccgcggcaac cagagcaaac tgctgaccag ccgccatgat    600
tttaaaaaca aaaacctgaa cgatattagc accattatta acaggaact gaccaaaggc    660 aaagcgctgg gcctgagcca tacctatgcg aacgtgcgca ttaaccatgt gattaacctg    720
tggggcgcgg attttaacgc ggaaggcaac ctggaagcga tttatgtgac cgatagcgat    780
agcaacgcga gcattggcat gaaaaaatat tttgtgggcg tgaacgcgca tggccatgtg    840
gcgattagcg cgaaaaaaat tgaaggcgaa acattggcg cgcaggtgct gggcctgttt    900
accctgagca ccggccagga tagctggcag aaactgagcg gcggtggcca tcatcaccat    960
caccactaa                                                            969

<210> SEQ ID NO 52
<211> LENGTH: 969
<212> TYPE: DNA
<213> ORGANISM: Streptococcus pyogenes

<400> SEQUENCE: 52
atggatgatt atcagcgcaa cgcgaccgaa gcgtatgcga aagaagtgcc gcatcagatt     60
```

| | |
|---|---|
| accagcgtgt ggaccaaagg cgtgaccccg ctgaccccgg aacagtttac ccagggcgaa | 120 |
| gatgtgtttc atgcgccgta tgtggcgaac cagggctggt atgatattac caaagcgttt | 180 |
| gatggcaaag ataacctgct gtgcggcgcg gcgaccgcgg caacatgct gcattggtgg | 240 |
| tttgatcaga acaaagatca gattaaacgc tatctggaag aacatccgga aaaacagaaa | 300 |
| attaactttc gcggcgaaaa catgtttgat gtgaaagaag cgattcgcac caaaaaccat | 360 |
| cagctggata gcaaactgtt tgaatatttt aaagaaaaag cgtttccgta tctgagcgcg | 420 |
| aaacatctgg gcgtgtttcc ggatcatgtg attgatatgt ttattaacgg ctatcgcctg | 480 |
| agcctgacca accatggccc gaccccggtg aaaaaaggca gcaaagatcc gcgcggcggc | 540 |
| attttgatg cggtgtttac ccgcggcaac cagagcaaac tgctgaccag ccgccatgat | 600 |
| tttaaaaaca aaaaccctga acgatattagc accattatta aaagcgaact gaccaacggc | 660 |
| aaagcgctgg gcctgagcca tacctatgcg aacgtgcgca ttaaccatgt gattaacctg | 720 |
| tggggcgcgg attttaacgc ggaaggcaac ctggaagcga tttatgtgac cgatagcgat | 780 |
| agcaacgcga gcattggcat gaaaaaatat tttgtgggcg tgaacaaaca tggccatgtg | 840 |
| gcgattagcg cgaaaaaaat tgaaggcgaa acattggcg cgcaggtgct gggcctgttt | 900 |
| accctgagca ccggccagga tagctggcag aaaactgaacg gcggtggcca tcatcaccat | 960 |
| caccactaa | 969 |

<210> SEQ ID NO 53
<211> LENGTH: 969
<212> TYPE: DNA
<213> ORGANISM: Streptococcus pyogenes

<400> SEQUENCE: 53

| | |
|---|---|
| atggatgatt atcagcgcaa cgcgaccgaa gcgtatgcga agaagtgcc gcatcagatt | 60 |
| accagcgtgt ggaccaaagg cgtgaccccg ctgaccccgg aacagtttac ccagggcgaa | 120 |
| gatgtgtttc atgcgccgta tgtggcgaac cagggctggt atgatattac caaaccttt | 180 |
| aacggcaaag atgatctgct gtgcggcgcg gcgaccgcgg caacatgct gcattggtgg | 240 |
| tttgatcaga acaaagatca gattaaacgc tatctggaag aacatccgga aaaacagaaa | 300 |
| attaacttta cggcgaaca gatgtttgat gtgaaagaag cgattgatac caaaaaccat | 360 |
| cagctggata gcaaactgtt tgaatatttt aaagaaaaag cgtttccgta tctgagcacc | 420 |
| aaacatctgg gcgtgtttcc ggatcatgtg attgatatgt ttattaacgg ctatcgcctg | 480 |
| agcctgacca accatggccc gaccccggtg aagaaaggca gcaaagatcc gcgcggcggc | 540 |
| attttgatg cggtgtttac ccgcggcaac cagagcaaac tgctgaccag ccgccatgat | 600 |
| tttaaagaaa aaaacctgaa agaaattagc gatctgatta acaggaact gaccgaaggc | 660 |
| aaagcgctgg gcctgagcca tacctatgcg aacgtgcgca ttaaccatgt gattaacctg | 720 |
| tggggcgcgg attttgatgc ggaaggcaac ctgaaagcga tttatgtgac cgatagcgat | 780 |
| agcaacgcga gcattggcat gaaaaaatat tttgtgggcg tgaacgcggc gggcaaagtg | 840 |
| gcgattagcg cgaaaaaaat tgaaggcgaa acattggcg cgcaggtgct gggcctgttt | 900 |
| accctgagca ccggccagga tagctggaac cagaccagcg cggtggcca tcatcaccat | 960 |
| caccactaa | 969 |

<210> SEQ ID NO 54
<211> LENGTH: 969
<212> TYPE: DNA
<213> ORGANISM: Streptococcus pyogenes

<400> SEQUENCE: 54

```
atggatgatt atcagcgcaa cgcgaccgaa gcgtatgcga aagaagtgcc gcatcagatt      60
accagcgtgt ggaccaaagg cgtgaccccg ctgaccccgg aacagtttac ccagggcgaa     120
gatgtgtttc atgcgccgta tgtggcgaac cagggctggt atgatattac caaaaccttt     180
aacggcaaag atgatctgct gtgcggcgcg gcgaccgcgg gcaacatgct gcattggtgg     240
tttgatcaga caaagatca gattaaacgc tatctggaag aacatccgga aaacagaaa      300
attaactttc gcggcgaaca gatgtttgat gtgaagaag cgattcgcac caaaaaccat      360
cagctggata gcaaactgtt tgaatatttt aagaaaaag cgtttccgta tctgagcacc      420
aaacatctgg gcgtgtttcc ggatcatgtg attgatatgt ttattaacgg ctatcgcctg     480
agcctgacca ccatggcccc gaccccggtg aaaaaaggca gcaaagatcc gcgcggcggc     540
atttttgatg cggtgtttac ccgcggcaac cagagcaaac tgctgaccag ccgccatgat     600
tttaaagaaa aaaaccctgaa agaaattagc gatctgatta agaagaact gaccaaaggc      660
aaagcgctgg gcctgagcca tacctatgcg aacgtgcgca ttaaccatgt gattaacctg     720
tggggcgcgg attttgatgc ggaaggcaac ctgaaagcga tttatgtgac cgatagcgat     780
agcaacgcga gcattggcat gaaaaaatat tttgtgggcg tgaacaaagc gggcaaagtg     840
gcgattagcg cgaaaaaaat tgaaggcgaa acattggcg cgcaggtgct gggcctgttt       900
accctgagca ccggccagga tagctggaac cagaccaacg gcggtggcca tcatcaccat     960
caccactaa                                                             969
```

<210> SEQ ID NO 55
<211> LENGTH: 963
<212> TYPE: DNA
<213> ORGANISM: Streptococcus pyogenes

<400> SEQUENCE: 55

```
atggatgatt atcagcgcaa cgcgaccgaa gcgtatgcga aagaagtgcc gcatcagatt      60
accagcgtgt ggaccaaagg cgtgaccccg ccggaacagt ttactcaagg tgaagatgtg     120
attcatgcgc cgtatgtggc gaaccagggc tggtatgata ttaccaaagc gtttgatggc     180
aaagataacc tgctgtgcgg cgcggcgacc gcgggcaaca tgctgcattg gtggtttgat     240
cagaacaaag atcagattaa cgctatctg gaagaacatc cggaaaaaca gaaaattaac      300
tttcgcggcg aacagatgtt tgatgtgaaa aaagcgattg ataccaaaaa ccatcagctg     360
gatagcaaac tgtttaacta ttttaaagaa aaagcgtttc cggcctgag cgcgcgccgc      420
attggcgtgt tccggatca tgtgattgat atgtttatta acggctatcg cctgagcctg      480
accaaccatg gcccgacccc ggtgaaagaa ggcagcaaag atccgcgcgg cggcattttt     540
gatgcggtgt ttacccgcgg caaccagagc aaactgctga ccagccgcca tgatttaaaa     600
aacaaaaacc tgaacgatat tagcaccatt attaaacagg aactgaccaa aggcaaagcg     660
ctgggcctga gccataccta tgcgaacgtg agcattaacc atgtgattaa cctgtggggc     720
gcggatttta cgcggaagg caacctggaa gcgatttatg tgaccgatag cgatagcaac     780
gcgagcattg gcatgaaaaa atattttgtg ggcgtgaacg cgcatggcca tgtggcgatt     840
agcgcgaaaa aaattgaagg cgaaaacatt ggcgcgcagg tgctgggcct gtttaccctg     900
agcaccggcc aggatagctg gcagaaactg agcggcggtg gccatcatca ccatcaccac     960
taa                                                                   963
```

US 11,524,057 B2

CYSTEINE PROTEASE

CROSS-REFERENCE TO RELATED APPLICATIONS

This application is a continuation of U.S. patent application Ser. No. 15/550,318 filed Aug. 10, 2017, which is a national phase application under 35 U.S.C. § 371 that claims priority to International Application No. PCT/EP2016/053054 filed Feb. 12, 2016, which claims priority to Great Britain Patent Application No. 1502305.4 filed Feb. 12, 2015, all of which are incorporated herein by reference in their entirety.

FIELD OF THE INVENTION

The present invention relates to a novel polypeptide which displays IgG cysteine protease activity, and in vivo and ex vivo uses thereof. Uses of the polypeptide include methods for the prevention or treatment of diseases and conditions mediated by IgG, and methods for the analysis of IgG.

INCORPORATION OF SEQUENCE LISTING

The instant application contains a Sequence Listing, named "Seq_Lst_KEMP_P0067USC1_1001110926_N404881US.txt" (108 KB), which has been submitted electronically in ASCII format and is hereby incorporated by reference in its entirety.

BACKGROUND OF THE INVENTION

IdeS (Immunoglobulin G-degrading enzyme of *S. pyogenes*) is an extracellular cysteine protease produced by the human pathogen *S. pyogenes*. IdeS was originally isolated from a group A *Streptococcus* strain of serotype MI, but the ides gene has now been identified in all tested group A *Streptococcus* strains. IdeS has an extraordinarily high degree of substrate specificity, with its only identified substrate being IgG. IdeS catalyses a single proteolytic cleavage in the lower hinge region of the heavy chains of all subclasses of human IgG. IdeS also catalyses an equivalent cleavage of the heavy chains of some subclasses of IgG in various animals. IdeS efficiently cleaves IgG to Fc and F(ab')₂ fragments via a two-stage mechanism. In the first stage, one (first) heavy chain of IgG is cleaved to generate a single cleaved IgG (scIgG) molecule with a non-covalently bound Fc molecule. The scIgG molecule is effectively an intermediate product which retains the remaining (second) heavy chain of the original IgG molecule. In the second stage of the mechanism this second heavy chain is cleaved by IdeS to release a F(ab')₂ fragment and a homodimeric Fc fragment. These are the products generally observed under physiological conditions. Under reducing conditions the F(ab')₂ fragment may dissociate to two Fab fragments and the homodimeric Fc may dissociate into its component monomers.

SUMMARY OF THE INVENTION

The IgG cleaving ability of IdeS has been shown to have utility ex vivo, for example in methods for production of Fab and Fc fragments, which may be used for the analysis of IgG. See, for example, WO2003051914 and WO2009033670. IdeS has also been shown to have in vivo utility as a therapeutic agent, since it is capable of the in vivo cleavage of IgG molecules which mediate disease or which are otherwise undesirable. See, for example, WO2003051914, WO2006131347 and WO2013110946. IdeS may be used as a therapy for any disease or condition wholly or partly mediated by IgG. Many autoimmune diseases are wholly or partly mediated by IgG, as is the acute rejection of donated organs.

However, IdeS is an immunogenic protein. That is, when IdeS is used as a therapeutic agent the immune system of the subject receiving IdeS will often respond to it. The reaction of the immune system to IdeS will typically involve the production of antibodies specific for IdeS. These antibodies may be referred to herein as anti-drug antibodies (ADA) specific for IdeS or "IdeS-specific ADA". The immune response to IdeS in general, and the production of IdeS-specific ADA in particular, may cause two related types of problem. Firstly, the efficacy of IdeS may be reduced, e.g. due to ADA binding, potentially requiring higher or repeat doses to achieve the same effect. ADA which have this effect may be referred to as "neutralising ADA". Secondly, there may be undesirable or even harmful complications, such as a hyper-inflammatory response triggered by immune complexes of ADA and IdeS. The higher the quantity of ADA specific for IdeS in a given subject, the greater the likelihood of these problems. The presence and quantity of IdeS-specific ADA molecules in a patient may be determined by any suitable method, such as an agent specific CAP FEIA (ImmunoCAP) test or a titre assay conducted on a serum sample from the patient. Above a threshold determined by the clinician, the quantity of IdeS-specific ADA molecules in the patient may preclude administration of IdeS, or indicate that a higher dose of IdeS is required. Such a higher dose may in turn result in an increased quantity of IdeS-specific ADA molecules in the patient, thereby precluding further administration of IdeS.

IdeS is a virulence factor of *S. pyogenes*, which is responsible for common infections like tonsillitis and strep throat. Accordingly most human subjects have encountered IdeS in this context and are likely to have anti-IdeS antibodies in the bloodstream. IdeS-specific ADA are routinely detected in serum samples from random human subjects (likely due to prior streptococcal infections), as well as in IVIg (Intravenous Immunoglobulin) preparations, which are preparations of IgG extracted from the pooled serum of thousands of donors. Even if a subject does not possess IdeS-specific ADA prior to an initial administration of IdeS, it is likely that such molecules will be produced subsequently. Thus, for any given subject, the problems associated with the immunogenicity of IdeS are likely to present a barrier to the use of IdeS as a treatment. These problems may require increases to the dose of IdeS and/or preclude treatment with IdeS entirely, particularly if repeat administrations are required. Existing approaches to problems of this type involve, for example, PEGylation of a therapeutic agent to reduce immunogenicity or co-administration of the therapeutic agent with an immune-suppressive agent.

The present inventors have adopted an entirely different approach. The inventors analysed the sequence of IdeS and compared it to the sequence of the protein IdeZ, which has approximately 66% identity to IdeS. IdeZ is an IgG cysteine protease produced by *Streptococcus equi* ssp. *zooepidemicus*, a bacterium predominantly found in horses. As IdeZ is not a human pathogen, human subjects do not typically have antibodies against this protein in their plasma. However, IdeZ has a level of IgG cysteine protease activity against human IgG which is considerably lower than that of IdeS. The present inventors investigated positions in the sequence of IdeZ which improve its activity against human IgG without resulting in a significant increase in immunogenicity. As starting points for this investigation, the inventors used both the sequence of IdeZ and the sequence of a novel hybrid sequence designed by the inventors, which has 81.7% identity with IdeS and 81% identity with IdeZ. This hybrid sequence may be referred to herein as IdeS/Z.

The full sequence of IdeS is publically available as NCBI Reference Sequence no. WP_010922160.1 and is provided herein as SEQ ID NO: 1. This sequence includes an N terminal methionine followed by a 28 amino acid secretion signal sequence. The N terminal methionine and the signal sequence (a total of 29 amino acids at the N terminus) are typically removed to form the mature IdeS protein, the sequence of which is publically available as Genbank accession no. ADF13949.1 and is provided herein as SEQ ID NO: 2.

The full sequence of IdeZ is publically available as NCBI Reference Sequence no WP_014622780.1 and is provided herein as SEQ ID NO: 3. This sequence includes an N terminal methionine followed by a 33 amino acid secretion signal sequence. The N terminal methionine and the signal sequence (a total of 34 amino acids at the N terminus) are typically removed to form the mature IdeZ protein, the sequence of which is provided herein as SEQ ID NO: 4.

The sequence of the IdeS/Z hybrid designed by the inventors has an N terminal part based on IdeZ, without the N terminal methionine and the signal sequence (a total of 34 amino acids at the N terminus). This sequence is provided herein as SEQ ID NO: 5.

The present inventors have been able to identify positions within the sequence of IdeZ and IdeS/Z hybrid which, when modified as described herein, lead to novel polypeptides which have increased IgG cysteine protease activity against human IgG relative to IdeZ. The IgG cysteine protease activity against human IgG of a polypeptide of the invention is preferably at least as high as the IgG cysteine protease activity against human IgG of IdeS. A polypeptide of the invention may be more effective at cleaving the first chain of an IgG molecule than the second chain (see schematic representation in FIG. 18), particularly when the IgG is an IgG2 isotype. A polypeptide of the invention may be more effective at cleaving IgG1 than IgG2. The polypeptide of the invention is typically less immunogenic than IdeS and may preferably be no more immunogenic than IdeZ or IdeS/Z.

Unless otherwise stated, all references to numbering of amino acid positions in the polypeptides disclosed herein is based on the numbering of the corresponding positions in SEQ ID NO: 3, starting from the N terminus. Thus, since SEQ ID NOs: 4 and 5 lack the N terminal methionine and 33 amino acid signal sequence of SEQ ID NO: 3, the aspartic acid (D) residue at the N terminus of SEQ ID NOs: 4 and 5 is referred to as position 35 as this the corresponding position in SEQ ID NO: 3. Applying this numbering scheme, the most critical residue for IgG cysteine protease activity of IdeS is the cysteine (C) at position 102 ($68^{th}$ residue from the N terminus of SEQ ID NOs: 4 and 5). Other residues likely to be important for IgG cysteine protease activity are the lysine (K) at position 92, the histidine (H) at position 272, and the aspartic acid (D) at each of positions 294 and 296 of SEQ ID NO: 3. These are the $58^{th}$, $238^{th}$, $260^{th}$ and $262^{nd}$ residues from the N terminus of SEQ ID NO: 4 and the $58^{th}$, $236^{th}$, $258^{th}$ and $260^{th}$ from the N terminus of SEQ ID NO: 5, respectively.

In accordance with the present invention, there is thus provided a polypeptide having IgG cysteine protease activity and comprising a variant of the sequence of SEQ ID NO:4 or 5, which variant:
(a) is at least 50% identical to SEQ ID NO: 4 or 5;
(b) has a cysteine (C) at the position in said variant sequence which corresponds to position 102 of SEQ ID NO: 3; and optionally
(c) has, at the positions in said variant sequence which correspond to positions 92, 272, 294 and 296 of SEQ ID NO: 3, a lysine (K), a histidine (H), an aspartic acid (D) and an aspartic acid (D), respectively;
wherein said polypeptide is more effective at cleaving human IgG than IdeZ and/or is at least as effective at cleaving human IgG as IdeS.

Preferably, said variant of SEQ ID NO: 4 or 5:
(1) has a positively charged amino acid at the position in said variant which corresponds to position 138 of SEQ ID NO: 3, optionally wherein said positively charged amino acid is arginine (R) or lysine (K); and/or
(2) has a positively charged amino acid at the position in said variant which corresponds to position 139 of SEQ ID NO: 3, optionally wherein said positively charged amino acid is arginine (R) or lysine (K); and/or
(3) does not include the contiguous sequence DDYQRNATEA YAKEVPHQIT; and/or
(4) has at least one of the following modifications:
  i. a deletion of the leucine (L) and threonine (T) residues at the positions in said variant which correspond to positions 64 and 65 of SEQ ID NO: 3;
  ii. a threonine (T) in place of the arginine (R) at the position in said variant which corresponds to position 70 of SEQ ID NO: 3;
  iii. a deletion of the tyrosine (Y) at the position in said variant which corresponds to position 71 of SEQ ID NO: 3;
  iv. a glutamine (Q) in place of the asparagine (N) at the position in said variant which corresponds to position 72 of SEQ ID NO: 3;
  v. a glycine (G) in place of the asparagine (N) at the position in said variant which corresponds to position 73 of SEQ ID NO: 3;
  vi. a alanine (A) in place of the glutamic acid (E) at the position in said variant which corresponds to position 67 of SEQ ID NO: 3;
  vii. a asparagine (N) in place of the glutamine (Q) at the position in said variant which corresponds to position 68 of SEQ ID NO: 3.

The at least one modification of (4) is typically selected from options i. to vii. above. A polypeptide of the invention may comprise a variant of the amino acid sequence of SEQ ID NO: 4 or 5, which variant has at least two, three, four, five, six or all seven of the modifications of options i. to vii.

The invention also provides a polynucleotide, an expression vector or a host cell encoding or expressing a polypeptide of the invention.

The invention also provides a method of treating or preventing a disease or condition mediated by IgG antibodies in a subject, the method comprising administering to the subject a therapeutically or prophylactically effective amount of a polypeptide of the invention. The method may typically comprise multiple administrations of said polypeptide to the subject.

The invention also provides a method of treating, ex vivo, blood taken from a patient, typically a patient suffering from a disease or condition mediated by IgG antibodies, which method comprises contacting the blood with a polypeptide of the invention.

The invention also provides a method for improving the benefit to a subject of a therapy or therapeutic agent, the method comprising (a) administering to the subject a polypeptide of the invention; and (b) subsequently administering said therapy or said therapeutic agent to the subject; wherein:
- said therapy is an organ transplant or said therapeutic agent is an antibody, a gene therapy such as a viral vector, a replacement for a defective endogenous factor such as an enzyme, a growth or a clotting factor, or a cell therapy;
- the amount of said polypeptide administered is sufficient to cleave substantially all IgG molecules present in the plasma of the subject; and
- steps (a) and (b) are separated by a time interval which is sufficient to cleave substantially all IgG molecules present in the plasma of the subject.

The invention also provides a method of generating Fc, Fab or F(ab')$_2$ fragments of IgG comprising contacting IgG with a polypeptide of the invention, preferably ex vivo.

Also provided are kits for carrying out the methods according to the invention.

BRIEF DESCRIPTION OF THE SEQUENCES

Figure 1:
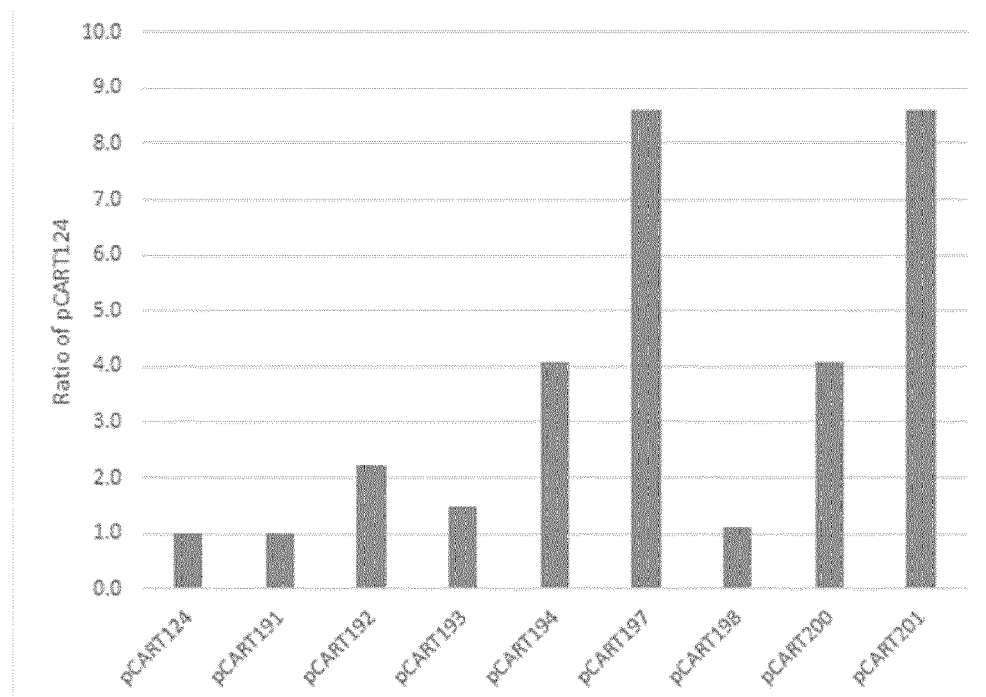
FIGS. 1 and 2 show the results of a representative assay to determine the potency (efficacy at cleavage of IgG) of polypeptides of the invention as compared to controls.

SEQ ID NO: 1 is the full sequence of IdeS including N terminal methionine and signal sequence. Also disclosed as NCBI Reference sequence no. WP_010922160.1

SEQ ID NO: 2 is the mature sequence of IdeS, lacking the N terminal methionine and signal sequence. Also disclosed as Genbank accession no. ADF13949.1

SEQ ID NO: 3 is the full sequence of IdeZ including N terminal methionine and signal sequence. Also disclosed as NCBI Reference sequence no. WP_014622780.1.

SEQ ID NO: 4 is the mature sequence of IdeZ, lacking the N terminal methionine and signal sequence.

SEQ ID NO: 5 is the sequence of a hybrid IdeS/Z designed by the inventors. The N terminus is based on IdeZ lacking the N terminal methionine and signal sequence.

SEQ ID NOs: 6 to 25 are the sequences of exemplary polypeptides of the invention SEQ ID NO: 26 is the sequence of an IdeS polypeptide used herein as a control. Comprises the sequence of SEQ ID NO: 2 with an additional N terminal methionine and a histidine tag (internal reference pCART124).

SEQ ID NO: 27 is the sequence of an IdeZ polypeptide used herein as a control. Comprises the sequence of SEQ ID NO: 4 with an additional N terminal methionine and a histidine tag (internal reference pCART144).

SEQ ID NO: 28 is the sequence of an IdeS/Z polypeptide used herein as a control. Comprises the sequence of SEQ ID NO: 5 with an additional N terminal methionine and a histidine tag (internal reference pCART145).

SEQ ID NO: 29 is the contiguous sequence PLT-PEQFRYNN, which corresponds to positions 63-73 of SEQ ID NO: 3.

SEQ ID NO: 30 is the contiguous sequence PPANFTQG, which corresponds to positions 58-65 of SEQ ID NO: 1.

SEQ ID NO: 31 is the contiguous sequence DDYQR-NATEAYAKEVPHQIT, which corresponds to positions 35-54 of SEQ ID NO: 3.

SEQ ID NO: 32 is the contiguous sequence DSFSANQEIRYSEVTPYHVT, which corresponds to positions 30-49 of SEQ ID NO: 1.

SEQ ID NOs: 33 to 55 are nucleotide sequences encoding polypeptides disclosed herein.

DETAILED DESCRIPTION OF THE INVENTION

It is to be understood that different applications of the disclosed products and methods may be tailored to the specific needs in the art. It is also to be understood that the terminology used herein is for the purpose of describing particular embodiments of the invention only, and is not intended to be limiting.

In addition as used in this specification and the appended claims, the singular forms "a", "an", and "the" include plural referents unless the content clearly dictates otherwise. Thus, for example, reference to "a polypeptide" includes "polypeptides", and the like.

A "polypeptide" is used herein in its broadest sense to refer to a compound of two or more subunit amino acids, amino acid analogs, or other peptidomimetics. The term "polypeptide" thus includes short peptide sequences and also longer polypeptides and proteins. As used herein, the term "amino acid" refers to either natural and/or unnatural or synthetic amino acids, including both D or L optical isomers, and amino acid analogs and peptidomimetics.

The terms "patient" and "subject" are used interchangeably and typically refer to a human. References to IgG typically refer to human IgG unless otherwise stated.

All publications, patents and patent applications cited herein, whether supra or infra, are hereby incorporated by reference in their entirety.

Functional Features of the Polypeptide

The present invention relates to a novel polypeptide having IgG cysteine protease activity, wherein said polypeptide is more effective at cleaving human IgG than IdeZ. The IgG cysteine protease activity against human IgG of a polypeptide of the invention is preferably at least as high as the IgG cysteine protease activity against human IgG of IdeS. In addition the polypeptide of the invention is typically less immunogenic than IdeS and may preferably be no more immunogenic than IdeZ or IdeS/Z. In the context of a control or a comparison relative to a polypeptide of the invention, "IdeS", "IdeZ" and "IdeS/Z" refers to a polypeptide consisting of the amino acid sequence of SEQ ID NO: 2, 4 and 5, respectively. Alternatively or in addition, "IdeS", "IdeZ" and "IdeS/Z" when used as a control or a comparison may refer to a polypeptide comprising the sequence the amino acid sequence of SEQ ID NO: 2, 4 and 5, respectively, with an additional methionine (M) residue at the N terminus and/or a tag at the C terminus to assist with expression in and isolation from standard bacterial expression systems. Suitable tags include a histidine tag which may be joined directly to the C terminus of a polypeptide or joined indirectly by any suitable linker sequence, such as 3, 4 or 5 glycine residues. The histidine tag typically consists of six histidine residues, although it can be longer than this, typically up to 7, 8, 9, 10 or 20 amino acids or shorter, for example 5, 4, 3, 2 or 1 amino acids. The sequence of an exemplary IdeS polypeptide used herein is a control is provided as SEQ ID NO: 22. This polypeptide comprises the sequence of SEQ ID NO: 2 with an additional N terminal methionine and a histidine tag and may be referred to herein as pCART124. The sequence of an exemplary IdeZ polypeptide used herein is a control is provided as SEQ ID NO: 23. This polypeptide comprises the sequence of SEQ ID NO: 4 with an additional N terminal methionine and a histidine tag and may be referred to herein as pCART144. The sequence of an exemplary IdeS/Z polypeptide used herein is a control is provided as SEQ ID NO: 24. This polypeptide comprises the sequence of SEQ ID NO: 5 with an additional N terminal methionine and a histidine tag and may be referred to herein as pCART145.

IgG cysteine protease activity may be assessed by any suitable method, for example by incubating a polypeptide with a sample containing IgG and determining the presence of IgG cleavage products. Efficacy may be assessed in the presence or absence of an inhibitor, such as a neutralising antibody. However, efficacy herein will typically mean efficacy as assessed in the absence of such an inhibitor unless otherwise stated. Suitable methods are described in the Examples. The efficacy of a polypeptide at cleavage of IgG may be referred to herein as the "potency" of the polypeptide. The potency of a polypeptide of the invention is preferably at least 2.0 fold greater than the potency of IdeZ measured in the same assay. Alternatively, the potency of a polypeptide of the invention is preferably at least equivalent to the potency of IdeS measured in the same assay. The potency of a polypeptide of the invention may be at least 1.5 fold, 2.0 fold, 2.5 fold, 3.0 fold, 4.0 fold, 4.5 fold, 5.0 fold, 6.0 fold, 7.0 fold, 7.5 fold or 8.0 fold greater than the potency of IdeS measured in the same assay. The potency of a polypeptide of the invention is preferably at least 2.0 fold, more preferably at least 3.0 or 4.0 fold and most preferably at least 8.0 fold greater than the potency of IdeS measured in the same assay.

The polypeptide of the invention is typically less immunogenic than IdeS and so increased potency relative to that of IdeZ and/or potency equivalent to that of IdeS is an acceptable minimum standard for cysteine protease activity against human IgG. However, increased potency relative to IdeS is a desirable improvement. Such increased potency will typically enable the use of a lower dose of a polypeptide of the invention for the same therapeutic effect as a higher dose of IdeS. The lower dose may also permit a greater number of repeat administrations of a polypeptide of the invention relative to IdeS. This is because the use of a lower dose reduces the problems associated with immunogenicity of a therapeutic agent, because the immune system is less likely to respond, or will respond less vigorously, to an agent which is present at a lower concentration.

Assays for assessing the efficacy of a polypeptide at the cleavage of IgG, that is assays for assessing the potency of a polypeptide, are well known in the art and any suitable assay may be used. Suitable assays include an ELISA-based assay, such as that which is described in the Examples. In such an assay, the wells of an assay plate will typically be coated with an antibody target, such as bovine serum albumin (BSA). Samples of the polypeptide to be tested are then added to the wells, followed by samples of target-specific antibody that is antibody specific for BSA in this example. The polypeptide and antibody are allowed to interact under conditions suitable for IgG cysteine protease activity. After a suitable interval, the assay plate will be washed and a detector antibody which specifically binds to the target-specific antibody will be added under conditions suitable for binding to the target-specific antibody. The detector antibody will bind to any intact target-specific antibody that has bound to the target in each well. After washing, the amount of detector antibody present in a well will be proportional to the amount of target-specific antibody bound to that well. The detector antibody may be conjugated directly or indirectly to a label or another reporter system (such as an enzyme), such that the amount of detector antibody remaining in each well can be determined. The higher the potency of the tested polypeptide that was in a well, the less intact target-specific antibody will remain and thus there will be less detector antibody. Typically, at least one well on a given assay plate will include IdeS instead of a polypeptide to be tested, so that the potency of the tested polypeptides may be directly compared to the potency of IdeS. IdeZ and IdeS/Z may also be included for comparison.

Other assays may determine the potency of a tested polypeptide by directly visualizing and/or quantifying the fragments of IgG which result from cleavage of IgG by a tested polypeptide. An assay of this type is also described in the Examples. Such an assay will typically incubate a sample of IgG with a test polypeptide (or with one or more of IdeS, IdeZ and IdeS/Z as a control) at differing concentrations in a titration series. The products which result from incubation at each concentration are then separated using gel electrophoresis, for example by SDS-PAGE. Whole IgG and the fragments which result from cleavage of IgG can then be identified by size and quantified by the intensity of staining with a suitable dye. The greater the quantity of cleavage fragments, the greater the potency of a tested polypeptide at a given concentration. A polypeptide of the invention will typically produce detectable quantities of cleavage fragments at a lower concentration (a lower point in the titration series) than IdeZ and/or IdeS. This type of assay may also enable the identification of test polypeptides that are more effective at cleaving the first or the second heavy chain of an IgG molecule, as the quantities of the different fragments resulting from each cleavage event may also be determined. A polypeptide of the invention may be more effective at cleaving the first chain of an IgG molecule than the second chain (see schematic representation in FIG. 18), particularly when the IgG is an IgG2 isotype. A polypeptide of the invention may be more effective at cleaving IgG1 than IgG2.

This type of assay may also be adapted to determine the extent to which the presence of IdeS-specific ADA may reduce the potency of a polypeptide of the invention. In the adapted assay, when a sample of IgG is incubated with a test polypeptide (or with IdeS as a control), serum or an IVIg preparation containing IdeS-specific ADA is included with the reaction medium. Preferably, the potency of a polypeptide of the invention is not affected by the presence of ADA or is less reduced by the presence of ADA than the potency of IdeS in the same assay. In other words, preferably the neutralizing effect of IdeS-specific ADA on the polypeptide of the invention is the same or lower than the neutralizing effect of IdeS-specific ADA on IdeS, measured in the same assay.

As indicated above, a polypeptide of the invention is typically less immunogenic than IdeS. That is, a polypeptide of the invention may result in the same or preferably a lower immune response than IdeS when present at an equivalent dose or concentration and measured in the same assay. The immunogenicity of a polypeptide of the invention is typically no more than 50%, no more than 45%, no more than 40%, no more than 35%, no more than 30%, or no more than 25% of the immunogenicity of IdeS measured in the same assay. Preferably the immunogenicity of a polypeptide of the invention is no more than 25% of the immunogenicity of IdeS measured in the same assay.

Assays for assessing the immunogenicity of a polypeptide are also well known in the art and any suitable assay may be used. Preferred assays for assessing the immunogenicity of a polypeptide relative to the immunogenicity of IdeS involves assessing the extent to which ADA specific for IdeS also bind to a polypeptide of the invention. Assays of this type are described in the Examples.

One such an assay involves testing for competition between IdeS and a test polypeptide for binding to IdeS-specific ADA. Typically, the wells of an assay plate are coated with IdeS, followed by administration of a pre-incubated mixture of a solution containing IdeS-specific ADA, e.g. an IVIg preparation, and a test polypeptide (or IdeS as a control). The pre-incubation takes place in the presence of an inhibitor of IgG cysteine protease activity, e.g. iodoacetic acid (IHAc), and at high salt concentration so that only high affinity binding between protein and ADA is permitted. The pre-incubated mixture is allowed to interact with the IdeS coated wells. Any IdeS-specific ADA not bound to test polypeptide will bind to the IdeS on the wells. After a suitable interval, the assay plate will be washed and a detector antibody which specifically binds to IgG will be added under conditions suitable for binding. The detector antibody will bind to any ADA that has bound to the IdeS in each well. After washing, the amount of detector antibody present in a well will be inversely proportional to the amount of ADA that had bound to the test polypeptide. The detector antibody may be conjugated directly or indirectly to a label or another reporter system (such as an enzyme), such that the amount of detector antibody remaining in each well can be determined. Typically, at least one well on a given assay plate will be tested with a pre-incubated mixture of IVIg and IdeS instead of a polypeptide to be tested, so that the binding of ADA to the tested polypeptides may be directly compared to the binding to IdeS, IdeZ and/or IdeS/Z may also be included as further controls.

Another suitable assay involves testing the extent to which a titration series of different concentrations of IdeS-specific ADA, e.g. an IVIg preparation, binds to a test polypeptide as compared to IdeS and/or IdeZ as control. Preferably, a polypeptide of the invention will require a higher concentration of ADA for binding to be detectable, relative to the concentration of ADA for which binding to IdeS is detectable. Such an assay is described in the Examples. Such an assay typically involves coating the wells of an assay plate with test polypeptide or control, followed by incubating with each well with a different concentration of IdeS-specific ADA from a titration series. The incubations are conducted in the presence of an inhibitor of IgG cysteine protease activity, e.g. iodoacetic acid (IHAc), and at high salt concentration so that only high affinity binding between protein and ADA is permitted. After a suitable interval, the assay plate will be washed and a detector antibody which specifically binds to IgG $F(ab')_2$ will be added under conditions suitable for binding. The detector antibody will bind to any ADA that has bound to the test polypeptide or the IdeS in each well. After washing, the amount of detector antibody present in a well will be directly proportional to the amount of ADA that had bound to the test polypeptide or control. The detector antibody may be conjugated directly or indirectly to a label or another reporter system (such as an enzyme), such that the amount of detector antibody remaining in each well can be determined. At least one well on a given assay plate will be incubated with buffer lacking ADA as a blank to establish a threshold level for detection of binding in the test wells.

Structural Features of the Polypeptide

This section sets out the structural features of a polypeptide of the invention, which apply in addition to the functional features outlined in the preceding section.

The polypeptide of the invention is typically at least 100, 150, 200, 250, 260, 270, 280, 290, 300 or 310 amino acids in length. The polypeptide of the invention is typically no larger than 400, 350, 340, 330, 320 or 315 amino acids in length. It will be appreciated that any of the above listed lower limits may be combined with any of the above listed upper limits to provide a range for the length the polypeptide of the invention. For example, the polypeptide may be 100 to 400 amino acids in length, or 250 to 350 amino acids in length.

The polypeptide is preferably 290 to 320 amino acids in length, most preferably 300 to 315 amino acids in length.

The primary structure (amino acid sequence) of a polypeptide of the invention is based on the primary structure of IdeZ or IdeS/Z, specifically the amino acid sequence of SEQ ID NO: 4 or 5, respectively. The sequence of a polypeptide of the invention comprises a variant of the amino acid sequence of SEQ ID NO: 4 or 5, which is at least 50% identical to the amino acid sequence of SEQ ID NO: 4 or 5. The variant sequence may be at least 60%, at least 70%, at least 80%, at least, 85%, preferably at least 90%, at least 95%, at least 98% or at least 99% identical to the sequence of SEQ ID NO: 4 or 5. The variant may be identical to the sequence of SEQ ID NO: 4 or 5 apart from the inclusion of one or more of the specific modifications identified herein. Identity relative to the sequence of SEQ ID NO: 4 or 5 can be measured over a region of at least 50, at least 100, at least 200, at least 300 or more contiguous amino acids of the sequence shown in SEQ ID NO: 4 or 5, or more preferably over the full length of SEQ ID NO: 4 or 5.

Amino acid identity may be calculated using any suitable algorithm. For example the PILEUP and BLAST algorithms can be used to calculate identity or line up sequences (such as identifying equivalent or corresponding sequences (typically on their default settings), for example as described in Altschul S. F. (1993) J Mol Evol 36:290-300; Altschul, S, F et al (1990) J Mol Biol 215:403-10. Software for performing BLAST analyses is publicly available through the National Center for Biotechnology Information (see the National Center for Biotechnology Information website on the world wide web). This algorithm involves first identifying high scoring sequence pair (HSPs) by identifying short words of length W in the query sequence that either match or satisfy some positive-valued threshold score T when aligned with a word of the same length in a database sequence. T is referred to as the neighbourhood word score threshold (Altschul et al, supra). These initial neighbourhood word hits act as seeds for initiating searches to find HSPs containing them. The word hits are extended in both directions along each sequence for as far as the cumulative alignment score can be increased. Extensions for the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T and X determine the sensitivity and speed of the alignment. The BLAST program uses as defaults a word length (W) of 11, the BLOSUM62 scoring matrix (see Henikoff and Henikoff (1992) Proc. Natl. Acad. Sci. USA 89: 10915-10919) alignments (B) of 50, expectation (E) of 10, M=5, N=4, and a comparison of both strands.

The BLAST algorithm performs a statistical analysis of the similarity between two sequences; see e.g., Karlin and Altschul (1993) *Proc. Natl. Acad. Sci. USA* 90: 5873-5787. One measure of similarity provided by the BLAST algorithm is the smallest sum probability (P(N)), which provides an indication of the probability by which a match between two polynucleotide or amino acid sequences would occur by chance. For example, a sequence is considered similar to another sequence if the smallest sum probability in comparison of the first sequence to the second sequence is less than about 1, preferably less than about 0.1, more preferably less than about 0.01, and most preferably less than about 0.001. Alternatively, the UWGCG Package provides the BESTFIT program which can be used to calculate identity (for example used on its default settings) (Devereux et al (1984) Nucleic Acids Research 12, 387-395).

The sequence of a polypeptide of the invention comprises a variant of the amino acid sequence of SEQ ID NO: 4 or 5 in which modifications, such as amino acid additions, deletions or substitutions are made relative to the sequence of SEQ ID NO: 4 or 5. Unless otherwise specified, the modifications are preferably conservative amino acid substitutions. Conservative substitutions replace amino acids with other amino acids of similar chemical structure, similar chemical properties or similar side-chain volume. The amino acids introduced may have similar polarity, hydrophilicity, hydrophobicity, basicity, acidity, neutrality or charge to the amino acids they replace. Alternatively, the conservative substitution may introduce another amino acid that is aromatic or aliphatic in the place of a pre-existing aromatic or aliphatic amino acid. Conservative amino acid changes are well-known in the art and may be selected in accordance with the properties of the 20 main amino acids as defined in Table A1 below. Where amino acids have similar polarity, this can be determined by reference to the hydropathy scale for amino acid side chains in Table A2.

TABLE A1

Chemical properties of amino acids

| | |
|---|---|
| Ala (A) | aliphatic, hydrophobic, neutral |
| Cys (C) | polar, hydrophobic, neutral |
| Asp (D) | polar, hydrophilic, charged (−) |
| Glu (E) | polar, hydrophilic, charged (−) |
| Phe (F) | aromatic, hydrophobic, neutral |
| Gly (G) | aliphatic, neutral |
| His (H) | aromatic, polar, hydrophilic, charged (+) |
| Ile (I) | aliphatic, hydrophobic, neutral |
| Lys (K) | polar, hydrophilic, charged(+) |
| Leu (L) | aliphatic, hydrophobic, neutral |
| Met (M) | hydrophobic, neutral |
| Asn (N) | polar, hydrophilic, neutral |
| Pro (P) | hydrophobic, neutral |
| Gln (Q) | polar, hydrophilic, neutral |
| Arg (R) | polar, hydrophilic, charged (+) |
| Ser (S) | polar, hydrophilic, neutral |
| Thr (T) | polar, hydrophilic, neutral |
| Val (V) | aliphatic, hydrophobic, neutral |
| Trp (W) | aromatic, hydrophobic, neutral |
| Tyr (Y) | aromatic, polar, hydrophobic |

TABLE A2

Hydropathy scale

| Side Chain | Hydropathy |
|---|---|
| Ile | 4.5 |
| Val | 4.2 |
| Leu | 3.8 |
| Phe | 2.8 |
| Cys | 2.5 |
| Met | 1.9 |
| Ala | 1.8 |
| Gly | −0.4 |
| Thr | −0.7 |
| Ser | −0.8 |
| Trp | −0.9 |
| Tyr | −1.3 |
| Pro | −1.6 |
| His | −3.2 |

TABLE A2-continued

| Hydropathy scale | |
|---|---|
| Side Chain | Hydropathy |
| Glu | −3.5 |
| Gln | −3.5 |
| Asp | −3.5 |
| Asn | −3.5 |
| Lys | −3.9 |
| Arg | −4.5 |

The amino acid sequence of a polypeptide of the invention comprises a variant of the amino acid sequence of SEQ ID NO: 4 or 5. However, certain residues in the amino acid sequence of SEQ ID NO: 4 or 5 are preferably retained within the said variant sequence. For example, the said variant sequence typically retains certain residues which are known to be required for IgG cysteine protease activity. Thus, the cysteine at position 102 of SEQ ID NO: 3 must be retained (68$^{th}$ residue of SEQ ID NO: 4 or 5) in the amino acid sequence of a polypeptide of the invention. Optionally, the lysine (K) at position 92, the histidine (H) at position 272, and the aspartic acid (D) at each of positions 294 and 296 of SEQ ID NO: 3.are also retained. These are the 58$^{th}$, 238$^{th}$, 260$^{th}$ and 262$^{th}$ residues from the N terminus of SEQ ID NO: 4 and the 58$^{th}$, 236$^{th}$, 258$^{th}$ and 260$^{th}$ from the N terminus of SEQ ID NO: 5, respectively. Thus, a polypeptide of the invention typically comprises a variant of the amino acid sequence of SEQ ID NO: 2 which has a cysteine (C) at the position in said variant sequence which corresponds to position 102 of SEQ ID NO: 3; and optionally has, at the positions in said variant sequence which correspond to positions 92, 272, 294 and 296 of SEQ ID NO: 3, a lysine (K), a histidine (H), an aspartic acid (D) and an aspartic acid (D), respectively.

Starting with the above structural limitations, the inventors identified specific positions for modification to adjust the functional properties of IdeS by assessing a three dimensional model of IdeS. The inventors have identified that:

(1) Replacing the asparagine (N) at position 138 of SEQ ID NO: 3 with a positively charged amino acid enhances the potency of a polypeptide which incorporates this change. Thus, a polypeptide of the invention may comprise a variant of the amino acid sequence of SEQ ID NO: 4 or 5 which has a positively charged amino acid at the position in said variant which corresponds to position 138 of SEQ ID NO: 3. Common positively charged amino acids are identified in Table A1 above. The positively charged amino acid is preferably arginine (R) or lysine (K). Accordingly this particular modification may be identified herein by the term "N138R/K".

(2) Replacing the asparagine (N) at position 139 of SEQ ID NO: 3 with a positively charged amino acid enhances the potency of a polypeptide which incorporates this change. Thus, a polypeptide of the invention may comprise a variant of the amino acid sequence of SEQ ID NO: 4 or 5 which has a positively charged amino acid at the position in said variant which corresponds to position 139 of SEQ ID NO: 3. Common positively charged amino acids are identified in Table A above. The positively charged amino acid is preferably arginine (R) or lysine (K). Accordingly this particular modification may be identified herein by the term "N139R/K".

(3) Deleting the first twenty residues at the N terminus of SEQ ID NO: 3 may enhance the potency of a polypeptide which incorporates this change and/or may reduce immunogenicity without adversely affecting potency. The first twenty residues at the N terminus of SEQ ID NO: 3 consist of the contiguous sequence DDYQRNATEAYAKEVPHQIT. Thus, a polypeptide of the invention may comprise a variant of the amino acid sequence of SEQ ID NO: 4 or 5 which does not include the contiguous sequence DDYQRNATEAYAKEVPHQIT. That is, the first twenty residues at the N terminus of SEQ ID NO: 4 or 5 may be absent from said variant of SEQ ID NO: 4 or 5. The first twenty residues of SEQ ID NOs: 4 and 5 correspond to positions 35-54 of SEQ ID NO: 3. Accordingly this particular modification may be identified herein by the term "D35_T54del".

(4) The region which corresponds to positions 63-73 of SEQ ID NO: 3 is important for the IgG cysteine protease activity of a polypeptide of the invention. Modifications in this region primarily improve the ability of the polypeptide to cleave the second IgG heavy chain, but they also enhance cleavage of the first IgG heavy chain. Specifically, modifying one or more residues within this region in favour of the corresponding residue (or an amino acid with similar characteristics to the corresponding residue) in the equivalent region of IdeS increases the potency of a polypeptide of the invention. The equivalent region in IdeS corresponds to positions 58-65 of SEQ ID NO: 1. The following alignment shows positions 63-73 of SEQ ID NO: 3 alongside positions 58-65 of SEQ ID NO: 1.

$^{63}$PLTPEQFRYNN$^{73}$ (region of IdeZ, SEQ ID NO: 3)

$^{58}$P--PANFT-QG$^{65}$ (region of IdeS, SEQ ID NO: 1)

"-" indicates absent residue

Thus, a polypeptide of the invention may comprise a variant of the amino acid sequence of SEQ ID NO: 4 or 5, which variant may have at least one of the following modifications:
  i. a deletion of the leucine (L) and threonine (T) residues at the positions in said variant which correspond to positions 64 and 65 of SEQ ID NO: 3;
  ii. a threonine (T) in place of the arginine (R) at the position in said variant which corresponds to position 70 of SEQ ID NO: 3;
  iii. a deletion of the tyrosine (Y) at the position in said variant which corresponds to position 71 of SEQ ID NO: 3;
  iv. a glutamine (Q) in place of the asparagine (N) at the position in said variant which corresponds to position 72 of SEQ ID NO: 3;
  v. a glycine (G) in place of the asparagine (N) at the position in said variant which corresponds to position 73 of SEQ ID NO: 3;
  vi. a alanine (A) in place of the glutamic acid (E) at the position in said variant which corresponds to position 67 of SEQ ID NO: 3;
  vii. a asparagine (N) in place of the glutamine (Q) at the position in said variant which corresponds to position 68 of SEQ ID NO: 3.

The at least one modification from options i. to vii. above is typically selected from options i. to v. A polypeptide of the invention may comprise a variant of the amino acid sequence of SEQ ID NO: 4 or 5, which variant has at least two, three, four, or all five of the modifications of i. to v. Preferably, said variant has at least one, two, three of all four of modifications ii. to v., and optionally modification i. is also present. In a particularly preferred said variant, all of modifications i. to v. are present.

In summary therefore, a polypeptide of the invention comprises a variant of the sequence of SEQ ID NO: 4 or 5, which variant:
- (a) is at least 50% identical to SEQ ID NO: 4 or 5;
- (b) has a cysteine (C) at the position in said variant sequence which corresponds to position 102 of SEQ ID NO: 3; and optionally
- (c) has, at the positions in said variant sequence which correspond to positions 92, 272, 294 and 296 of SEQ ID NO: 3, a lysine (K), a histidine (H), an aspartic acid (D) and an aspartic acid (D), respectively.

Preferably, said variant of SEQ ID NO: 4 or 5:
- (1) has a positively charged amino acid at the position in said variant which corresponds to position 138 of SEQ ID NO: 3, optionally wherein said positively charged amino acid is arginine (R) or lysine (K); and/or
- (2) has a positively charged amino acid at the position in said variant which corresponds to position 139 of SEQ ID NO: 3, optionally wherein said positively charged amino acid is arginine (R) or lysine (K); and/or
- (3) does not include the contiguous sequence DDYQR-NATEA YAKEVPHQIT; and/or
- (4) has at least one of the following modifications:
  - i. a deletion of the leucine (L) and threonine (T) residues at the positions in said variant which correspond to positions 64 and 65 of SEQ ID NO: 3;
  - ii. a threonine (T) in place of the arginine (R) at the position in said variant which corresponds to position 70 of SEQ ID NO: 3;
  - iii. a deletion of the tyrosine (Y) at the position in said variant which corresponds to position 71 of SEQ ID NO: 3;
  - iv. a glutamine (Q) in place of the asparagine (N) at the position in said variant which corresponds to position 72 of SEQ ID NO: 3;
  - v. a glycine (G) in place of the asparagine (N) at the position in said variant which corresponds to position 73 of SEQ ID NO: 3;
  - vi. a alanine (A) in place of the glutamic acid (E) at the position in said variant which corresponds to position 67 of SEQ ID NO: 3;
  - vii. a asparagine (N) in place of the glutamine (Q) at the position in said variant which corresponds to position 68 of SEQ ID NO: 3.

wherein the at least one modification of (4) is typically selected from options i. to v, and wherein preferably all of options ii. to v. are present optionally also with option i.

A polypeptide of the invention typically comprises a variant of the amino acid sequence of SEQ ID NO: 4 or 5 which variant includes at least one, two, three or all four of modifications (1) to (4) set out above. Said variant may include any combination of two or three of the modifications of (1) to (4). A preferred variant includes modification (3) and at least one of modifications (1) and (2). Alternatively, the variant may include none of the modifications of (1) to (3) set out above.

The inventors have also determined that certain other modifications to the sequence of SEQ ID NO: 4 or 5, which may be applied alternatively or in addition to any combination of the modifications described above, may increase the potency of a polypeptide of the invention and/or may reduce the recognition of a polypeptide of the invention by IdeS-specific ADA. Thus, alternatively or in addition to the modifications set out above, the polypeptide of the invention may comprise:

(A) a variant of the sequence of SEQ ID NO: 4 in which a substitution is made at one or more of the positions corresponding to positions 84, 93, 95, 97, 137, 140, 147, 150, 162, 165, 166, 171, 174, 205, 226, 237, 239, 243, 250, 251, 254, 255, 282, 288, 312, 315, 347, 349 of SEQ ID NO: 3, and/or in which the contiguous sequence corresponding to positions 36 to 53 of SEQ ID NO: 3 is replaced with the contiguous sequence at positions 31 to 48 of SEQ ID NO: 2 (this change may be referred to as "D36_I53replacedS31_V48 of SEQ 2");

or (B) a variant of the sequence of SEQ ID NO: 5 in which a substitution is made at one or more of the positions corresponding to positions 77, 93, 95, 99, 140, 141, 147, 150, 162, 171, 174, 175, 176, 177, 206, 224, 237, 241, 242, 245, 246, 249, 253, 267, 280, 286, 310, 311, 313, 344, 345, 346, 347.

The said variant (A) may comprise a substitution in all of the listed positions, or any combination of one or more of the listed positions, but typically comprises a substitution in no more than twelve, eleven or ten of these positions.

The said variant (B) may comprise a substitution in all of the listed positions, or any combination of one or more of the listed positions, but typically comprises a substitution in no more than thirty of these positions.

The substitutions typically replace the existing amino acid with another amino acid that has different properties. For example, an uncharged amino acid may be replaced with a charged amino acid, and vice versa. Preferred substitutions at these positions are set out in Table B1 and B2 below using the one letter code:

TABLE B1

| variant A | | |
|---|---|---|
| Existing amino acid in SEQ ID NO: 4 | Position in SEQ ID NO: 3 | Preferred replacement |
| H | 84 | N |
| A | 93 | T |
| D | 95 | N |
| K | 97 | A |
| F | 137 | I |
| Q | 140 | E |
| A | 147 | E |
| D | 150 | R |
| N | 162 | E |
| R | 165 | K |
| D | 166 | E |
| N | 171 | Y |
| A | 174 | T |
| N | 205 | K |
| D | 226 | N |
| L | 237 | F |
| N | 239 | E |
| N | 243 | K |
| K | 250 | S |
| Q | 251 | E |
| T | 254 | E |
| E | 255 | K |
| N | 282 | D |
| E | 288 | K |
| A | 312 | K |
| H | 315 | K |
| K | 347 | Q |
| S | 349 | N |

TABLE B2

| Existing amino acid in SEQ ID NO: 5 | Position in SEQ ID NO: 3 | Preferred replacement |
|---|---|---|
| F | 77 | I |
| A | 93 | T |
| D | 95 | N |
| N | 99 | D |
| D | 140 | E |
| N | 141 | Q |
| K | 147 | E |
| D | 150 | R |
| N | 162 | E |
| G | 171 | Y |
| A | 174 | T |
| R | 175 | K |
| R | 176 | H |
| I | 177 | L |
| E | 206 | K |
| D | 224 | N |
| N | 237 | E |
| N | 241 | K |
| D | 242 | E |
| T | 245 | D |
| I | 246 | L |
| Q | 249 | E |
| K | 253 | E |
| S | 267 | R |
| N | 280 | D |
| E | 286 | K |
| A | 310 | K |
| H | 311 | A |
| H | 313 | K |
| Q | 344 | N |
| K | 345 | Q |
| L | 346 | T |
| S | 347 | N |

(header spans "variant B")

Each of the substitutions in tables B1 and B2 may be referred to herein using a term obtained by combining the entries in the first, second and third columns for each row from left to right. For example, the substitution in the first row of table B1 may be referred to herein as "H84N", the substitution in the second row may be referred to as "A93T", and so on. The specific modification "D226N" in Table B1 and "D224N" in Table B2 is intended to disrupt a known cell adhesion motif in the sequence of IdeZ and IdeS/Z, which is the contiguous RGD sequence at positions 224-226 of SEQ ID NO: 3.

Table C1 and C2 below summarize the modifications made to produce the amino acid sequences of certain exemplary polypeptides of the invention.

TABLE C1

| Internal reference | Modifications relative to IdeZ (SEQ ID NO: 4) (positions correspond to SEQ ID NO: 3) | SEQ ID NO of full sequence |
|---|---|---|
| pCART197 | H84N, N138R, A147E, D150R, N162E, N171Y, N205K, D226N, Q251E, E255K, A312K, S349N | 6 |
| pCART198 | A93T, D95N, Q140E, R165K, D166E, A174T, D226N, L237F, N239E, N243K, N282D, E288K, H315K, K347Q | 7 |
| pCART200 | D36_I53replacedS31_V48 of SEQ 2 i.e. SFSANQEI RYSEVTPYHV replaces DYQRNATE AYAKEVPHQI | 8 |
| pCART201 | D35_T54del | 9 |
| pCART202 | R70T, Y71del, N72Q, N73G | 10 |
| pCART203 | L64_T65del, R70T, Y71del, N72Q, N73G | 11 |
| pCART204 | R70T, Y71del | 12 |
| pCART206 | L64_T65del, R70T, Y71del, N72Q, N73G, F137I | 13 |
| pCART207 | L64_T65del, R70T, Y71del, N72Q, N73G, N138R | 14 |
| pCART208 | L64_T65del, R70T, Y71del, N72Q, N73G, F137I, N138R | 15 |
| pCART210 | L64_T65del, R70T, Y71del, N72Q, N73G, H84N, N138R, N162E, N205K, D226N | 16 |
| pCART217 | D35_T54del, L64_T65del, R70T, Y71del, N72Q, N73G, N138R, D226N | 17 |
| pCART219 | L64_T65del, R70T, Y71del, N72Q, N73G, K97A, N138R, D226N | 18 |
| pCART226 | D35_T54del, L64_T65del, R70T, Y71del, N72Q, N73G, K97A, N138R, D226N | 19 |
| pCART229 | L64_T65del, R70T, Y71del, N72Q, N73G, N138R, D226N | 20 |

TABLE C2

| Internal reference | Modifications relative to IdeS/Z (SEQ ID NO: 5) (positions correspond to SEQ ID NO: 3) | SEQ ID NO of full sequence |
|---|---|---|
| pCART191 | R70T, Y71del, N72Q, N73G, D140E, G171Y, R175K, R176H, I177L, S267R | 21 |
| pCART192 | R70T, Y71del, N72Q, N73G, N138R, D140E, K147E, D150R, N162E, G171Y, R175K, R176H, I177L, E206K, Q249S, K253N, S267R, A310K, S347N | 22 |
| pCART193 | R70T, Y71del, N72Q, N73G, A93T, D95N, N99D, D140E, N141Q, K147E, N162E, G171Y, A174T, R175K, R176H, I177L, N237E, N241K, D242E, T245D, I246L, K253E, S267R, E286K, H311A, H313K, Q344N, K345Q, L346T | 23 |
| pCART194 | R70T, Y71del, N72Q, N73G, A93T, D95N, N99D, N138R, D140E, N141Q, K147E, D150R, N162E, G171Y, A174T, R175K, R176H, I177L, E206K, N237E, N241K, D242E, T245D, I246L, Q249E, S267R, N280D, E286K, A310K, H311A, H313K, Q344N, K345Q, L346T, S347N | 24 |
| pCART205 | L64_65del, R70T, Y71del, N72Q, N73G, F77I, N138R, D140E, N141Q | 25 |

The amino acid sequence of each of SEQ ID NOs: 1 to 5 is reproduced in full below, followed by the amino acid sequence of each of the exemplary polypeptides of the invention described in Tables C1 and C2.

SEQ ID NO: 1

MRKRCYSTSAAVLAAVTLFVLSVDRGVIADSFSANQEIRYSEVIPYHVISVWTKGVIPPANFTQGEDVFHAPYVA

NQGWYDITKIFNGKDDLLCGAATAGNMLHWWFDQNKDQIKRYLEEHPEKQKINFNGEQMFDVKEAIDTKNHQLDS

KLFEYFKEKAFPYLSTKHLGVFPDHVIDMFINGYRLSLINHGPTPVKEGSKDPRGGIFDAVFIRGDQSKLLTSRH

-continued

DFKEKNLKEISDLIKKELTEGKALGLSHIYANVRINHVINLWGADFDSNGNLKAIYVIDSDSNASIGMKKYFVGV

NSAGKVAISAKEIKEDNIGAQVLGLFILSTGQDSWNQIN

SEQ ID NO: 2

DSFSANQEIRYSEVIPYHVISVWTKGVIPPANFTQGEDVFHAPYVANQGWYDITKIFNGKDDLLCGAATA

GNMLHWWFDQNKDQIKRYLEEHPEKQKINFNGEQMFDVKEAIDTKNHQLDSKLFEYFKEKAFPYLSTKHL

GVFPDHVIDMFINGYRLSLINHGPTPVKEGSKDPRGGIFDAVFIRGDQSKLLTSRHDFKEKNLKEISDLI

KKELTEGKALGLSHIYANVRINHVINLWGADFDSNGNLKAIYVIDSDSNASIGMKKYFVGVNSAGKVAIS

AKEIKEDNIGAQVLGLFILSTGQDSWNQIN

SEQ ID NO: 3

MKTIAYPNKPHSLSAGLLTAIAIFSLASSNITYADDYQRNATEAYAKEVPHQITSVWTKGVIPLIPEQFRYNNED

VIHAPYLAHQGWYDITKAFDGKDNLLCGAATAGNMLHWWFDQNKTEIEAYLSKHPEKQKIIFNNQELFDLKAAID

TKDSQINSQLFNYFRDKAFPNLSARQLGVMPDLVLDMFINGYYLNVFKIQSTDVNRPYQDKDKRGGIFDAVFIRG

DQTILLTARHDLKNKGLNDISTIIKQELTEGRALALSHIYANVSISHVINLWGADFNAEGNLEAIYVIDSDANAS

IGMKKYFVGINAHGHVAISAKKIEGENIGAQVLGLFTLSSGKDIWQKLS

SEQ ID NO: 4

DDYQRNATEAYAKEVPHQITSVWTKGVIPLIPEQFRYNNEDVIHAPYLAHQGWYDITKAFDGKDNLLCGAATAGN

MLHWWFDQNKTEIEAYLSKHPEKQKIIFNNQELFDLKAAIDTKDSQINSQLFNYFRDKAFPNLSARQLGVMPDLV

LDMFINGYYLNVFKIQSTDVNRPYQDKDKRGGIFDAVFIRGDQTLLLTARHDLKNKGLNDISTIIKQELTEGRAL

ALSHIYANVSISHVINLWGADFNAEGNLEAIYVIDSDANASIGMKKYFVGINAHGHVAISAKKIEGENIGAQVLG

LFTLSSGKDIWQKLS

SEQ ID NO: 5

DDYQRNATEAYAKEVPHQITSVWTKGVIPLIPEQFRYNNEDVFHAPYVANQGWYDITKAFDGKDNLLCGAATAGN

MLHWWFDQNKDQIKRYLEEHPEKQKINFNGDNMFDVKKAIDTKNHQLDSKLFNYFKEKAFPGLSARRIGVFPDHV

IDMFINGYRLSLINHGPTPVKEGSKDPRGGIFDAVFIRGNQSKLLTSRHDFKNKNLNDISTIIKQELTKGKALGL

SHIYANVSINHVINLWGADFNAEGNLEAIYVIDSDSNASIGMKKYFVGVNAHGHVAISAKKIEGENIGAQVLGLF

TLSTGQDSWQKLS (pCART197)

SEQ ID NO: 6

DDYQRNATEAYAKEVPHQITSVWTKGVIPLIPEQFRYNNEDVIHAPYLANQGWYDITKAFDGKDNLLCGAATAGN

MLHWWFDQNKTEIEAYLSKHPEKQKIIFRNQELFDLKEAIRTKDSQINSQLFEYFRDKAFPYLSARQLGVMPDLV

LDMFINGYYLNVFKIQSTDVKRPYQDKDKRGGIFDAVFIRGNQTTLLTARHDLKNKGLNDISTIIKEELTKGRAL

ALSHIYANVSISHVINLWGADFNAEGNLEAIYVIDSDANASIGMKKYFVGINKHGHVAISAKKIEGENIGAQVLG

LFTLSSGKDIWQKLN (pCART198)

SEQ ID NO: 7

DDYQRNATEAYAKEVPHQITSVWTKGVIPLIPEQFRYNNEDVIHAPYLAHQGWYDITKIFNGKDNLLCGAATAGN

MLHWWFDQNKTEIEAYLSKHPEKQKIIFNNEELFDLKAAIDTKDSQINSQLFNYFKEKAFPNLSTRQLGVMPDLV

LDMFINGYYLNVFKIQSTDVNRPYQDKDKRGGIFDAVFIRGNQTTLLTARHDFKEKGLKDISTIIKQELTEGRAL

ALSHIYANVSISHVINLWGADFDAEGNLKAIYVIDSDANASIGMKKYFVGINAHGKVAISAKKIEGENIGAQVLG

LFTLSSGKDIWQQLS (pCART200)

SEQ ID NO: 8

DSFSANQEIRYSEVIPYHVISVWTKGVIPLIPEQFRYNNEDVIHAPYLAHQGWYDITKAFDGKDNLLCGAATAGN

MLHWWFDQNKTEIEAYLSKHPEKQKIIFNNQELFDLKAAIDTKDSQINSQLFNYFRDKAFPNLSARQLGVMPDLV

LDMFINGYYLNVFKIQSTDVNRPYQDKDKRGGIFDAVFIRGDQTTLLTARHDLKNKGLNDISTIIKQELTEGRAL

-continued

ALSHIYANVSISHVINLWGADFNAEGNLEAIYVIDSDANASIGMKKYFVGINAHGHVAISAKKIEGENIGAQVLG

LFTLSSGKDIWQKLS (pCART201)

SEQ ID NO: 9
SVWTKGVIPLIPEQFRYNNEDVIHAPYLAHQGWYDITKAFDGKDNLLCGAATAGNMLHWWFDQNKTEIEAYLSKH

PEKQKIIFNNQELFDLKAAIDTKDSQINSQLFNYFRDKAFPNLSARQLGVMPDLVLDMFINGYYLNVFKIQSTDV

NRPYQDKDKRGGIFDAVFIRGDQTILLTARHDLKNKGLNDISTIIKQELTEGRALALSHIYANVSISHVINLWGA

DFNAEGNLEAIYVIDSDANASIGMKKYFVGINAHGHVAISAKKIEGENIGAQVLGLFILSSGKDIWQKLS (pCART202)

SEQ ID NO: 10
DDYQRNATEAYAKEVPHQITSVWTKGVIPLIPEQFTQGEDVIHAPYLAHQGWYDITKAFDGKDNLLCGAATAGNM

LHWWFDQNKTEIEAYLSKHPEKQKIIFNNQELFDLKAAIDTKDSQINSQLFNYFRDKAFPNLSARQLGVMPDLVL

DMFINGYYLNVFKIQSTDVNRPYQDKDKRGGIFDAVFIRGDQTTLLTARHDLKNKGLNDISTIIKQELTEGRALA

LSHIYANVSISHVINLWGADFNAEGNLEAIYVIDSDANASIGMKKYFVGINAHGHVAISAKKIEGENIGAQVLGL

FTLSSGKDIWQKLS (pCART203)

SEQ ID NO: 11
DDYQRNATEAYAKEVPHQITSVWTKGVIPPEQFTQGEDVIHAPYLAHQGWYDITKAFDGKDNLLCGAATAGNMLH

WWFDQNKTEIEAYLSKHPEKQKIIFNNQELFDLKAAIDTKDSQINSQLFNYFRDKAFPNLSARQLGVMPDLVLDM

FINGYYLNVFKIQSTDVNRPYQDKDKRGGIFDAVFIRGDQTTLLTARHDLKNKGLNDISTIIKQELTEGRALALS

HIYANVSISHVINLWGADFNAEGNLEAIYVIDSDANASIGMKKYFVGINAHGHVAISAKKIEGENIGAQVLGLFT

LSSGKDIWQKLS (pCART204)

SEQ ID NO: 12
DDYQRNATEAYAKEVPHQITSVWTKGVIPPEQFRYNNEDVIHAPYLAHQGWYDITKAFDGKDNLLCGAATAGNML

HWWFDQNKTEIEAYLSKHPEKQKIIFNNQELFDLKAAIDTKDSQINSQLFNYFRDKAFPNLSARQLGVMPDLVLD

MFINGYYLNVFKIQSTDVNRPYQDKDKRGGIFDAVFIRGDQTTLLTARHDLKNKGLNDISTIIKQELTEGRALAL

SHIYANVSISHVINLWGADFNAEGNLEAIYVIDSDANASIGMKKYFVGINAHGHVAISAKKIEGENIGAQVLGLF

TLSSGKDIWQKLS (pCART 206)

SEQ ID NO: 13
DDYQRNATEAYAKEVPHQITSVWTKGVIPPEQFTQGEDVIHAPYLAHQGWYDITKAFDGKDNLLCGAATAGNMLH

WWFDQNKTEIEAYLSKHPEKQKIIINNQELFDLKAAIDTKDSQINSQLFNYFRDKAFPNLSARQLGVMPDLVLDM

FINGYYLNVFKIQSTDVNRPYQDKDKRGGIFDAVFIRGDQTTLLTARHDLKNKGLNDISTIIKQELTEGRALALS

HIYANVSISHVINLWGADFNAEGNLEAIYVIDSDANASIGMKKYFVGINAHGHVAISAKKIEGENIGAQVLGLFT

LSSGKDIWQKLS (pCART207)

SEQ ID NO: 14
DDYQRNATEAYAKEVPHQITSVWTKGVIPPEQFTQGEDVIHAPYLAHQGWYDITKAFDGKDNLLCGAATAGNMLH

WWFDQNKTEIEAYLSKHPEKQKIIFRNQELFDLKAAIDTKDSQINSQLFNYFRDKAFPNLSARQLGVMPDLVLDM

FINGYYLNVFKIQSTDVNRPYQDKDKRGGIFDAVFIRGDQTTLLTARHDLKNKGLNDISTIIKQELTEGRALALS

HIYANVSISHVINLWGADFNAEGNLEAIYVIDSDANASIGMKKYFVGINAHGHVAISAKKIEGENIGAQVLGLFT

LSSGKDIWQKLS (pCART208)

SEQ ID NO: 15
DDYQRNATEAYAKEVPHQITSVWTKGVIPPEQFTQGEDVIHAPYLAHQGWYDITKAFDGKDNLLCGAATAGNMLH

WWFDQNKTEIEAYLSKHPEKQKIIIRNQELFDLKAAIDTKDSQINSQLFNYFRDKAFPNLSARQLGVMPDLVLDM

FINGYYLNVFKTQSTDVNRPYQDKDKRGGIFDAVFTRGDQTTLLTARHDLKNKGLNDISTIIKQELTEGRALALS

HTYANVSISHVINLWGADFNAEGNLEATYVTDSDANASIGMKKYFVGINAHGHVAISAKKIEGENIGAQVLGLFT
LSSGKDIWQKLS (pCART210)

SEQ ID NO: 16

DDYQRNATEAYAKEVPHQITSVWTKGVTPPEQFTQGEDVIHAPYLANQGWYDITKAFDGKDNLLCGAATAGNMLH
WWFDQNKTEIEAYLSKHPEKQKIIFRNQELFDLKEAIRTKDSQTNSQLFEYFRDKAFPYLSARQLGVMPDLVLDM
FINGYYLNVFKTQSTDVKRPYQDKDKRGGIFDAVFTRGNQTTLLTARHDLKNKGLNDISTIIKEELTKGRALALS
HTYANVSISHVINLWGADFNAEGNLEATYVTDSDANASIGMKKYFVGINKHGHVAISAKKIEGENIGAQVLGLFT
LSSGKDIWQKLN (pCART217)

SEQ ID NO: 17

SVWTKGVTPPEQFTQGEDVIHAPYLAHQGWYDITKAFDGKDNLLCGAATAGNMLHWWFDQNKTEIEAYLSKHPEK
QKIIFRNQELFDLKAAIDTKDSQTNSQLFNYFRDKAFPNLSARQLGVMPDLVLDMFINGYYLNVFKTQSTDVNRP
YQDKDKRGGIFDAVFTRGNQTTLLTARHDLKNKGLNDISTIIKQELTEGRALALSHTYANVSISHVINLWGADFN
AEGNLEATYVTDSDANASIGMKKYFVGINAHGHVAISAKKIEGENIGAQVLGLFTLSSGKDIWQKLS (pCART219)

SEQ ID NO: 18

DDYQRNATEAYAKEVPHQITSVWTKGVTPPEQFTQGEDVIHAPYLAHQGWYDITKAFDGADNLLCGAATAGNMLH
WWFDQNKTEIEAYLSKHPEKQKIIFRNQELFDLKAAIDTKDSQTNSQLFNYFRDKAFPNLSARQLGVMPDLVLDM
FINGYYLNVFKTQSTDVNRPYQDKDKRGGIFDAVFTRGNQTTLLTARHDLKNKGLNDISTIIKQELTEGRALALS
HTYANVSISHVINLWGADFNAEGNLEATYVTDSDANASIGMKKYFVGINAHGHVAISAKKIEGENIGAQVLGLFT
LSSGKDIWQKLS (pCART226)

SEQ ID NO: 19

SVWTKGVTPPEQFTQGEDVIHAPYLAHQGWYDITKAFDGADNLLCGAATAGNMLHWWFDQNKTEIEAYLSKHPEK
QKIIFRNQELFDLKAAIDTKDSQTNSQLFNYFRDKAFPNLSARQLGVMPDLVLDMFINGYYLNVFKTQSTDVNRP
YQDKDKRGGIFDAVFTRGNQTTLLTARHDLKNKGLNDISTIIKQELTEGRALALSHTYANVSISHVINLWGADFN
AEGNLEATYVTDSDANASIGMKKYFVGINAHGHVAISAKKIEGENIGAQVLGLFTLSSGKDIWQKLS (pCART229)

SEQ ID NO: 20

DDYQRNATEAYAKEVPHQITSVWTKGVTPPEQFTQGEDVIHAPYLAHQGWYDITKAFDGKDNLLCGAATAGNMLH
WWFDQNKTEIEAYLSKHPEKQKIIFRNQELFDLKAAIDTKDSQTNSQLFNYFRDKAFPNLSARQLGVMPDLVLDM
FINGYYLNVFKTQSTDVNRPYQDKDKRGGIFDAVFTRGNQTTLLTARHDLKNKGLNDISTIIKQELTEGRALALS
HTYANVSISHVINLWGADFNAEGNLEATYVTDSDANASIGMKKYFVGINAHGHVAISAKKIEGENIGAQVLGLFT
LSSGKDIWQKLS (pCART191)

SEQ ID NO: 21

DDYQRNATEAYAKEVPHQITSVWTKGVTPLTPEQFTQGEDVFHAPYVANQGWYDITKAFDGKDNLLCGAATAGNM
LHWWFDQNKDQIKRYLEEHPEKQKINFNGENMFDVKKAIDTKNHQLDSKLFNYFKEKAFPYLSAKHLGVFPDHVI
DMFINGYRLSLTNHGPTPVKEGSKDPRGGIFDAVFTRGNQSKLLTSRHDFKNKNLNDISTIIKQELTKGKALGLS
HTYANVRINHVINLWGADFNAEGNLEATYVTDSDSNASIGMKKYFVGVNAHGHVAISAKKIEGENIGAQVLGLFT
LSTGQDSWQKLS (pCART192)

SEQ ID NO: 22

DDYQRNATEAYAKEVPHQITSVWTKGVTPLTPEQFTQGEDVFHAPYVANQGWYDITKAFDGKDNLLCGAATAGNM
LHWWFDQNKDQIKRYLEEHPEKQKINFRGENMFDVKEAIRTKNHQLDSKLFEYFKEKAFPYLSAKHLGVFPDHVI
DMFINGYRLSLTNHGPTPVKKGSKDPRGGIFDAVFTRGNQSKLLTSRHDFKNKNLNDISTIIKSELTNGKALGLS (pCART193)

SEQ ID NO: 23

DDYQRNATEAYAKEVPHQITSVWTKGVTPLTPEQFTQGEDVFHAPYVANQGWYDITKTFNGKDDLLCGAATAGNM

LHWWFDQNKDQIKRYLEEHPEKQKINFNGEQMFDVKEAIDTKNHQLDSKLFEYFKEKAFPYLSTKHLGVFPDHVI

DMFINGYRLSLTNHGPTPVKEGSKDPRGGIFDAVFTRGNQSKLLTSRHDFKEKNLKEISDLIKQELTEGKALGLS

HTYANVRINHVINLWGADFDAEGNLKAIYVTDSDSNASIGMKKYFVGVNAAGKVAISAKKIEGENIGAQVLGLFT

LSTGQDSWNQTS (pCART194)

SEQ ID NO: 24

DDYQRNATEAYAKEVPHQITSVWTKGVTPLTPEQFTQGEDVFHAPYVANQGWYDITKTFNGKDDLLCGAATAGNM

LHWWFDQNKDQIKRYLEEHPEKQKINFRGEQMFDVKEAIRTKNHQLDSKLFEYFKEKAFPYLSTKHLGVFPDHVI

DMFINGYRLSLINHGPTPVKKGSKDPRGGIFDAVFIRGNQSKLLTSRHDFKEKNLKEISDLIKEELTKGKALGLS

HIYANVRINHVINLWGADFDAEGNLKAIYVIDSDSNASIGMKKYFVGVNKAGKVAISAKKIEGENIGAQVLGLFT

LSTGQDSWNQTN (pCART205)

SEQ ID NO: 25

DDYQRNATEAYAKEVPHQITSVWTKGVIPPEQFTQGEDVIHAPYVANQGWYDITKAFDGKDNLLCGAATAGNMLH

WWFDQNKDQIKRYLEEHPEKQKINFRGEQMFDVKKAIDTKNHQLDSKLFNYFKEKAFPGLSARRIGVFPDHVIDM

FINGYRLSLINHGPTPVKEGSKDPRGGIFDAVFIRGNQSKLLTSRHDFKNKNLNDISTIIKQELTKGKALGLSHT

YANVSINHVINLWGADFNAEGNLEAIYVIDSDSNASIGMKKYFVGVNAHGHVAISAKKIEGENIGAQVLGLFILS

TGQDSWQKLS

The polypeptide of the invention may comprise, consist essentially, or consist of the sequence of any one of SEQ ID NOs: 6 to 25. Each of SEQ ID NOs: 6 to 25 may optionally include an additional methionine at the N terminus and/or a histidine tag at the C terminus. The histidine tag is preferably consists of six histidine residues. The histidine tag is preferably linked to the C terminus by a linker of 3× glycine or 5× glycine residues.

Production of Polypeptides

A polypeptide as disclosed herein may be produced by any suitable means. For example, the polypeptide may be synthesised directly using standard techniques known in the art, such as Fmoc solid phase chemistry, Boc solid phase chemistry or by solution phase peptide synthesis. Alternatively, a polypeptide may be produced by transforming a cell, typically a bacterial cell, with a nucleic acid molecule or vector which encodes said polypeptide. Production of polypeptides by expression in bacterial host cells is described below and is exemplified in the Examples. The invention provides nucleic acid molecules and vectors which encode a polypeptide of the invention. The invention also provides a host cell comprising such a nucleic acid or vector. Exemplary polynucleotide molecules encoding polypeptides disclosed herein are provided as SEQ ID NOs: 33 to 55. Each of these sequences includes at the 3' end a codon for the N terminal methionine (ATG) and, prior to the stop codon (TAA) at the 5' end, codons for a 3×gly linker and a 6×his histidine tag, which may optionally be excluded.

The terms "nucleic acid molecule" and "polynucleotide" are used interchangeably herein and refer to a polymeric form of nucleotides of any length, either deoxyribonucleotides or ribonucleotides, or analogs thereof. Non-limiting examples of polynucleotides include a gene, a gene fragment, messenger RNA (mRNA), cDNA, recombinant polynucleotides, plasmids, vectors, isolated DNA of any sequence, isolated RNA of any sequence, nucleic acid probes, and primers. A polynucleotide of the invention may be provided in isolated or substantially isolated form. By substantially isolated, it is meant that there may be substantial, but not total, isolation of the polypeptide from any surrounding medium. The polynucleotides may be mixed with carriers or diluents which will not interfere with their intended use and still be regarded as substantially isolated. A nucleic acid sequence which "encodes" a selected polypeptide is a nucleic acid molecule which is transcribed (in the case of DNA) and translated (in the case of mRNA) into a polypeptide in vivo when placed under the control of appropriate regulatory sequences, for example in an expression vector. The boundaries of the coding sequence are determined by a start codon at the 5' (amino) terminus and a translation stop codon at the 3' (carboxy) terminus. For the purposes of the invention, such nucleic acid sequences can include, but are not limited to, cDNA from viral, prokaryotic or eukaryotic mRNA, genomic sequences from viral or prokaryotic DNA or RNA, and even synthetic DNA sequences. A transcription termination sequence may be located 3' to the coding sequence.

Polynucleotides can be synthesised according to methods well known in the art, as described by way of example in Sambrook et al (1989, Molecular Cloning—a laboratory manual; Cold Spring Harbor Press). The nucleic acid molecules of the present invention may be provided in the form of an expression cassette which includes control sequences operably linked to the inserted sequence, thus allowing for expression of the polypeptide of the invention in vivo. These expression cassettes, in turn, are typically provided within vectors (e.g., plasmids or recombinant viral vectors). Such an expression cassette may be administered directly to a host subject. Alternatively, a vector comprising a polynucleotide of the invention may be administered to a host subject. Preferably the polynucleotide is prepared and/or administered using a genetic vector. A suitable vector may be any vector which is capable of carrying a sufficient amount of genetic information, and allowing expression of a polypeptide of the invention.

The present invention thus includes expression vectors that comprise such polynucleotide sequences. Such expression vectors are routinely constructed in the art of molecular biology and may for example involve the use of plasmid DNA and appropriate initiators, promoters, enhancers and other elements, such as for example polyadenylation signals which may be necessary, and which are positioned in the correct orientation, in order to allow for expression of a peptide of the invention. Other suitable vectors would be apparent to persons skilled in the art. By way of further example in this regard we refer to Sambrook et al.

The invention also includes cells that have been modified to express a polypeptide of the invention. Such cells typically include prokaryotic cells such as bacterial cells, for example E. coli. Such cells may be cultured using routine methods to produce a polypeptide of the invention.

A polypeptide may be derivatised or modified to assist with their production, isolation or purification. For example, where a polypeptide of the invention is produced by recombinant expression in a bacterial host cell, the sequence of the polypeptide may include an additional methionine (M) residue at the N terminus to improve expression. As another example, the polypeptide of the invention may be derivatised or modified by addition of a ligand which is capable of binding directly and specifically to a separation means. Alternatively, the polypeptide may be derivatised or modified by addition of one member of a binding pair and the separation means comprises a reagent that is derivatised or modified by addition of the other member of a binding pair. Any suitable binding pair can be used. In a preferred embodiment where the polypeptide for use in the invention is derivatised or modified by addition of one member of a binding pair, the polypeptide is preferably histidine-tagged or biotin-tagged. Typically the amino acid coding sequence of the histidine or biotin tag is included at the gene level and the polypeptide is expressed recombinantly in E. coli. The histidine or biotin tag is typically present at either end of the polypeptide, preferably at the C-terminus. It may be joined directly to the polypeptide or joined indirectly by any suitable linker sequence, such as 3, 4 or 5 glycine residues. The histidine tag typically consists of six histidine residues, although it can be longer than this, typically up to 7, 8, 9, 10 or 20 amino acids or shorter, for example 5, 4, 3, 2 or 1 amino acids.

The amino acid sequence of a polypeptide may be modified to include non-naturally occurring amino acids, for example to increase stability. When the polypeptides are produced by synthetic means, such amino acids may be introduced during production. The polypeptides may also be modified following either synthetic or recombinant production. Polypeptides may also be produced using D-amino acids. In such cases the amino acids will be linked in reverse sequence in the C to N orientation. This is conventional in the art for producing such polypeptides.

A number of side chain modifications are known in the art and may be made to the side chains of the polypeptides, subject to the polypeptides retaining any further required activity or characteristic as may be specified herein. It will also be understood that polypeptides may be chemically modified, e.g. post-translationally modified. For example, they may be glycosylated, phosphorylated or comprise modified amino acid residues.

The polypeptide may be PEGylated. The polypeptide of the invention may be in a substantially isolated form. It may be mixed with carriers or diluents (as discussed below) which will not interfere with the intended use and still be regarded as substantially isolated. It may also be in a substantially purified form, in which case it will generally comprise at least 90%, e.g. at least 95%, 98% or 99%, of the protein in the preparation.

Compositions and Formulations Comprising Polypeptides

In another aspect, the present invention provides compositions comprising a polypeptide of the invention. For example, the invention provides a composition comprising one or more polypeptides of the invention, and at least one pharmaceutically acceptable carrier or diluent. The carrier (s) must be 'acceptable' in the sense of being compatible with the other ingredients of the composition and not deleterious to a subject to which the composition is administered. Typically, carriers and the final composition, are sterile and pyrogen free.

Formulation of a suitable composition can be carried out using standard pharmaceutical formulation chemistries and methodologies all of which are readily available to the reasonably skilled artisan. For example, the agent can be combined with one or more pharmaceutically acceptable excipients or vehicles. Auxiliary substances, such as wetting or emulsifying agents, pH buffering substances, reducing agents and the like, may be present in the excipient or vehicle. Suitable reducing agents include cysteine, thioglycerol, thioreducin, glutathione and the like. Excipients, vehicles and auxiliary substances are generally pharmaceutical agents that do not induce an immune response in the individual receiving the composition, and which may be administered without undue toxicity. Pharmaceutically acceptable excipients include, but are not limited to, liquids such as water, saline, polyethyleneglycol, hyaluronic acid, glycerol, thioglycerol and ethanol. Pharmaceutically acceptable salts can also be included therein, for example, mineral acid salts such as hydrochlorides, hydrobromides, phosphates, sulfates, and the like; and the salts of organic acids such as acetates, propionates, malonates, benzoates, and the like. A thorough discussion of pharmaceutically acceptable excipients, vehicles and auxiliary substances is available in Remington's Pharmaceutical Sciences (Mack Pub. Co., N.J. 1991).

Such compositions may be prepared, packaged, or sold in a form suitable for bolus administration or for continuous administration. Injectable compositions may be prepared, packaged, or sold in unit dosage form, such as in ampoules or in multi-dose containers containing a preservative. Compositions include, but are not limited to, suspensions, solutions, emulsions in oily or aqueous vehicles, pastes, and implantable sustained-release or biodegradable formulations. Such compositions may further comprise one or more additional ingredients including, but not limited to, suspending, stabilizing, or dispersing agents. In one embodiment of a composition for parenteral administration, the active ingredient is provided in dry (for e.g., a powder or granules) form for reconstitution with a suitable vehicle (e. g., sterile pyrogen-free water) prior to parenteral administration of the reconstituted composition. The compositions may be prepared, packaged, or sold in the form of a sterile injectable aqueous or oily suspension or solution. This suspension or solution may be formulated according to the known art, and may comprise, in addition to the active ingredient, additional ingredients such as the dispersing agents, wetting agents, or suspending agents described herein. Such sterile injectable formulations may be prepared using a non-toxic parenterally-acceptable diluent or solvent, such as water or 1,3-butane diol, for example. Other acceptable diluents and solvents include, but are not limited to, Ringer's solution, isotonic sodium chloride solution, and fixed oils such as synthetic mono- or di-glycerides.

Other parentally-administrable compositions which are useful include those which comprise the active ingredient in microcrystalline form, in a liposomal preparation, or as a component of a biodegradable polymer systems. Compositions for sustained release or implantation may comprise pharmaceutically acceptable polymeric or hydrophobic materials such as an emulsion, an ion exchange resin, a sparingly soluble polymer, or a sparingly soluble salt. The compositions may be suitable for administration by any suitable route including, for example, intradermal, subcutaneous, percutaneous, intramuscular, intra-arterial, intraperitoneal, intraarticular, intraosseous or other appropriate administration routes. Preferred compositions are suitable for administration by intravenous infusion.

Methods of Use of Polypeptides

The invention provides for the use of polypeptides of the invention in various methods. For example, the present polypeptides may provide useful tools for biotechnology. The polypeptides may be used for specific ex vivo cleavage of IgG, in particular human IgG. In such a method, the polypeptide may be incubated with a sample containing IgG under conditions which permit the specific cysteine protease activity to occur. Specific cleavage can be verified, and the cleavage products isolated using any suitable method, such as those described in WO2003051914 and WO2009033670. Thus the method can be used in particular to generate Fc and F(ab')$_2$ fragments. Fab fragments may then be produced by carrying out a reduction step (for example in 2-mercaptoethanolamine or Cystamine) on the F(ab')$_2$ fragments that result from cleavage of IgG with a polypeptide of the invention.

The method may also be used to detect or analyse IgG in a sample, or to remove IgG from a sample. A method for the detection of IgG in a sample typically involves incubating the polypeptide with the sample under conditions which permit IgG-specific binding and cleavage. The presence of IgG can be verified by detection of the specific IgG cleavage products, which may subsequently be analysed.

The polypeptides in accordance with the present invention may also be used in therapy or prophylaxis. In therapeutic applications, polypeptides or compositions are administered to a subject already suffering from a disorder or condition, in an amount sufficient to cure, alleviate or partially arrest the condition or one or more of its symptoms. Such therapeutic treatment may result in a decrease in severity of disease symptoms, or an increase in frequency or duration of symptom-free periods. An amount adequate to accomplish this is defined as "therapeutically effective amount". In prophylactic applications, polypeptides or compositions are administered to a subject not yet exhibiting symptoms of a disorder or condition, in an amount sufficient to prevent or delay the development of symptoms. Such an amount is defined as a "prophylactically effective amount". The subject may have been identified as being at risk of developing the disease or condition by any suitable means. Thus the invention also provides a polypeptide of the invention for use in the treatment of the human or animal body. Also provided herein is a method of prevention or treatment of disease or condition in a subject, which method comprises administering a polypeptide of the invention to the subject in a prophylactically or therapeutically effective amount. The polypeptide may be co-administered with an immune-suppressive agent. The polypeptide is preferably administered by intravenous infusion, but may be administered by any suitable route including, for example, intradermal, subcutaneous, percutaneous, intramuscular, intra-arterial, intraperitoneal, intraarticular, intraosseous or other appropriate administration routes. The amount of said polypeptide that is administered may be between 0.01 mg/kg BW and 2 mg/kg BW, between 0.04 and 2 mg/kg BW, between 0.12 mg/kg BW and 2 mg/kg BW, preferably between 0.24 mg/kg and 2 mg/kg BW and most preferably between 1 mg/kg and 2 mg/kg BW. The polypeptide may be administered on multiple occasions to the same subject, provided that the quantity of ADA in the serum of the subject which is capable of binding to the polypeptide does not exceed a threshold determined by the clinician. The quantity of ADA in the serum of the subject which is capable of binding to the polypeptide may be determined by any suitable method, such as an agent specific CAP FEIA (ImmunoCAP) test or a titre assay.

Polypeptides of the invention may be particularly useful in the treatment or prevention of a disease or condition mediated by pathogenic IgG antibodies. Accordingly, the invention provides a polypeptide of the invention for use in the treatment or prevention of a disease or condition mediated by pathogenic IgG antibodies. The invention also provides a method of treating or preventing a disease or condition mediated by pathogenic IgG antibodies comprising administering to an individual a polypeptide of the invention. The method may comprise repeat administration of the said polypeptide. The invention also provides a polypeptide of the invention for use in the manufacture of a medicament for the treatment or prevention of a disease or condition mediated by pathogenic IgG antibodies, particularly an autoimmune disease which is mediated in whole or in part by pathogenic IgG antibodies.

The pathogenic antibodies may typically be specific for an antigen which is targeted in an autoimmune disease or other condition mediated wholly or in part by antibodies. Table D sets out a list of such diseases and the associated antigens. A polypeptide of the invention may be used to treat any of these diseases or conditions. The polypeptide is particularly effective for the treatment or prevention of autoimmune disease which is mediated in whole or in part by pathogenic IgG antibodies.

TABLE D

| DISEASE | AUTOANTIGENS |
|---|---|
| Addison's disease | Steroid 21-hydroxylase, 17 alpha-Hydroxylase (17OH) and side-chain-cleavage enzyme (P450scc), Thyroperoxidase, thyroglobulin and H+/K(+)– |
| Anti-GBM glomerulonephritis (related to Goodpasteur) | Anti-glomerular basement membrane (anti-GBM): noncollagenous (NC1) domains of the alpha3alpha4alpha5(IV) collagen |

TABLE D-continued

| DISEASE | AUTOANTIGENS |
|---|---|
| Anti-neutrophil cytoplasmic antibody-associated vasculitides (ANCA associated vasculitis)(Wegener granulomatosis, Churg-Strauss syndrome, microscopic polyangiitis) | Myeloperoxidase, proteinase 3 |
| Anti-NMDAR Encephalitis | N-methyl-D-aspartate receptor (NMDAR) |
| Anti-phospholipid antibody syndrome (APS) and catastrophic APS | Negatively-charged phospholipids complexed with phospholipid binding plasma proteins (e.g. beta2GPI), cardiolipin, beta2-glycoprotein I, and (beta2GPI) |
| Autoimmune bullous skin diseases (Pemphigus). Pemphigus foliaceus (PF), fogo selvagem (FS)(endemic form), pemphigus vulgaris (PV) | IgG against keratinocytes. Specific target is desmoglein (Dsg) 1 (desmosomal Cadherins) |
| Autoimmune hemolytic anemia (AIHA) | Self-antigens on red-blood-cells |
| Autoimmune hepatitis (AIH) | Actin, antinuclear antibody (ANA), smooth muscle antibody (SMA), liver/kidney microsomal antibody (LKM-1), anti soluble liver antigen (SLA/LP) and anti-mitochondrial antibody (AMA), CYP2D6, CYP2C9-tienilic acid, UGT1A, CYP1A2, CYP2A6, CYP3A, CYP2E1, CYP11A1, CYP17 and CYP21 |
| Autoimmune neutropenia (AIN) | FcgRIIIb |
| Bullous pemphigoid (BP) | Hemidesmosomal proteins BP230 and BP180 (type XVII collagen), laminin 5, the alpha6 subunit of the integrin alpha6beta4 and p200 |
| Celiac disease | transglutaminase 2 (TG2), transglutaminase 3, actin, ganglioside, collagen, calreticulin and zonulin, thyroid, endocrine pancreas, anti-gastric and liver, anti-nuclear constituents, anti-reticulin, actin, smooth muscle, calreticulin, desmin, collagens, bone, anti-brain, ganglioside, neuronal, blood vessel |
| Chronic utricaria | Alpha-subunit of the high-affinity IgE receptor, IgE |
| Complete congenital heart block (CCHB) | Ro (Sjögens syndrome antigen A (SSA)), La (Sjögens syndrome antigen B(SSB)) |
| Diabetes type 1A (T1DM) | Islet cell autoantibodies (ICA), antibodies to insulin (IAA), glutamic acid decarboxylase (GAA or GAD), protein tyrosine phosphatase (IA2 or ICA512), Insulinoma Associated Peptide-2. The number of antibodies, rather than the individual antibody, is thought to be most predictive of progression to overt diabetes. |
| Epidermolysis bullosa acquisita (EBA) | The 145-kDa noncollagenous aminoterminal (NC-1) domain of collagen VII |
| Essential mixed cryoglubulinemia | Essential mixed cryoglobulinemia antigens |
| Goodpasture's syndrome (also known as Goodpasture's disease and anti-glomerular basement membrane disease | alpha3(IV) collagen (=Goodpasture antigen) |
| Graves'disease (Basedow's disease), includes Goitre and hyperthyroidism, infiltrative exopthalmos and infiltarative dermopathy. | Thyrotropin receptor (TSHR) Thyroid peroxidase (TPO) |
| Guillain-Barré syndrome (GBS). Acute inflammatory demyelinating polyneuropathy (AIDP), acute motor axonal neuropathy (AMAN) | Gangliosides GM1, GM1b, GD1a, and GalNAc-GD1a, glycosphingolipid, myelin proteins PMP22 and P0 |
| Hemophilia - Acquired FVIII deficiency | Factor VIII |
| Idiopathic thrombocytopenic purpura (ITP) | Platelet glycoprotein (GP) IIb-IIIa and/or GPIb-IX |
| Lambert-Eaton myasthenic syndrome (LEMS) | voltage gated calcium channels |
| Mixed Connective Tissue Disease (MCTD) | IgG directed against the spliceosome, U1-snRNP |
| Multiple Myeloma | Multiple Myeloma antigens |
| Myasthenia gravis Myasthenic crisis | Acetylcholine receptors (AchR), muscle-specific kinase (MuSK) |
| Myocarditis, dilated cardiomyopathy (DCM)(congestive cardiomyopathy) | heart-reactive autoantibodies against multiple antigens e.g. cardiac myosin |
| Neuromyelitis Optica (NMO) | Aquaporin 4 (AQP4) |
| Primary biliary cirrhosis (PBC) | pyruvate dehydrogenase complex (PDC)-E2 and other members of the oxaloacid dehydrogenase family, Glycoprotein-210, p62, sp100 |
| Primary Progressive Multiple Sclerosis (PPMS) | Myelin oligodendrocyte glycoprotein (MOG), Myelin proteolipid protein (PLP), transketolase (TK), cyclic nucleotide phosphodiesterase type I (CNPase I), collapsin response mediator protein 2, tubulin beta4, neurofascin |

TABLE D-continued

| DISEASE | AUTOANTIGENS |
|---|---|
| Rheumatic heart disease (RHD), (Rheumatic fever) | Cardiac myosin |
| Rheumatoid Arthritis (RA) | Type II collagen, citrullin (-ated proteins (e.g. (fibrinogen, vimentin, filaggrin, type II collagen, enolase)), G6PI, RFs (anti-Fc/IgG), Vimentin, and cytokeratin |
| Seram-sickness, immune complex hypersensitivity (type III) | Various antigens |
| Sjögren Syndrome (SS) | Ro (Sjögens syndrome antigen A (SS-A)), La (Sjögens syndrome antigen B(SS-B)), p80 coilin, antinuclear antibodies, anti-thyroid, anti-centromere antibodies (Raynaud's phenomenon), anti-carbonic anhydrase II (distal renal tubular acidosis), anti-mitochondrial antibodies (liver pathology), cryoglobulins (evolution to non-Hodgkin's lymphoma). alpha- and beta-fodrin, islet cell autoantigen, poly(ADP)ribose polymerase (PARP), NuMA, Golgins, NOR-90, M3-muscarinic receptor |
| SLE including Lupus nephritis | Autoantibodies to nuclear constituents (e.g. dsDNA and nucleosomes), dsDNA, PARP, Sm, PCDA, rRNA Ribosome P proteins, C1q |
| Stiff-person syndrome (SPS) | glutamic acid decarboxylase (GAD), amphiphysin. |
| Systemic sclerosis (scleroderma) | DNA-topoisomerase I (Scl-70), U3 snRNP, U2 snRNP, 7-2 RNP, NOR-90, centromere-associated proteins, and nucleolar antigens, Anti-Th/To, Anti-RNA polymerase I/III, Anti-PDGF receptor, Anti-fibrillin-1, M3-muscarinic receptor, |
| Transplant rejection | Transplant rejection antigens |
| Thrombotic Thrombocytopenic Purpura (TTP) | ADAMTS13 |

In another embodiment, a polypeptide of the invention may be used in a method to improve the benefit to a subject of a therapy or a therapeutic agent. The method comprises two steps, which are referred to herein as steps (a) and (b).

Step (a) comprises administering to the subject a polypeptide of the invention. The amount of the polypeptide administered is preferably sufficient to cleave substantially all IgG molecules present in the plasma of the subject. Step (b) comprises subsequently administering to the subject the said therapy or therapeutic agent. Steps (a) and (b) are separated by a time interval which is preferably sufficient for cleavage of substantially all IgG molecules present in the plasma of the subject to take place. The said interval may typically be of at least 30 minutes and at most 21 days.

The therapeutic agent of which the benefit is improved is typically an antibody which is administered for the treatment of cancer or another disease. The therapeutic agent may be IVIg. In the context of this embodiment, the invention may be alternatively described as providing a method for the treatment of cancer or another disease in a subject, the method comprising (a) administering to the subject a polypeptide of the invention; and (b) subsequently administering to the subject a therapeutically effective amount of an antibody which is a treatment for said cancer or said other disease; wherein:

the amount of said polypeptide administered is sufficient to cleave substantially all IgG molecules present in the plasma of the subject; and
steps (a) and (b) are separated by a time interval of at least 2 hours and at most 21 days.

In other words, the invention also provides the polypeptide for use in such a method for the treatment of cancer or another disease. The invention also provides use of the agent in the manufacture of a medicament for the treatment of cancer or another disease by such a method. The cancer may be Acute lymphoblastic leukemia, Acute myeloid leukemia, Adrenocortical carcinoma, AIDS-related cancers, AIDS-related lymphoma, Anal cancer, Appendix cancer, Astrocytoma, childhood cerebellar or cerebral, Basal cell carcinoma, Bile duct cancer, extrahepatic, Bladder cancer, Bone cancer, Osteosarcoma/Malignant fibrous histiocytoma, Brainstem glioma, Brain cancer, Brain tumor, cerebellar astrocytoma, Brain tumor, cerebral astrocytoma/malignant glioma, Brain tumor, ependymoma, Brain tumor, medulloblastoma, Brain tumor, supratentorial primitive neuroectodermal tumors, Brain tumor, visual pathway and hypothalamic glioma, Breast cancer, Bronchial adenomas/carcinoids, Burkitt lymphoma, Carcinoid tumor, Carcinoid tumor, gastrointestinal, Carcinoma of unknown primary, Central nervous system lymphoma, Cerebellar astrocytoma, Cerebral astrocytoma/ Malignant glioma, Cervical cancer, Chronic lymphocytic leukemia, Chronic myelogenous leukemia Chronic myeloproliferative disorders, Colon Cancer, Cutaneous T-cell lymphoma, Desmoplastic small round cell tumor, Endometrial cancer, Ependymoma, Esophageal cancer, Ewing's sarcoma in the Ewing family of tumors, Extracranial germ cell tumor, Childhood, Extragonadal Germ cell tumor, Extrahepatic bile duct cancer, Eye Cancer, Intraocular melanoma, Eye Cancer, Retinoblastoma, Gallbladder cancer, Gastric (Stomach) cancer, Gastrointestinal Carcinoid Tumor, Gastrointestinal stromal tumor (GIST), Germ cell tumor: extracranial, extragonadal, or ovarian, Gestational trophoblastic tumor, Glioma of the brain stem, Glioma, Childhood Cerebral Astrocytoma, Glioma, Childhood Visual Pathway and Hypothalamic, Gastric carcinoid, Hairy cell leukemia, Head and neck cancer, Heart cancer, Hepatocellular (liver) cancer, Hodgkin lymphoma, Hypopharyngeal cancer, Hypothalamic and visual pathway glioma, Intraocular Melanoma, Islet Cell Carcinoma (Endocrine Pancreas), Kaposi sarcoma, Kidney cancer (renal cell cancer), Laryngeal Cancer, Leukemias, Leukemia, acute lymphoblastic (also called acute lymphocytic leukemia), Leukemia, acute myeloid (also called acute myelogenous leukemia), Leukemia, chronic lymphocytic (also called chronic lymphocytic leukemia), Leukemia, chronic myelogenous (also called chronic myeloid leukemia), Leukemia, hairy cell, Lip and Oral Cavity Cancer, Liposarcoma, Liver Cancer (Primary), Lung Cancer, Non-Small Cell Lung Cancer, Small Cell, Lymphomas, Lymphoma, AIDS-related, Lymphoma, Burkitt, Lymphoma, cutaneous T-Cell, Lymphoma, Hodgkin, Lymphomas, Non-Hodgkin (an old classification of all lymphomas except Hodgkin's), Lymphoma, Primary Central Nervous System, Macroglobulinemia, Waldenström, Malignant Fibrous Histiocytoma of Bone/Osteosarcoma, Medulloblastoma, Melanoma, Melanoma, Intraocular (Eye), Merkel Cell Carcinoma, Mesothelioma, Adult Malignant, Mesothelioma, Metastatic Squamous Neck Cancer with Occult Primary, Mouth Cancer, Multiple Endocrine Neoplasia Syndrome, Multiple Myeloma/Plasma Cell Neoplasm, Mycosis Fungoides, Myelodysplastic Syndromes, Myelodysplastic/Myeloproliferative Diseases, Myelogenous Leukemia, Chronic, Myeloid Leukemia, Adult Acute, Myeloid Leukemia, Childhood Acute, Myeloma, Multiple (Cancer of the Bone-Marrow), Myeloproliferative Disorders, Nasal cavity and paranasal sinus cancer, Nasopharyngeal carcinoma, Neuroblastoma, Non-Hodgkin lymphoma, Non-small cell lung cancer, Oral Cancer, Oropharyngeal cancer, Osteosarcoma/malignant fibrous histiocytoma of bone, Ovarian cancer, Ovarian epithelial cancer (Surface epithelial-stromal tumor), Ovarian germ cell tumor, Ovarian low malignant potential tumor, Pancreatic cancer, Pancreatic cancer, islet cell, Paranasal sinus and nasal cavity cancer, Parathyroid cancer, Penile cancer, Pharyngeal cancer, Pheochromocytoma, Pineal astrocytoma, Pineal germinoma, Pineoblastoma and supratentorial primitive neuroectodermal tumors, Pituitary adenoma, Plasma cell neoplasia/Multiple myeloma, Pleuropulmonary blastoma, Primary central nervous system lymphoma, Prostate cancer, Rectal cancer, Renal cell carcinoma (kidney cancer), Renal pelvis and ureter, transitional cell cancer, Retinoblastoma, Rhabdomyosarcoma, Salivary gland cancer, Sarcoma, Ewing family of tumors, Kaposi Sarcoma, Sarcoma, soft tissue, Sarcoma, uterine, Sézary syndrome, Skin cancer (nonmelanoma), Skin cancer (melanoma), Skin carcinoma, Merkel cell, Small cell lung cancer, Small intestine cancer, Soft tissue sarcoma, Squamous cell carcinoma, Squamous neck cancer with occult primary, metastatic, Stomach cancer, Supratentorial primitive neuroectodermal tumor, T-Cell lymphoma, cutaneous—see Mycosis Fungoides and Sezary syndrome, Testicular cancer, Throat cancer, Thymoma, Thymoma and Thymic carcinoma, Thyroid cancer, Thyroid cancer, Transitional cell cancer of the renal pelvis and ureter, Trophoblastic tumor, Ureter and renal pelvis, transitional cell cancer Urethral cancer, Uterine cancer, endometrial, Uterine sarcoma, Vaginal cancer, Visual pathway and hypothalamic glioma, Vulvar cancer, Waldenström macroglobulinemia and Wilms tumor (kidney cancer).

The cancer is preferably prostate cancer, breast cancer, bladder cancer, colon cancer, rectal cancer, pancreatic cancer, ovarian cancer, lung cancer, cervical cancer, endometrial cancer, kidney (renal cell) cancer, oesophageal cancer, thyroid cancer, skin cancer, lymphoma, melanoma or leukemia.

The antibody administered in step (b) is preferably specific for a tumour antigen associated with one or more of the above cancer types. Targets of interest for an antibody for use in the method include CD2, CD3, CD19, CD20, CD22, CD25, CD30, CD32, CD33, CD40, CD52, CD54, CD56, CD64, CD70, CD74, CD79, CD80, CD86, CD105, CD138, CD174, CD205, CD227, CD326, CD340, MUC16, GPNMB, PSMA, Cripto, ED-B, TMEFF2, EphA2, EphB2, FAP, av integrin, Mesothelin, EGFR, TAG-72, GD2, CA1X, 5T4, α4β7 integrin, Her2. Other targets are cytokines, such as interleukins IL-I through IL-13, tumour necrosis factors α & β, interferons α, β and γ, tumour growth factor Beta (TGF-β), colony stimulating factor (CSF) and granulocyte monocyte colony stimulating factor (GMCSF). See Human Cytokines: Handbook for Basic & Clinical Research (Aggrawal et al. eds., Blackwell Scientific, Boston, Mass. 1991). Other targets are hormones, enzymes, and intracellular and intercellular messengers, such as, adenyl cyclase, guanyl cyclase, and phospholipase C. Other targets of interest are leukocyte antigens, such as CD20, and CD33. Drugs may also be targets of interest. Target molecules can be human, mammalian or bacterial. Other targets are antigens, such as proteins, glycoproteins and carbohydrates from microbial pathogens, both viral and bacterial, and tumors. Still other targets are described in U.S. Pat. No. 4,366,241.

The antibody may be attached directly or indirectly to a cytotoxic moiety or to a detectable label. The antibody may be administered via one or more routes of administration using one or more of a variety of methods known in the art. The route and/or mode of administration will vary depending upon the desired results. Preferred routes of administration for antibodies include intravenous, intramuscular, intradermal, intraperitoneal, subcutaneous, spinal or other parenteral routes of administration, for example by injection or infusion. The phrase "parenteral administration" as used herein means modes of administration other than enteral and topical administration, usually by injection. Alternatively, an antibody can be administered via a non-parenteral route, such as a topical, epidermal or mucosal route of administration. Local administration is also preferred, including peritumoral, juxtatumoral, intratumoral, intralesional, perilesional, intra cavity infusion, intravesicle administration, and inhalation.

A suitable dosage of an antibody of the invention may be determined by a skilled medical practitioner. Actual dosage levels of an antibody may be varied so as to obtain an amount of the active ingredient which is effective to achieve the desired therapeutic response for a particular patient, composition, and mode of administration, without being toxic to the patient. The selected dosage level will depend upon a variety of pharmacokinetic factors including the activity of the particular antibody employed, the route of administration, the time of administration, the rate of excretion of the antibody, the duration of the treatment, other drugs, compounds and/or materials used in combination with the particular compositions employed, the age, sex, weight, condition, general health and prior medical history of the patient being treated, and like factors well known in the medical arts.

A suitable dose of an antibody may be, for example, in the range of from about 0.1 μg/kg to about 100 mg/kg body weight of the patient to be treated. For example, a suitable dosage may be from about 1 μg/kg to about 10 mg/kg body weight per day or from about 10p g/kg to about 5 mg/kg body weight per day.

Dosage regimens may be adjusted to provide the optimum desired response (e.g., a therapeutic response). For example, a single bolus may be administered, or step (b) of the method may comprise several divided doses administered over time or the dose may be proportionally reduced or increased as indicated by the exigencies of the therapeutic situation, provided the required interval between steps (a) and (b) is not exceeded. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier.

The antibody of step (b) may be administered in combination with chemotherapy or radiation therapy. The method may further comprises the administration of an additional anti-cancer antibody or other therapeutic agent, which may be administered together with the antibody of step (b) in a single composition or in separate compositions as part of a combined therapy. For example, the antibody of step (b) may be administered before, after or concurrently with the other agent.

The antibody may be Abagovomab, Abciximab, Actoxumab, Adalimumab, Adecatumumab, Afelimomab, Afutuzumab, Alacizumab pegol, ALD518, Alemtuzumab, Alirocumab, Altumomab pentetate, Amatuximab, Anatumomab mafenatox, Anrukinzumab, Apolizumab, Arcitumomab, Aselizumab, Atinumab, Atlizumab (=tocilizumab), Atorolimumab, Bapineuzumab, Basiliximab, Bavituximab, Bectumomab, Belimumab, Benralizumab, Bertilimumab, Besilesomab, Bevacizumab, Bezlotoxumab, Biciromab, Bimagrumab, Bivatuzumab mertansine, Blinatumomab, Blosozumab, Brentuximab vedotin, Briakinumab, Brodalumab, Canakinumab, Cantuzumab mertansine, Cantuzumab ravtansine, Caplacizumab, Capromab pendetide, Carlumab, Catumaxomab, CC49, Cedelizumab, Certolizumab pegol, Cetuximab, Ch.14.18, Citatuzumab bogatox, Cixutumumab, Clazakizumab, Clenoliximab, Clivatuzumab tetraxetan, Conatumumab, Concizumab, Crenezumab, CR6261, Dacetuzumab, Daclizumab, Dalotuzumab, Daratumumab, Demcizumab, Denosumab, Detumomab, Dorlimomab aritox, Drozitumab, Duligotumab, Dupilumab, Dusigitumab, Ecromeximab, Eculizumab, Edobacomab, Edrecolomab, Efalizumab, Efungumab, Elotuzumab Elsilimomab, Enavatuzumab, Enlimomab pegol, Enokizumab, Enoticumab, Ensituximab, Epitumomab cituxetan, Epratuzumab, Erlizumab, Ertumaxomab, Etaracizumab, Etrolizumab, Evolocumab, Exbivirumab, Fanolesomab, Faralimomab Farletuzumab, Fasinumab, FBTA05, Felvizumab, Fezakinumab, Ficlatuzumab, Figitumumab, Flanvotumab, Fontolizumab, Foralumab, Foravirumab, Fresolimumab, Fulranumab, Futuximab, Galiximab, Ganitumab, Gantenerumab, Gavilimomab, Gemtuzumab ozogamicin, Gevokizumab, Girentuximab, Glembatumumab vedotin, Golimumab, Gomiliximab, GS6624, Ibalizumab, Ibritumomab tiuxetan, Icrucumab, Igovomab, Imciromab, Imgatuzumab, Inclacumab, Indatuximab ravtansine, Infliximab, Intetumumab, Inolimomab, Inotuzumab ozogamicin, Ipilimumab, Iratumumab, Itolizumab, Ixekizumab, Keliximab, Labetuzumab, Lampalizumab, Lebrikizumab, Lemalesomab, Lerdelimumab, Lexatumumab, Libivirumab, Ligelizumab, Lintuzumab, Lirilumab, Lodelcizumab, Lorvotuzumab mertansine, Lucatumumab, Lumiliximab, Mapatumumab, Maslimomab, Mavrilimumab, Matuzumab, Mepolizumab, Metelimumab, Milatuzumab, Minretumomab, Mitumomab, Mogamulizumab, Morolimumab, Motavizumab, Moxetumomab pasudotox, Muromonab-CD3, Nacolomab tafenatox, Namilumab, Naptumomab estafenatox, Narnatumab, Natalizumab, Nebacumab, Necitumumab, Nerelimomab, Nesvacumab, Nimotuzumab, Nivolumab, Nofetumomab merpentan, Obinutuzumab, Ocaratuzumab, Ocrelizumab, Odulimomab, Ofatumumab, Olaratumab, Olokizumab, Omalizumab, Onartuzumab, Oportuzumab monatox, Oregovomab, Orticumab, Otelixizumab, Oxelumab, Ozanezumab, Ozoralizumab, Pagibaximab, Palivizumab, Panitumumab, Panobacumab, Parsatuzumab, Pascolizumab, Pateclizumab, Patritumab, Pemtumomab, Perakizumab, Pertuzumab, Pexelizumab, Pidilizumab, Pinatuzumab vedotin, Pintumomab, Placulumab, Polatuzumab vedotin, Ponezumab, Priliximab, Pritoxaximab, Pritumumab, PRO 140, Quilizumab, Racotumomab, Radretumab, Rafivirumab, Ramucirumab, Ranibizumab, Raxibacumab, Regavirumab, Reslizumab, Rilotumumab, Rituximab, Robatumumab, Roledumab, Romosozumab, Rontalizumab, Rovelizumab, Ruplizumab, Samalizumab, Sarilumab, Satumomab pendetide, Secukinumab, Seribantumab, Setoxaximab, Sevirumab, Sibrotuzumab, Sifalimumab, Siltuximab, Simtuzumab, Siplizumab, Sirukumab, Solanezumab, Solitomab, Sonepcizumab, Sontuzumab, Stamulumab, Sulesomab, Suvizumab, Tabalumab, Tacatuzumab tetraxetan, Tadocizumab, Talizumab, Tanezumab, Taplitumomab paptox, Tefibazumab, Telimomab aritox, Tenatumomab, Teneliximab, Teplizumab, Teprotumumab, TGN 1412, Ticilimumab (=tremelimumab), Tildrakizumab, Tigatuzumab, TNX-650, Tocilizumab (=atlizumab), Toralizumab, Tositumomab, Tralokinumab, Trastuzumab, TRBS07, Tregalizumab, Tremelimumab Tucotuzumab celmoleukin, Tuvirumab, Ublituximab, Urelumab, Urtoxazumab, Ustekinumab, Vapaliximab, Vatelizumab, Vedolizumab, Veltuzumab, Vepalimomab Vesencumab, Visilizumab, Volociximab, Vorsetuzumab mafodotin, Votumumab, Zalutumumab, Zanolimumab, Zatuximab, Ziralimumab or Zolimomab aritox.

Preferred antibodies include Natalizumab, Vedolizumab, Belimumab, Atacicept, Alefacept, Otelixizumab, Teplizumab, Rituximab, Ofatumumab, Ocrelizumab, Epratuzumab, Alemtuzumab, Abatacept, Eculizamab, Omalizumab, Canakinumab, Meplizumab, Reslizumab, Tocilizumab, Ustekinumab, Briakinumab, Etanercept, Inlfliximab, Adalimumab, Certolizumab pegol, Golimumab, Trastuzumab, Gemtuzumab, Ozogamicin, Ibritumomab, Tiuxetan, Tostitumomab, Cetuximab, Bevacizumab, Panitumumab, Denosumab, Ipilimumab, Brentuximab and Vedotin.

The therapy of which the benefit is improved is typically an organ transplant. The organ may be selected from kidney, liver, heart, pancreas, lung, or small intestine. The subject to be treated may preferably be sensitized or highly sensitised. By "sensitized" it is meant that the subject has developed antibodies to human major histocompatibility (MHC) antigens (also referred to as human leukocyte antigens (HLA)). The anti-HLA antibodies originate from allogenically sensitized B-cells and are usually present in patients that have previously been sensitized by blood transfusion, previous transplantation or pregnancy (Jordan et al., 2003).

Whether or not a potential transplant recipient is sensitized may be determined by any suitable method. For example, a Panel Reactive Antibody (PRA) test may be used to determine if a recipient is sensitized. A PRA score>30% is typically taken to mean that the patient is "high immulogic risk" or "sensitized". Alternatively, a cross match test may be conducted, in which a sample of the potential transplant donor's blood is mixed with that of the intended recipient. A positive cross-match means that the recipient has antibodies which react to the donor sample, indicating that the recipient is sensitized and transplantation should not occur. Cross-match tests are typically conducted as a final check immediately prior to transplantation.

The presence of high titer antibodies against MHC antigens of the potential donor (i.e. donor specific antibodies (DSA)) is a direct contraindication to transplantation because of the risk of acute antibody-mediated rejection. In short, sensitization to donor MHC antigens hampers the identification of a suitable donor. A positive cross-match test is an unambiguous barrier to transplantation. Since approximately one third of patients waiting for kidney transplantation are sensitized, with as many as 15% being highly sensitized, this leads to an accumulation of patients waiting for transplant. In the US, the median time on the waiting list for renal transplantation in 2001-2002 was 1329 days for those with Panel Reactive Antibody (PRA) score 0-9%, 1920 days for those with PRA 10-79%, and 3649 days for those with PRA 80% or greater (OPTN-database, 2011).

One accepted strategy to overcome the DSA barrier is to apply plasma exchange or immune adsorption, often in combination with e.g. intravenous gamma globulin (IVIg) or Rituximab, to lower the levels of DSA to a level where transplantation can be considered (Jordan et al., 2004; Montgomery et al., 2000; Vo et al., 2008a; Vo et al., 2008b). However, plasma exchange, immune adsorption and IVIg treatments have the disadvantage of being inefficient and requiring rigorous planning since they involve repeated treatments over an extended period of time. When an organ from a deceased donor becomes available it has to be transplanted within hours since prolonged cold ischemia time is one of the most important risk factors for delayed graft function and allograft loss in renal transplantation (Ojo et al., 1997).

By contrast, the method of the present invention allows the rapid, temporary and safe removal of DSAs in a potential transplant recipient. Administering the polypeptide of the invention just prior to transplantation has the capacity to effectively desensitize a highly sensitized patient, thereby allowing transplantation and avoiding acute antibody-mediated rejection. A single dose of polypeptide prior to transplantation will enable transplantation of thousands of patients with donor specific IgG antibodies.

In the context of this embodiment, the method may be alternatively described as a method for the treatment of organ failure in a subject, the method comprising (a) administering to the subject a polypeptide of the invention and (b) subsequently transplanting a replacement organ into the subject; wherein:

the amount of said polypeptide administered is sufficient to cleave substantially all IgG molecules present in the plasma of the subject; and steps (a) and (b) are separated by a time interval of at least 2 hours and at most 21 days.

In other words, this embodiment may be described as a method for preventing rejection of a transplanted organ in a subject, particularly acute antibody-mediated transplant rejection, the method comprising, at least 2 hours and at most 21 days prior to transplantation of the organ, administering to the subject a polypeptide of the invention, wherein the amount of said polypeptide administered is sufficient to cleave substantially all IgG molecules present in the plasma of the subject. The invention also provides use of the polypeptide of the invention in such a method of treating organ failure or preventing transplant rejection, particularly acute antibody-mediated transplant rejection. The invention also provides use of the polypeptide of the invention in the manufacture of a medicament for the treatment of organ failure or for the prevention of transplant rejection by such a method. In this embodiment, the method of the invention may additionally comprise a step conducted at or immediately prior to transplantation, which step comprises induction suppression of T cells and/or B cells in the patient. Said induction suppression may typically comprise administering an effective amount of an agent which kills or inhibits T cells, and/or administering an effective amount of an agent which kills or inhibits B cells. Agents which kill or inhibit T cells include Muromonab, Basiliximab, Daclizumab, an antithymocyte globulin (ATG) antibody and a lymphocyte immune globulin, anti-thymocyte globulin preparation (AT-GAM). Rituximab is known to kill or inhibit B cells.

EXAMPLES

Unless indicated otherwise, the methods used are standard biochemistry and molecular biology techniques. Examples of suitable methodology textbooks include Sambrook et al., Molecular Cloning, A Laboratory Manual (1989) and Ausubel et al., Current Protocols in Molecular Biology (1995), John Wiley and Sons, Inc.

Example 1—Design of Polypeptides, Production and Purification

The mature IdeS molecule was analysed and regions suitable for mutation were identified. In some cases an in silico assessment was used to evaluate the likely outcome of a mutation. Having decided on the sequence of each polypeptide, cDNA encoding each polypeptide were generated at GeneCust, Luxembourg either by site-directed mutation of a starting sequence or synthesis depending on the number of mutations introduced. cDNA were sequenced and transferred to the pET9a expression vector (Novagene) in frame with a C-terminal 6×His-tag, joined to the C-terminus by a short glycine linker (3×Gly). N terminal methionine was added to improve bacterial expression. The plasmids were transformed (heat-shock) into E. coli BL21(DE3) (Stratagene) and seeded on LB agarose plates containing 30 pig/ml kanamycin. Single colonies were picked and overnight cultures (3 ml LB-medium) were started at 37° C., 250 rpm. The following day glycerol stocks were prepared and 10 ml TB-medium supplemented with 30 µg/ml kanamycin and anti-foam were inoculated with overnight culture and grown until OD 0.6-0.8 (37° C., 300 rpm). At this point IPTG (1 mM) was added and cultures were continued for 1 hour prior to harvest of the bacteria by centrifugation. The pellets were washed in PBS and frozen at −20° C. A freeze-thaw protocol for bacterial lysis was used (three freeze/thaw cycles in 1 ml PBS each) and the proteins were purified using Ni-NTA pre-packed spin-columns (Pierce). After purification the eluted proteins were activated with 10 mM DTI prior to buffer exchange (3 volumes PBS in MWCO 9K Millipore cfg devises). The purity and stability of each protein was evaluated using sodium dodecyl sulphate polyacrylamide gel electrophoreses (SDS-PAGE) stainless 12% Mini-PRO-TEAN® TGX™ precast gel (Biorad) SDS-PAGE.

The following table summarises the changes made for each tested polypeptide relative to mature IdeZ or IdeS/Z, not including the N terminal methionine and his tag. Thus, the sequence of each polypeptide used in the experiments described herein typically comprises the sequence of the SEQ ID NO as indicated in the table, plus an additional N terminal

| Internal reference | Modifications relative to IdeZ (SEQ ID NO: 4) (positions correspond to SEQ ID NO: 3) | SEQ ID NO |
|---|---|---|
| pCART197 | H84N, N138R, A147E, D150R, N162E, N171Y, N205K, D226N, Q251E, E255K, A312K, S349N | 6 |
| pCART198 | A93T, D95N, Q140E, R165K, D166E, A174T, D226N, L237F, N239E, N243K, N282D, E288K, H315K, K347Q | 7 |
| pCART200 | D36__I53replacedS31__V48 of SEQ 2 i.e. SFSANQEI RYSEVTPYHV replaces DYQRNATE AYAKEVPHQI | 8 |
| pCART201 | D35__T54del | 9 |
| pCART202 | R70T, Y71del, N72Q, N73G | 10 |
| pCART203 | L64__T65del, R70T, Y71del, N72Q, N73G | 11 |
| pCART204 | R70T, Y71del | 12 |
| pCART206 | L64__T65del, R70T, Y71del, N72Q, N73G, F137I | 13 |
| pCART207 | L64__T65del, R70T, Y71del, N72Q, N73G, N138R | 14 |
| pCART208 | L64__T65del, R70T, Y71del, N72Q, N73G, F137I, N138R | 15 |
| pCART210 | L64__T65del, R70T, Y71del, N72Q, N73G, H84N, N138R, N162E, N205K, D226N | 16 |
| pCART217 | D35__T54del, L64__T65del, R70T, Y71del, N72Q, N73G, N138R, D226N | 17 |
| pCART219 | L64__T65del, R70T, Y71del, N72Q, N73G, K97A, N138R, D226N | 18 |
| pCART226 | D35__T54del, L64__T65del, R70T, Y71del, N72Q, N73G, K97A, N138R, D226N | 19 |
| pCART229 | L64__T65del, R70T, Y71del, N72Q, N73G, N138R, D226N | 20 |

| Internal reference | Modifications relative to IdeS/Z (SEQ ID NO: 5) (positions correspond to SEQ ID NO: 3) | SEQ ID NO |
|---|---|---|
| pCART191 | R70T, Y71del, N72Q, N73G, D140E, G171Y, R175K, R176H, I177L, S267R | 21 |
| pCART192 | R70T, Y71del, N72Q, N73G, N138R, D140E, K147E, D150R, N162E, G171Y, R175K, R176H, I177L, E206K, Q249S, K253N, S267R, A310K, S347N | 22 |
| pCART193 | R70T, Y71del, N72Q, N73G, A93T, D95N, N99D, D140E, N141Q, K147E, N162E, G171Y, A174T, R175K, R176H, I177L, N237E, N241K, D242E, T245D, I246L, K253E, S267R, E286K, H311A, H313K, Q344N, K345Q, L346T | 23 |
| pCART194 | R70T, Y71del, N72Q, N73G, A93T, D95N, N99D, N138R, D140E, N141Q, K147E, D150R, N162E, G171Y, A174T, R175K, R176H, I177L, E206K, N237E, N241K, D242E, T245D, I246L, Q249E, S267R, N280D, E286K, A310K, H311A, H313K, Q344N, K345Q, L346T, S347N | 24 |
| pCART205 | L64__65del, R70T, Y71del, N72Q, N73G, F77I, N138R, D140E, N141Q | 25 |

As controls, versions of IdeS, IdeZ and IdeS/Z were produced using the same methodology as described above. These versions are referred to herein as pCART124, pCART144 and pCART145 respectively.

pCART124 comprises the sequence of SEQ ID NO: 2 plus an additional N terminal methionine and a his tag joined to the C terminal end by a short glycine linker.

The sequence of pCART124 is provided below:

(SEQ ID NO: 26)
MDSFSANQEIRYSEVTPYHVTSVWTKGVTPPANFTQGEDVFHAPYVANQ

GWYDITKTFNGKDDLLCGAATAGNMLHWWFDQNKDQIKRYLEEHPEKQK

INFNGEQMFDVKEAIDTKNHQLDSKLFEYFKEKAFPYLSTKHLGVFPDH

VIDMFINGYRLSLTNHGPTPVKEGSKDPRGGIFDAVFTRGDQSKLLTSR

HDFKEKNLKEISDLIKKELTEGKALGLSHTYANVRINHVINLWGADFDS

NGNLKAIYVTDSDSNASIGMKKYFVGVNSAGKVAISAKEIKEDNIGAQV

LGLFTLSTGQDSWNQTNGGGHHHHHH pCART144 comprises the sequence of SEQ ID NO: 4 plus an additional N terminal methionine and a his tag joined to the C terminal end by a short glycine linker.

The sequence of pCART144 is provided below:

(SEQ ID NO: 27)
MDDYQRNATEAYAKEVPHQITSVWTKGVIPLIPEQFRYNNEDVIHAPYL

AHQGWYDITKAFDGKDNLLCGAATAGNMLHWWFDQNKTEIEAYLSKHPE

KQKIIFNNQELFDLKAAIDTKDSQINSQLFNYFRDKAFPNLSARQLGVM

PDLVLDMFINGYYLNVFKIQSTDVNRPYQDKDKRGGIFDAVFIRGDQTT

LLTARHDLKNKGLNDISTIIKQELTEGRALALSHIYANVSISHVINLWL

GADFNAEGNLEAIYVIDSDANASIGMKKYFVGINAHGHVAISAKKIEGE

NIGAQVLGLFTLSSGKDIWQKLSGGGHHHHHH pCART145 comprises the sequence of SEQ ID NO: 5 plus an additional N terminal methionine and a his tag joined to the C terminal end by a short glycine linker.

The sequence of pCART145 is provided below:

(SEQ ID NO: 28)
MDDYQRNATEAYAKEVPHQITSVWTKGVIPLIPEQFRYNNEDVFHAPYV

ANQGWYDITKAFDGKDNLLCGAATAGNMLHWWFDQNKDQIKRYLEEHPE

KQKINFNGDNMFDVKKAIDTKNHQLDSKLFNYFKEKAFPGLSARRIGVF

PDHVIDMFINGYRLSLINHGPTPVKEGSKDPRGGIFDAVFIRGNQSKLL

TSRHDFKNKNLNDISTIIKQELTKGKALGLSHIYANVSINHVINLWGAD

FNAEGNLEAIYVIDSDSNASIGMKKYFVGVNAHGHVAISAKKIEGENIG

AQVLGLFTLSTGQDSWQKLSGGGHHHHHH

IdeS lacking tag was also independently produced to GMP standard using automated multistep chromatographic purification, for use as a further control. This polypeptide is referred to herein as BX1001865.

The cDNA sequence used to produce each of the tested polypeptides and pCART124, pCART144 and pCART145 is provided below. Each cDNA sequence includes at the 3' end a codon for the N terminal methionine (ATG) and, prior to the stop codon (TAA) at the 5' end, codons for the glycine linker and the histidine tag.

pCART124

(IdeS; SEQ ID NO: 33)

ATGGATAGTTTTTCTGCTAATCAAGAGATTAGATATTCGGAAGTAACACCTTATCACGTTACTTCCGTTTGGACC

AAAGGAGTTACTCCTCCAGCAAACTTCACTCAAGGTGAAGATGTTTTTCACGCTCCTTATGTTGCTAACCAAGGA

TGGTATGATATTACCAAAACATTCAATGGAAAAGACGATCTTCTTTGCGGGGCTGCCACAGCAGGGAATATGCTT

CACTGGTGGTTCGATCAAAACAAAGACCAAATTAAACGTTATTTGGAAGAGCATCCAGAAAAGCAAAAAATAAAC

TTCAATGGCGAACAGATGTTTGACGTAAAAGAAGCTATCGACACTAAAAACCACCAGCTAGATAGTAAATTATTT

GAATATTTTAAAGAAAAAGCTTTCCCTTATCTATCTACTAAACACCTAGGAGTTTTCCCTGATCATGTAATTGAT

ATGTTCATTAACGGCTACCGCCTTAGTCTAACTAACCACGGTCCAACGCCAGTAAAAGAAGGTAGTAAAGATCCC

CGAGGTGGTATTTTTGACGCCGTATTTACAAGAGGTGATCAAAGTAAGCTATTGACAAGTCGTCATGATTTTAAA

GAAAAAAATCTCAAAGAAATCAGTGATCTCATTAAGAAAGAGTTAACCGAAGGCAAGGCTCTAGGCCTATCACAC

ACCTACGCTAACGTACGCATCAACCATGTTATAAACCTGTGGGGAGCTGACTTTGATTCTAACGGGAACCTTAAA

GCTATTTATGTAACAGACTCTGATAGTAATGCATCTATTGGTATGAAGAAATACTTTGTTGGTGTTAATTCCGCT

GGAAAAGTAGCTATTTCTGCTAAAGAAATAAAAGAAGATAATATAGGTGCTCAAGTACTAGGGTTATTTACACTT

TCAACAGGGCAAGATAGTTGGAATCAGACCAATGGCGGTGGCCATCATCACCATCACCACTAA pCART144

(IdeZ; SEQ ID NO: 34)

ATGGACGATTACCAAAGGAATGCTACGGAAGCTTATGCCAAAGAAGTACCACATCAGATCACTTCTGTATGGACC

AAAGGTGTTACACCACTAACACCCGAGCAGTTTCGATATAATAACGAAGATGTGATCCATGCGCCATATCTTGCT

CATCAAGGCTGGTACGATATCACCAAGGCCTTCGATGGGAAGGATAATCTCTTGTGTGGCGCAGCAACGGCAGGT

AATATGCTGCATTGGTGGTTTGATCAAAATAAAACAGAGATTGAAGCCTATTTAAGTAAACACCCTGAAAAGCAA

AAAATCATTTTTAACAACCAAGAGCTATTTGATTTGAAAGCTGCTATCGATACCAAGGACAGTCAAACCAATAGT

CAGCTTTTTAATTATTTTAGAGATAAAGCCTTTCCAAATCTATCAGCACGTCAACTCGGGGTTATGCCTGATCTT

GTTCTAGATATGTTTATCAATGGTTACTACTTAAATGTGTTTAAAACACAGTCTACTGATGTCAATCGACCTTAT

CAGGACAAGGACAAACGAGGTGGTATTTTCGATGCTGTTTTCACCAGAGGAGATCAGACAACGCTCTTGACAGCT

CGTCATGATTTAAAAAATAAAGGACTAAATGACATCAGCACCATTATCAAGCAAGAACTGACTGAAGGAAGAGCC

CTTGCTTTATCACATACCTACGCCAATGTTAGCATTAGCCATGTGATTAACTTGTGGGGAGCTGATTTTAATGCT

GAAGGAAACCTTGAGGCCATCTATGTCACAGACTCAGATGCTAATGCGTCTATTGGTATGAAAAAATATTTTGTC

GGCATTAATGCTCATGGACATGTCGCCATTTCTGCCAAGAAAATAGAAGGAGAAAACATTGGCGCTCAAGTATTA

GGCTTATTTACGCTTTCCAGTGGCAAGGACATTTGGCAGAAACTGAGCGGCGGTGGCCATCATCACCATCACCAC

TAA pCART145

(IdeS/Z; SEQ ID NO: 35)

ATGGATGATTATCAGCGCAACGCGACCGAAGCGTATGCGAAAGAAGTGCCGCATCAGATTACCAGCGTGTGGACC

AAAGGCGTGACCCCGCTGACCCCGGAACAGTTTCGCTATAACAACGAAGATGTGTTTCATGCGCCGTATGTGGCG

AACCAGGGCTGGTATGATATTACCAAAGCGTTTGATGGCAAAGATAACCTGCTGTGCGGCGCGGCGACCGCGGGC

AACATGCTGCATTGGTGGTTTGATCAGAACAAAGATCAGATTAAACGCTATCTGGAAGAACATCCGGAAAAACAG

-continued

AAAATTAACTTTAACGGCGATAACATGTTTGATGTGAAAAAAGCGATTGATACCAAAAACCATCAGCTGGATAGC

AAACTGTTTAACTATTTTAAAGAAAAAGCGTTTCCGGGCCTGAGCGCGCGCCGCATTGGCGTGTTTCCGGATCAT

GTGATTGATATGTTTATTAACGGCTATCGCCTGAGCCTGACCAACCATGGCCCGACCCCGGTGAAAGAAGGCAGC

AAAGATCCGCGCGGCGGCATTTTTGATGCGGTGTTTACCCGCGGCAACCAGAGCAAACTGCTGACCAGCCGCCAT

GATTTTAAAAACAAAAACCTGAACGATATTAGCACCATTATTAAACAGGAACTGACCAAAGGCAAAGCGCTGGGC

CTGAGCCATACCTATGCGAACGTGAGCATTAACCATGTGATTAACCTGTGGGGCGCGGATTTTAACGCGGAAGGC

AACCTGGAAGCGATTTATGTGACCGATAGCGATAGCAACGCGAGCATTGGCATGAAAAAATATTTTGTGGGCGTG

AACGCGCATGGCCATGTGGCGATTAGCGCGAAAAAAATTGAAGGCGAAAACATTGGCGCGCAGGTGCTGGGCCTG

TTTACCCTGAGCACCGGCCAGGATAGCTGGCAGAAACTGAGCGGCGGTGGCCATCATCACCATCACCACTAA pCART197

(SEQ ID NO: 36)
ATGGATGATTATCAGCGCAACGCGACCGAAGCGTATGCGAAAGAAGTGCCGCATCAGATTACCAGCGTGTGGACC

AAAGGCGTGACCCCGCTGACCCCGGAACAGTTTCGCTATAACAACGAAGATGTGATTCATGCGCCGTATCTGGCG

AACCAGGGCTGGTATGATATTACCAAAGCGTTTGATGGCAAAGATAACCTGCTGTGCGGCGCGGCGACCGCGGGC

AACATGCTGCATTGGTGGTTTGATCAGAACAAAACCGAAATTGAAGCGTATCTGAGCAAACATCCGGAAAAACAG

AAAATTATTTTTCGCAACCAGGAACTGTTTGATCTGAAAGAAGCGATTCGCACCAAAGATAGCCAGACCAACAGC

CAGCTGTTTGAATATTTTCGCGATAAAGCGTTTCCGTATCTGAGCGCGCGCCAGCTGGGCGTGATGCCGGATCTG

GTGCTGGATATGTTTATTAACGGCTATTATCTGAACGTGTTTAAAACCCAGAGCACCGATGTGAAACGCCCGTAT

CAGGATAAAGATAAACGCGGCGGCATTTTTGATGCGGTGTTTACCCGCGGCAACCAGACCACCCTGCTGACCGCG

CGCCATGATCTGAAAAACAAAGGCCTGAACGATATTAGCACCATTATTAAAGAAGAACTGACCAAAGGCCGCGCG

CTGGCGCTGAGCCATACCTATGCGAACGTGAGCATTAGCCATGTGATTAACCTGTGGGGCGCGGATTTTAACGCG

GAAGGCAACCTGGAAGCGATTTATGTGACCGATAGCGATGCGAACGCGAGCATTGGCATGAAAAAATATTTTGTG

GGCATTAACAAACATGGCCATGTGGCGATTAGCGCGAAAAAAATTGAAGGCGAAAACATTGGCGCGCAGGTGCTG

GGCCTGTTTACCCTGAGCAGCGGCAAAGATATTTGGCAGAAACTGAACGGCGGTGGCCATCATCACCATCACCAC

TAA pCART198

(SEQ ID NO: 37)
ATGGATGATTATCAGCGCAACGCGACCGAAGCGTATGCGAAAGAAGTGCCGCATCAGATTACCAGCGTGTGGACC

AAAGGCGTGACCCCGCTGACCCCGGAACAGTTTCGCTATAACAACGAAGATGTGATTCATGCGCCGTATCTGGCG

CATCAGGGCTGGTATGATATTACCAAAACCTTTAACGGCAAAGATAACCTGCTGTGCGGCGCGGCGACCGCGGGC

AACATGCTGCATTGGTGGTTTGATCAGAACAAAACCGAAATTGAAGCGTATCTGAGCAAACATCCGGAAAAACAG

AAAATTATTTTTAACAACGAAGAACTGTTTGATCTGAAAGCGGCGATTGATACCAAAGATAGCCAGACCAACAGC

CAGCTGTTTAACTATTTTAAAGAAAAAGCGTTTCCGAACCTGAGCACCCGCCAGCTGGGCGTGATGCCGGATCTG

GTGCTGGATATGTTTATTAACGGCTATTATCTGAACGTGTTTAAAACCCAGAGCACCGATGTGAACCGCCCGTAT

CAGGATAAAGATAAACGCGGCGGCATTTTTGATGCGGTGTTTACCCGCGGCAACCAGACCACCCTGCTGACCGCG

CGCCATGATTTTAAAGAAAAAGGCCTGAAAGATATTAGCACCATTATTAAACAGGAACTGACCGAAGGCCGCGCG

CTGGCGCTGAGCCATACCTATGCGAACGTGAGCATTAGCCATGTGATTAACCTGTGGGGCGCGGATTTTGATGCG

GAAGGCAACCTGAAAGCGATTTATGTGACCGATAGCGATGCGAACGCGAGCATTGGCATGAAAAAATATTTTGTG

GGCATTAACGCGCATGGCAAAGTGGCGATTAGCGCGAAAAAAATTGAAGGCGAAAACATTGGCGCGCAGGTGCTG

GGCCTGTTTACCCTGAGCAGCGGCAAAGATATTTGGCAGCAGCTGAGCGGCGGTGGCCATCATCACCATCACCAC

TAA

-continued pCART200 (SEQ ID NO: 38)
ATGGATAGCTTTAGCGCGAACCAGGAAATTCGCTATAGCGAAGTGACCCCGTATCATGTGACCAGCGTGTGGACC
AAAGGCGTGACCCCGCTGACCCCGGAACAGTTTCGCTATAACAACGAAGATGTGATTCATGCGCCGTATCTGGCG
CATCAGGGCTGGTATGATATTACCAAAGCGTTTGATGGCAAAGATAACCTGCTGTGCGGCGCGGCGACCGCGGGC
AACATGCTGCATTGGTGGTTTGATCAGAACAAAACCGAAATTGAAGCGTATCTGAGCAAACATCCGGAAAAACAG
AAAATTATTTTTAACAACCAGGAACTGTTTGATCTGAAAGCGGCGATTGATACCAAAGATAGCCAGACCAACAGC
CAGCTGTTTAACTATTTTCGCGATAAAGCGTTTCCGAACCTGAGCGCGCGCCAGCTGGGCGTGATGCCGGATCTG
GTGCTGGATATGTTTATTAACGGCTATTATCTGAACGTGTTTAAAACCCAGAGCACCGATGTGAACCGCCCGTAT
CAGGATAAAGATAAACGCGGCGGCATTTTTGATGCGGTGTTTACCCGCGGCGATCAGACCACCCTGCTGACCGCG
CGCCATGATCTGAAAAACAAAGGCCTGAACGATATTAGCACCATTATTAAACAGGAACTGACCGAAGGCCGCGCG
CTGGCGCTGAGCCATACCTATGCGAACGTGAGCATTAGCCATGTGATTAACCTGTGGGGCGCGGATTTTAACGCG
GAAGGCAACCTGGAAGCGATTTATGTGACCGATAGCGATGCGAACGCGAGCATTGGCATGAAAAAATATTTTGTG
GGCATTAACGCGCATGGCCATGTGGCGATTAGCGCGAAAAAAATTGAAGGCGAAAACATTGGCGCGCAGGTGCTG
GGCCTGTTTACCCTGAGCAGCGGCAAAGATATTTGGCAGAAACTGAGCGGCGGTGGCCATCATCACCATCACCAC
TAA pCART201 (SEQ ID NO: 39)
ATGAGCGTGTGGACCAAAGGCGTGACCCCGCTGACCCCGGAACAGTTTCGCTATAACAACGAAGATGTGATTCAT
GCGCCGTATCTGGCGCATCAGGGCTGGTATGATATTACCAAAGCGTTTGATGGCAAAGATAACCTGCTGTGCGGC
GCGGCGACCGCGGGCAACATGCTGCATTGGTGGTTTGATCAGAACAAAACCGAAATTGAAGCGTATCTGAGCAAA
CATCCGGAAAAACAGAAAATTATTTTTAACAACCAGGAACTGTTTGATCTGAAAGCGGCGATTGATACCAAAGAT
AGCCAGACCAACAGCCAGCTGTTTAACTATTTTCGCGATAAAGCGTTTCCGAACCTGAGCGCGCGCCAGCTGGGC
GTGATGCCGGATCTGGTGCTGGATATGTTTATTAACGGCTATTATCTGAACGTGTTTAAAACCCAGAGCACCGAT
GTGAACCGCCCGTATCAGGATAAAGATAAACGCGGCGGCATTTTTGATGCGGTGTTTACCCGCGGCGATCAGACC
ACCCTGCTGACCGCGCGCCATGATCTGAAAAACAAAGGCCTGAACGATATTAGCACCATTATTAAACAGGAACTG
ACCGAAGGCCGCGCGCTGGCGCTGAGCCATACCTATGCGAACGTGAGCATTAGCCATGTGATTAACCTGTGGGGC
GCGGATTTTAACGCGGAAGGCAACCTGGAAGCGATTTATGTGACCGATAGCGATGCGAACGCGAGCATTGGCATG
AAAAAATATTTTGTGGGCATTAACGCGCATGGCCATGTGGCGATTAGCGCGAAAAAAATTGAAGGCGAAAACATT
GGCGCGCAGGTGCTGGGCCTGTTTACCCTGAGCAGCGGCAAAGATATTTGGCAGAAACTGAGCGGCGGTGGCCAT
CATCACCATCACCACTAA pCART202 (SEQ ID NO: 40)
ATGGACGATTACCAAAGGAATGCTACGGAAGCTTATGCCAAAGAAGTACCACATCAGATCACTTCTGTATGGACC
AAAGGTGTTACACCACTAACACCCGAGCAGTTTACTCAAGGTGAAGATGTGATCCATGCGCCATATCTTGCTCAT
CAAGGCTGGTACGATATCACCAAGGCCTTCGATGGGAAGGATAATCTCTTGTGTGGCGCAGCAACGGCAGGTAAT
ATGCTGCATTGGTGGTTTGATCAAATAAAACAGAGATTGAAGCCTATTTAAGTAAACACCCTGAAAAGCAAAA
ATCATTTTTAACAACCAAGAGCTATTTGATTTGAAAGCTGCTATCGATACCAAGGACAGTCAAACCAATAGTCAG
CTTTTTAATTATTTTAGAGATAAAGCCTTTCCAAATCTATCAGCACGTCAACTCGGGGTTATGCCTGATCTTGTT
CTAGATATGTTTATCAATGGTTACTACTTAAATGTGTTTAAAACACAGTCTACTGATGTCAATCGACCTTATCAG
GACAAGGACAAACGAGGTGGTATTTTCGATGCTGTTTTCACCAGAGGAGATCAGACAACGCTCTTGACAGCTCGT
CATGATTTAAAAAATAAAGGACTAAATGACATCAGCACCATTATCAAGCAAGAACTGACTGAAGGAAGAGCCCTT
GCTTTATCACATACCTACGCCAATGTTAGCATTAGCCATGTGATTAACTTGTGGGGAGCTGATTTTAATGCTGAA -continued GGAAACCTTGAGGCCATCTATGTCACAGACTCAGATGCTAATGCGTCTATTGGTATGAAAAAATATTTTGTCGGC
ATTAATGCTCATGGACATGTCGCCATTTCTGCCAAGAAAATAGAAGGAGAAAACATTGGCGCTCAAGTATTAGGC
TTATTTACGCTTTCCAGTGGCAAGGACATTTGGCAGAAACTGAGCGGCGGTGGCCATCATCACCATCACCACTAA pCART203

(SEQ ID NO: 41)

ATGGACGATTACCAAAGGAATGCTACGGAAGCTTATGCCAAAGAAGTACCACATCAGATCACTTCTGTATGGACC
AAAGGTGTTACACCACCCGAGCAGTTTACTCAAGGTGAAGATGTGATCCATGCGCCATATCTTGCTCATCAAGGC
TGGTACGATATCACCAAGGCCTTCGATGGGAAGGATAATCTCTTGTGTGGCGCAGCAACGGCAGGTAATATGCTG
CATTGGTGGTTTGATCAAAATAAAACAGAGATTGAAGCCTATTTAAGTAAACACCCTGAAAAGCAAAAAATCATT
TTTAACAACCAAGAGCTATTTGATTTGAAAGCTGCTATCGATACCAAGGACAGTCAAACCAATAGTCAGCTTTTT
AATTATTTTAGAGATAAAGCCTTTCCAAATCTATCAGCACGTCAACTCGGGGTTATGCCTGATCTTGTTCTAGAT
ATGTTTATCAATGGTTACTACTTAAATGTGTTTAAAACACAGTCTACTGATGTCAATCGACCTTATCAGGACAAG
GACAAACGAGGTGGTATTTTCGATGCTGTTTTCACCAGAGGAGATCAGACAACGCTCTTGACAGCTCGTCATGAT
TTAAAAAATAAAGGACTAAATGACATCAGCACCATTATCAAGCAAGAACTGACTGAAGGAAGAGCCCTTGCTTTA
TCACATACCTACGCCAATGTTAGCATTAGCCATGTGATTAACTTGTGGGAGCTGATTTTAATGCTGAAGGAAAC
CTTGAGGCCATCTATGTCACAGACTCAGATGCTAATGCGTCTATTGGTATGAAAAAATATTTTGTCGGCATTAAT
GCTCATGGACATGTCGCCATTTCTGCCAAGAAAATAGAAGGAGAAAACATTGGCGCTCAAGTATTAGGCTTATTT
ACGCTTTCCAGTGGCAAGGACATTTGGCAGAAACTGAGCGGCGGTGGCCATCATCACCATCACCACTAA pCART204

(SEQ ID NO: 42)

ATGGACGATTACCAAAGGAATGCTACGGAAGCTTATGCCAAAGAAGTACCACATCAGATCACTTCTGTATGGACC
AAAGGTGTTACACCACCCGAGCAGTTTCGATATAATAACGAAGATGTGATCCATGCGCCATATCTTGCTCATCAA
GGCTGGTACGATATCACCAAGGCCTTCGATGGGAAGGATAATCTCTTGTGTGGCGCAGCAACGGCAGGTAATATG
CTGCATTGGTGGTTTGATCAAAATAAAACAGAGATTGAAGCCTATTTAAGTAAACACCCTGAAAAGCAAAAAATC
ATTTTTAACAACCAAGAGCTATTTGATTTGAAAGCTGCTATCGATACCAAGGACAGTCAAACCAATAGTCAGCTT
TTTAATTATTTTAGAGATAAAGCCTTTCCAAATCTATCAGCACGTCAACTCGGGGTTATGCCTGATCTTGTTCTA
GATATGTTTATCAATGGTTACTACTTAAATGTGTTTAAAACACAGTCTACTGATGTCAATCGACCTTATCAGGAC
AAGGACAAACGAGGTGGTATTTTCGATGCTGTTTTCACCAGAGGAGATCAGACAACGCTCTTGACAGCTCGTCAT
GATTTAAAAAATAAAGGACTAAATGACATCAGCACCATTATCAAGCAAGAACTGACTGAAGGAAGAGCCCTTGCT
TTATCACATACCTACGCCAATGTTAGCATTAGCCATGTGATTAACTTGTGGGAGCTGATTTTAATGCTGAAGGA
AACCTTGAGGCCATCTATGTCACAGACTCAGATGCTAATGCGTCTATTGGTATGAAAAAATATTTTGTCGGCATT
AATGCTCATGGACATGTCGCCATTTCTGCCAAGAAAATAGAAGGAGAAAACATTGGCGCTCAAGTATTAGGCTTA
TTTACGCTTTCCAGTGGCAAGGACATTTGGCAGAAACTGAGCGGCGGTGGCCATCATCACCATCACCACTAA pCART206

(SEQ ID NO: 43)

ATGGACGATTACCAAAGGAATGCTACGGAAGCTTATGCCAAAGAAGTACCACATCAGATCACTTCTGTATGGACC
AAAGGTGTTACACCACCCGAGCAGTTTACTCAAGGTGAAGATGTGATCCATGCGCCATATCTTGCTCATCAAGGC
TGGTACGATATCACCAAGGCCTTCGATGGGAAGGATAATCTCTTGTGTGGCGCAGCAACGGCAGGTAATATGCTG
CATTGGTGGTTTGATCAAAATAAAACAGAGATTGAAGCCTATTTAAGTAAACACCCTGAAAAGCAAAAAATCATT
ATTAACAACCAAGAGCTATTTGATTTGAAAGCTGCTATCGATACCAAGGACAGTCAAACCAATAGTCAGCTTTTT
AATTATTTTAGAGATAAAGCCTTTCCAAATCTATCAGCACGTCAACTCGGGGTTATGCCTGATCTTGTTCTAGAT
ATGTTTATCAATGGTTACTACTTAAATGTGTTTAAAACACAGTCTACTGATGTCAATCGACCTTATCAGGACAAG
GACAAACGAGGTGGTATTTTCGATGCTGTTTTCACCAGAGGAGATCAGACAACGCTCTTGACAGCTCGTCATGAT
TTAAAAAATAAAGGACTAAATGACATCAGCACCATTATCAAGCAAGAACTGACTGAAGGAAGAGCCCTTGCTTTA

-continued

TCACATACCTACGCCAATGTTAGCATTAGCCATGTGATTAACTTGTGGGAGCTGATTTTAATGCTGAAGGAAAC

CTTGAGGCCATCTATGTCACAGACTCAGATGCTAATGCGTCTATTGGTATGAAAAAATATTTTGTCGGCATTAAT

GCTCATGGACATGTCGCCATTTCTGCCAAGAAAATAGAAGGAGAAAACATTGGCGCTCAAGTATTAGGCTTATTT

ACGCTTTCCAGTGGCAAGGACATTTGGCAGAAACTGAGCGGCGGTGGCCATCATCACCATCACCACTAA pCART207

(SEQ ID NO: 44)
ATGGACGATTACCAAAGGAATGCTACGGAAGCTTATGCCAAAGAAGTACCACATCAGATCACTTCTGTATGGACC

AAAGGTGTTACACCACCCGAGCAGTTTACTCAAGGTGAAGATGTGATCCATGCGCCATATCTTGCTCATCAAGGC

TGGTACGATATCACCAAGGCCTTCGATGGGAAGGATAATCTCTTGTGTGGCGCAGCAACGGCAGGTAATATGCTG

CATTGGTGGTTTGATCAAAATAAAACAGAGATTGAAGCCTATTTAAGTAAACACCCTGAAAAGCAAAAATCATT

TTTCGTAACCAAGAGCTATTTGATTTGAAAGCTGCTATCGATACCAAGGACAGTCAAACCAATAGTCAGCTTTTT

AATTATTTTAGAGATAAAGCCTTTCCAAATCTATCAGCACGTCAACTCGGGGTTATGCCTGATCTTGTTCTAGAT

ATGTTTATCAATGGTTACTACTTAAATGTGTTTAAAACACAGTCTACTGATGTCAATCGACCTTATCAGGACAAG

GACAAACGAGGTGGTATTTTCGATGCTGTTTTCACCAGAGGAGATCAGACAACGCTCTTGACAGCTCGTCATGAT

TTAAAAAATAAAGGACTAAATGACATCAGCACCATTATCAAGCAAGAACTGACTGAAGGAAGAGCCCTTGCTTTA

TCACATACCTACGCCAATGTTAGCATTAGCCATGTGATTAACTTGTGGGAGCTGATTTTAATGCTGAAGGAAAC

CTTGAGGCCATCTATGTCACAGACTCAGATGCTAATGCGTCTATTGGTATGAAAAAATATTTTGTCGGCATTAAT

GCTCATGGACATGTCGCCATTTCTGCCAAGAAAATAGAAGGAGAAAACATTGGCGCTCAAGTATTAGGCTTATTT

ACGCTTTCCAGTGGCAAGGACATTTGGCAGAAACTGAGCGGCGGTGGCCATCATCACCATCACCACTAA pCART208

(SEQ ID NO: 45)
ATGGACGATTACCAAAGGAATGCTACGGAAGCTTATGCCAAAGAAGTACCACATCAGATCACTTCTGTATGGACC

AAAGGTGTTACACCACCCGAGCAGTTTACTCAAGGTGAAGATGTGATCCATGCGCCATATCTTGCTCATCAAGGC

TGGTACGATATCACCAAGGCCTTCGATGGGAAGGATAATCTCTTGTGTGGCGCAGCAACGGCAGGTAATATGCTG

CATTGGTGGTTTGATCAAAATAAAACAGAGATTGAAGCCTATTTAAGTAAACACCCTGAAAAGCAAAAATCATT

ATTCGTAACCAAGAGCTATTTGATTTGAAAGCTGCTATCGATACCAAGGACAGTCAAACCAATAGTCAGCTTTTT

AATTATTTTAGAGATAAAGCCTTTCCAAATCTATCAGCACGTCAACTCGGGGTTATGCCTGATCTTGTTCTAGAT

ATGTTTATCAATGGTTACTACTTAAATGTGTTTAAAACACAGTCTACTGATGTCAATCGACCTTATCAGGACAAG

GACAAACGAGGTGGTATTTTCGATGCTGTTTTCACCAGAGGAGATCAGACAACGCTCTTGACAGCTCGTCATGAT

TTAAAAAATAAAGGACTAAATGACATCAGCACCATTATCAAGCAAGAACTGACTGAAGGAAGAGCCCTTGCTTTA

TCACATACCTACGCCAATGTTAGCATTAGCCATGTGATTAACTTGTGGGAGCTGATTTTAATGCTGAAGGAAAC

CTTGAGGCCATCTATGTCACAGACTCAGATGCTAATGCGTCTATTGGTATGAAAAAATATTTTGTCGGCATTAAT

GCTCATGGACATGTCGCCATTTCTGCCAAGAAAATAGAAGGAGAAAACATTGGCGCTCAAGTATTAGGCTTATTT

ACGCTTTCCAGTGGCAAGGACATTTGGCAGAAACTGAGCGGCGGTGGCCATCATCACCATCACCACTAA pCART210

(SEQ ID NO: 46)
ATGGATGATTATCAGCGCAACGCGACCGAAGCGTATGCGAAAGAAGTGCCGCATCAGATTACCAGCGTGTGGACC

AAAGGCGTGACCCCGCCGGAACAGTTTACTCAAGGTGAAGATGTGATTCATGCGCCGTATCTGGCGAACCAGGGC

TGGTATGATATTACCAAAGCGTTTGATGGCAAAGATAACCTGCTGTGCGGCGCGGCGACCGCGGGCAACATGCTG

CATTGGTGGTTTGATCAGAACAAAACCGAAATTGAAGCGTATCTGAGCAAACATCCGGAAAAACAGAAATTATT

TTTCGCAACCAGGAACTGTTTGATCTGAAAGAAGCGATTCGCACCAAAGATAGCCAGACCAACAGCCAGCTGTTT

GAATATTTTCGCGATAAAGCGTTTCCGTATCTGAGCGCGCGCCAGCTGGGCGTGATGCCGGATCTGGTGCTGGAT

ATGTTTATTAACGGCTATTATCTGAACGTGTTTAAAACCCAGAGCACCGATGTGAAACGCCCGTATCAGGATAAA

```
                                        -continued
GATAAACGCGGCGGCATTTTTGATGCGGTGTTTACCCGCGGCAACCAGACCACCCTGCTGACCGCGCGCCATGAT

CTGAAAACAAAGGCCTGAACGATATTAGCACCATTATTAAAGAAGAACTGACCAAAGGCCGCGCGCTGGCGCTG

AGCCATACCTATGCGAACGTGAGCATTAGCCATGTGATTAACCTGTGGGGCGCGGATTTTAACGCGGAAGGCAAC

CTGGAAGCGATTTATGTGACCGATAGCGATGCGAACGCGAGCATTGGCATGAAAAAATATTTTGTGGGCATTAAC

AAACATGGCCATGTGGCGATTAGCGCGAAAAAAATTGAAGGCGAAAACATTGGCGCGCAGGTGCTGGGCCTGTTT

ACCCTGAGCAGCGGCAAAGATATTTGGCAGAAACTGAACGGCGGTGGCCATCATCACCATCACCACTAA
``` pCART217
                                                                                (SEQ ID NO: 47)
```
ATGTCTGTATGGACCAAAGGTGTTACACCACCCGAGCAGTTTACTCAAGGTGAAGATGTGATCCATGCGCCATAT

CTTGCTCATCAAGGCTGGTACGATATCACCAAGGCCTTCGATGGGAAGGATAATCTCTTGTGTGGCGCAGCAACG

GCAGGTAATATGCTGCATTGGTGGTTTGATCAAAATAAAACAGAGATTGAAGCCTATTTAAGTAAACACCCTGAA

AAGCAAAAAATCATTTTTCGTAACCAAGAGCTATTTGATTTGAAAGCTGCTATCGATACCAAGGACAGTCAAACC

AATAGTCAGCTTTTTAATTATTTTAGAGATAAAGCCTTTCCAAATCTATCAGCACGTCAACTCGGGGTTATGCCT

GATCTTGTTCTAGATATGTTTATCAATGGTTACTACTTAAATGTGTTTAAAACACAGTCTACTGATGTCAATCGA

CCTTATCAGGACAAGGACAAACGAGGTGGTATTTTCGATGCTGTTTTCACCAGAGGAAACCAGACAACGCTCTTG

ACAGCTCGTCATGATTTAAAAAATAAAGGACTAAATGACATCAGCACCATTATCAAGCAAGAACTGACTGAAGGA

AGAGCCCTTGCTTTATCACATACCTACGCCAATGTTAGCATTAGCCATGTGATTAACTTGTGGGAGCTGATTTT

AATGCTGAAGGAAACCTTGAGGCCATCTATGTCACAGACTCAGATGCTAATGCGTCTATTGGTATGAAAAAATAT

TTTGTCGGCATTAATGCTCATGGACATGTCGCCATTTCTGCCAAGAAAATAGAAGGAGAAAACATTGGCGCTCAA

GTATTAGGCTTATTTACGCTTTCCAGTGGCAAGGACATTTGGCAGAAACTGAGCGGCGGTGGCCATCATCACCAT

CACCACTAA
``` pCART219
                                                                                (SEQ ID NO: 48)
```
ATGGACGATTACCAAAGGAATGCTACGGAAGCTTATGCCAAAGAAGTACCACATCAGATCACTTCTGTATGGACC

AAAGGTGTTACACCACCCGAGCAGTTTACTCAAGGTGAAGATGTGATCCATGCGCCATATCTTGCTCATCAAGGC

TGGTACGATATCACCAAGGCCTTCGATGGGGCGGATAATCTCTTGTGTGGCGCAGCAACGGCAGGTAATATGCTG

CATTGGTGGTTTGATCAAAATAAAACAGAGATTGAAGCCTATTTAAGTAAACACCCTGAAAAGCAAAAAATCATT

TTTCGTAACCAAGAGCTATTTGATTTGAAAGCTGCTATCGATACCAAGGACAGTCAAACCAATAGTCAGCTTTTT

AATTATTTTAGAGATAAAGCCTTTCCAAATCTATCAGCACGTCAACTCGGGGTTATGCCTGATCTTGTTCTAGAT

ATGTTTATCAATGGTTACTACTTAAATGTGTTTAAAACACAGTCTACTGATGTCAATCGACCTTATCAGGACAAG

GACAAACGAGGTGGTATTTTCGATGCTGTTTTCACCAGAGGAAATCAGACAACGCTCTTGACAGCTCGTCATGAT

TTAAAAAATAAAGGACTAAATGACATCAGCACCATTATCAAGCAAGAACTGACTGAAGGAAGAGCCCTTGCTTTA

TCACATACCTACGCCAATGTTAGCATTAGCCATGTGATTAACTTGTGGGAGCTGATTTTAATGCTGAAGGAAAC

CTTGAGGCCATCTATGTCACAGACTCAGATGCTAATGCGTCTATTGGTATGAAAAAATATTTTGTCGGCATTAAT

GCTCATGGACATGTCGCCATTTCTGCCAAGAAAATAGAAGGAGAAAACATTGGCGCTCAAGTATTAGGCTTATTT

ACGCTTTCCAGTGGCAAGGACATTTGGCAGAAACTGAGCGGCGGTGGCCATCATCACCATCACCACTAA
``` pCART226
                                                                                (SEQ ID NO: 49)
```
ATGTCTGTATGGACCAAAGGTGTTACACCACCCGAGCAGTTTACTCAAGGTGAAGATGTGATCCATGCGCCATAT

CTTGCTCATCAAGGCTGGTACGATATCACCAAGGCCTTCGATGGGCGGATAATCTCTTGTGTGGCGCAGCAACG

GCAGGTAATATGCTGCATTGGTGGTTTGATCAAAATAAAACAGAGATTGAAGCCTATTTAAGTAAACACCCTGAA

AAGCAAAAAATCATTTTTCGTAACCAAGAGCTATTTGATTTGAAAGCTGCTATCGATACCAAGGACAGTCAAACC

AATAGTCAGCTTTTTAATTATTTTAGAGATAAAGCCTTTCCAAATCTATCAGCACGTCAACTCGGGGTTATGCCT

GATCTTGTTCTAGATATGTTTATCAATGGTTACTACTTAAATGTGTTTAAAACACAGTCTACTGATGTCAATCGA
```

-continued

CCTTATCAGGACAAGGACAAACGAGGTGGTATTTTCGATGCTGTTTTCACCAGAGGAAATCAGACAACGCTCTTG

ACAGCTCGTCATGATTTAAAAAATAAAGGACTAAATGACATCAGCACCATTATCAAGCAAGAACTGACTGAAGGA

AGAGCCCTTGCTTTATCACATACCTACGCCAATGTTAGCATTAGCCATGTGATTAACTTGTGGGGAGCTGATTTT

AATGCTGAAGGAAACCTTGAGGCCATCTATGTCACAGACTCAGATGCTAATGCGTCTATTGGTATGAAAAAATAT

TTTGTCGGCATTAATGCTCATGGACATGTCGCATTTCTGCCAAGAAAATAGAAGGAGAAAACATTGGCGCTCAA

GTATTAGGCTTATTTACGCTTTCCAGTGGCAAGGACATTTGGCAGAAACTGAGCGGCGGTGGCCATCATCACCAT

CACCACTAA pCART229

(SEQ ID NO: 50)
ATGGACGATTACCAAAGGAATGCTACGGAAGCTTATGCCAAAGAAGTACCACATCAGATCACTTCTGTATGGACC

AAAGGTGTTACACCACCCGAGCAGTTTACTCAAGGTGAAGATGTGATCCATGCGCCATATCTTGCTCATCAAGGC

TGGTACGATATCACCAAGGCCTTCGATGGGAAGGATAATCTCTTGTGTGGCGCAGCAACGGCAGGTAATATGCTG

CATTGGTGGTTTGATCAAAATAAAACAGAGATTGAAGCCTATTTAAGTAAACACCCTGAAAAGCAAAAAATCATT

TTTCGTAACCAAGAGCTATTTGATTTGAAAGCTGCTATCGATACCAAGGACAGTCAAACCAATAGTCAGCTTTTT

AATTATTTTAGAGATAAAGCCTTTCCAAATCTATCAGCACGTCAACTCGGGGTTATGCCTGATCTTGTTCTAGAT

ATGTTTATCAATGGTTACTACTTAAATGTGTTTAAAACACAGTCTACTGATGTCAATCGACCTTATCAGGACAAG

GACAAACGAGGTGGTATTTTCGATGCTGTTTTCACCAGAGGAAACCAGACAACGCTCTTGACAGCTCGTCATGAT

TTAAAAAATAAAGGACTAAATGACATCAGCACCATTATCAAGCAAGAACTGACTGAAGGAAGAGCCCTTGCTTTA

TCACATACCTACGCCAATGTTAGCATTAGCCATGTGATTAACTTGTGGGGAGCTGATTTTAATGCTGAAGGAAAC

CTTGAGGCCATCTATGTCACAGACTCAGATGCTAATGCGTCTATTGGTATGAAAAAATATTTTGTCGGCATTAAT

GCTCATGGACATGTCGCCATTTCTGCCAAGAAAATAGAAGGAGAAAACATTGGCGCTCAAGTATTAGGCTTATTT

ACGCTTTCCAGTGGCAAGGACATTTGGCAGAAACTGAGCGGCGGTGGCCATCATCACCATCACCACTAA pCART191

(SEQ ID NO: 51)
ATGGATGATTATCAGCGCAACGCGACCGAAGCGTATGCGAAAGAAGTGCCGCATCAGATTACCAGCGTGTGGACC

AAAGGCGTGACCCCGCTGACCCCGGAACAGTTTACCCAGGGCGAAGATGTGTTTCATGCGCCGTATGTGGCGAAC

CAGGGCTGGTATGATATTACCAAAGCGTTTGATGGCAAAGATAACCTGCTGTGCGGCGCGGCGACCGCGGGCAAC

ATGCTGCATTGGTGGTTTGATCAGAACAAAGATCAGATTAAACGCTATCTGGAAGAACATCCGGAAAAACAGAAA

ATTAACTTTAACGGCGAAAACATGTTTGATGTGAAAAAAGCGATTGATACCAAAAACCATCAGCTGGATAGCAAA

CTGTTTAACTATTTTAAAGAAAAAGCGTTTCCGTATCTGAGCGCGAAACATCTGGGCGTGTTTCCGGATCATGTG

ATTGATATGTTTATTAACGGCTATCGCCTGAGCCTGACCAACCATGGCCCGACCCCGGTGAAAGAAGGCAGCAAA

GATCCGCGCGGCGGCATTTTTGATGCGGTGTTTACCCGCGGCAACCAGAGCAAACTGCTGACCAGCCGCCATGAT

TTTAAAAACAAAAACCTGAACGATATTAGCACCATTATTAAACAGGAACTGACCAAAGGCAAAGCGCTGGGCCTG

AGCCATACCTATGCGAACGTGCGCATTAACCATGTGATTAACCTGTGGGGCGCGGATTTTAACGCGGAAGGCAAC

CTGGAAGCGATTTATGTGACCGATAGCGATAGCAACGCGAGCATTGGCATGAAAAAATATTTTGTGGGCGTGAAC

GCGCATGGCCATGTGGCGATTAGCGCGAAAAAAATTGAAGGCGAAAACATTGGCGCGCAGGTGCTGGGCCTGTTT

ACCCTGAGCACCGGCCAGGATAGCTGGCAGAAACTGAGCGGCGGTGGCCATCATCACCATCACCACTAA pCART192

(SEQ ID NO: 52)
ATGGATGATTATCAGCGCAACGCGACCGAAGCGTATGCGAAAGAAGTGCCGCATCAGATTACCAGCGTGTGGACC

AAAGGCGTGACCCCGCTGACCCCGGAACAGTTTACCCAGGGCGAAGATGTGTTTCATGCGCCGTATGTGGCGAAC

CAGGGCTGGTATGATATTACCAAAGCGTTTGATGGCAAAGATAACCTGCTGTGCGGCGCGGCGACCGCGGGCAAC

ATGCTGCATTGGTGGTTTGATCAGAACAAAGATCAGATTAAACGCTATCTGGAAGAACATCCGGAAAAACAGAAA

-continued

```
ATTAACTTTCGCGGCGAAAACATGTTTGATGTGAAAGAAGCGATTCGCACCAAAAACCATCAGCTGGATAGCAAA

CTGTTTGAATATTTTAAAGAAAAAGCGTTTCCGTATCTGAGCGCGAAACATCTGGGCGTGTTTCCGGATCATGTG

ATTGATATGTTTATTAACGGCTATCGCCTGAGCCTGACCAACCATGGCCCGACCCCGGTGAAAAAAGGCAGCAAA

GATCCGCGCGGCGGCATTTTTGATGCGGTGTTTACCCGCGGCAACCAGAGCAAACTGCTGACCAGCCGCCATGAT

TTTAAAAACAAAAACCTGAACGATATTAGCACCATTATTAAAAGCGAACTGACCAACGGCAAAGCGCTGGGCCTG

AGCCATACCTATGCGAACGTGCGCATTAACCATGTGATTAACCTGTGGGCGCGGATTTTAACGCGGAAGGCAAC

CTGGAAGCGATTTATGTGACCGATAGCGATAGCAACGCGAGCATTGGCATGAAAAAATATTTTGTGGGCGTGAAC

AAACATGGCCATGTGGCGATTAGCGCGAAAAAAATTGAAGGCGAAAACATTGGCGCGCAGGTGCTGGGCCTGTTT

ACCCTGAGCACCGGCCAGGATAGCTGGCAGAAACTGAACGGCGGTGGCCATCATCACCATCACCACTAA
``` pCART193 (SEQ ID NO: 53)

```
ATGGATGATTATCAGCGCAACGCGACCGAAGCGTATGCGAAAGAAGTGCCGCATCAGATTACCAGCGTGTGGACC

AAAGGCGTGACCCCGCTGACCCCGGAACAGTTTACCCAGGGCGAAGATGTGTTTCATGCGCCGTATGTGGCGAAC

CAGGGCTGGTATGATATTACCAAAACCTTTAACGGCAAAGATGATCTGCTGTGCGGCGCGGCGACCGCGGGCAAC

ATGCTGCATTGGTGGTTTGATCAGAACAAAGATCAGATTAAACGCTATCTGGAAGAACATCCGGAAAAACAGAAA

ATTAACTTTAACGGCGAACAGATGTTTGATGTGAAAGAAGCGATTGATACCAAAAACCATCAGCTGGATAGCAAA

CTGTTTGAATATTTTAAAGAAAAAGCGTTTCCGTATCTGAGCACCAAACATCTGGGCGTGTTTCCGGATCATGTG

ATTGATATGTTTATTAACGGCTATCGCCTGAGCCTGACCAACCATGGCCCGACCCCGGTGAAAGAAGGCAGCAAA

GATCCGCGCGGCGGCATTTTTGATGCGGTGTTTACCCGCGGCAACCAGAGCAAACTGCTGACCAGCCGCCATGAT

TTTAAAGAAAAAAACCTGAAAGAAATTAGCGATCTGATTAAACAGGAACTGACCGAAGGCAAAGCGCTGGGCCTG

AGCCATACCTATGCGAACGTGCGCATTAACCATGTGATTAACCTGTGGGCGCGGATTTTGATGCGGAAGGCAAC

CTGAAAGCGATTTATGTGACCGATAGCGATAGCAACGCGAGCATTGGCATGAAAAAATATTTTGTGGGCGTGAAC

GCGGCGGGCAAAGTGGCGATTAGCGCGAAAAAAATTGAAGGCGAAAACATTGGCGCGCAGGTGCTGGGCCTGTTT

ACCCTGAGCACCGGCCAGGATAGCTGGAACCAGACCAGCGGCGGTGGCCATCATCACCATCACCACTAA
``` pCART194 (SEQ ID NO: 54)

```
ATGGATGATTATCAGCGCAACGCGACCGAAGCGTATGCGAAAGAAGTGCCGCATCAGATTACCAGCGTGTGGACC

AAAGGCGTGACCCCGCTGACCCCGGAACAGTTTACCCAGGGCGAAGATGTGTTTCATGCGCCGTATGTGGCGAAC

CAGGGCTGGTATGATATTACCAAAACCTTTAACGGCAAAGATGATCTGCTGTGCGGCGCGGCGACCGCGGGCAAC

ATGCTGCATTGGTGGTTTGATCAGAACAAAGATCAGATTAAACGCTATCTGGAAGAACATCCGGAAAAACAGAAA

ATAACTTTCGCGGCGAACAGATGTTTGATGTGAAAGAAGCGATTCGCACCAAAAACCATCAGCTGGATAGCAAA

CTGTTTGAATATTTTAAAGAAAAAGCGTTTCCGTATCTGAGCACCAAACATCTGGGCGTGTTTCCGGATCATGTG

ATTGATATGTTTATTAACGGCTATCGCCTGAGCCTGACCAACCATGGCCCGACCCCGGTGAAAAAAGGCAGCAAA

GATCCGCGCGGCGGCATTTTTGATGCGGTGTTTACCCGCGGCAACCAGAGCAAACTGCTGACCAGCCGCCATGAT

TTTAAAGAAAAAAACCTGAAAGAAATTAGCGATCTGATTAAAGAAGAACTGACCAAAGGCAAAGCGCTGGGCCTG

AGCCATACCTATGCGAACGTGCGCATTAACCATGTGATTAACCTGTGGGCGCGGATTTTGATGCGGAAGGCAAC

CTGAAAGCGATTTATGTGACCGATAGCGATAGCAACGCGAGCATTGGCATGAAAAAATATTTTGTGGGCGTGAAC

AAAGCGGGCAAAGTGGCGATTAGCGCGAAAAAAATTGAAGGCGAAAACATTGGCGCGCAGGTGCTGGGCCTGTTT

ACCCTGAGCACCGGCCAGGATAGCTGGAACCAGACCAACGGCGGTGGCCATCATCACCATCACCACTAA
``` pCART205 (SEQ ID NO: 55)

```
ATGGATGATTATCAGCGCAACGCGACCGAAGCGTATGCGAAAGAAGTGCCGCATCAGATTACCAGCGTGTGGACC

AAAGGCGTGACCCCGCCGGAACAGTTTACTCAAGGTGAAGATGTGATTCATGCGCCGTATGTGGCGAACCAGGGC

TGGTATGATATTACCAAAGCGTTTGATGGCAAAGATAACCTGCTGTGCGGCGCGGCGACCGCGGGCAACATGCTG
```

-continued

```
CATTGGTGGTTTGATCAGAACAAAGATCAGATTAAACGCTATCTGGAAGAACATCCGGAAAAACAGAAAATTAAC

TTTCGCGGCGAACAGATGTTTGATGTGAAAAAAGCGATTGATACCAAAAACCATCAGCTGGATAGCAAACTGTTT

AACTATTTTAAAGAAAAAGCGTTTCCGGGCCTGAGCGCGCGCCGCATTGGCGTGTTTCCGGATCATGTGATTGAT

ATGTTTATTAACGGCTATCGCCTGAGCCTGACCAACCATGGCCCGACCCCGGTGAAAGAAGGCAGCAAAGATCCG

CGCGGCGGCATTTTTGATGCGGTGTTTACCCGCGGCAACCAGAGCAAACTGCTGACCAGCCGCCATGATTTTAAA

AACAAAAACCTGAACGATATTAGCACCATTATTAAACAGGAACTGACCAAAGGCAAAGCGCTGGGCCTGAGCCAT

ACCTATGCGAACGTGAGCATTAACCATGTGATTAACCTGTGGGGCGCGGATTTTAACGCGGAAGGCAACCTGGAA

GCGATTTATGTGACCGATAGCGATAGCAACGCGAGCATTGGCATGAAAAAATATTTTGTGGGCGTGAACGCGCAT

GGCCATGTGGCGATTAGCGCGAAAAAAATTGAAGGCGAAAACATTGGCGCGCAGGTGCTGGGCCTGTTTACCCTG

AGCACCGGCCAGGATAGCTGGCAGAAACTGAGCGGCGGTGGCCATCATCACCATCACCACTAA
```

Example 2—Assessment of Potency (IgG Cleavage Efficacy)

ELISA

Enzymatic activity was measured using an ELISA-based potency assay. The principle of the ELISA was to coat wells of a multi titre plate with an antibody target (BSA), then incubate different concentrations of IgG cysteine protease polypeptide (test or control) with anti-BSA antibody in the wells, before detecting the quantity of anti-BSA antibody bound to the wells using a detector antibody. The higher the concentration of a given IgG cysteine protease polypeptide in a well, the less intact anti-BSA polypeptide will be bound to the well, giving a lower signal. Similarly, a more potent IgG cysteine protease polypeptide will give a lower signal than a less potent IgG cysteine protease polypeptide when present at the same concentration.

The reference IdeS BX1001865 was prepared as a titration series in 1:2 dilution steps from 320 nM down to 0.16 nM to allow plotting of a standard calibration curve for the assay. The results achieved in the assay for multiple known concentrations of each tested polypeptide were compared against the linear section of the calibration curve to determine the concentration of reference IdeS which achieved the same potency. Dividing the known concentration of each polypeptide by the determined equivalent concentration of reference IdeS from the curve, a score is produced which is the fold change in potency relative to reference IdeS BX1001865. For example, if 5 nM test polypeptide achieves a result equivalent to 10 nM reference IdeS on the calibration curve, the test polypeptide has a potency 2 fold greater than reference IdeS BX1001865. A mean score for fold change in potency relative to reference IdeS BX1001865 was calculated from all of the scores achieved at the different concentrations for each tested polypeptide, provided that they fell within the linear section of the calibration curve. This mean score was then compared to the mean score achieved for pCART124 reference IdeS, which was included on each plate to enable comparison between plates. The mean score for pCART124 is divided by the mean score for the test polypeptide to produce a "pCART124 ratio", which is effectively the fold change in potency relative to IdeS for each polypeptide. This pCART124 ratio could then be visualised on a bar diagram.

Briefing summarising the laboratory protocol: Wells of multi-titre plates were coated overnight with BSA (10 µg/ml), then washed with PBS-T and blocked for 1 hour with 2% fish skin gelatine in PBS. IdeS BX1001865 polypeptide was prepared as a titration series in 1:2 dilution steps in PBS with 0.1% gelatine from 320 nM down to 0.16 nM. The test polypeptides and the pCART124 control were then prepared at each of 15, 7.5, 3.75, and 1.9 nM in PBS with 0.1% gelatine. A 50 µl sample of polypeptide was added to each well with 50 µl of rabbit anti-BSA (ACRIS, #R1048P, 10 nM) as substrate. The plates were incubated at room temperature for 1 hour and then washed with PBS-T. Biotinylated goat anti-rabbit Fc-specific antibody (30 000× diluted) was added as a detector antibody and incubated for 30 min. The plate was washed and 40 000× diluted SA-Horseradish Peroxidase (HRP; Pierce) was added and incubated for 30 min. The plates were washed and developed using TMB One Component as a chromogenic substrate for HRP for 7 min, stopped with 0.5 M $H_2SO_4$. Absorbance (OD) was measured at $\lambda$=450 nm. Mean scores for fold change in potency relative to BX1001865 were determined for each test polypeptide and for pCART124. The "pCART124 ratio" for each test polypeptide was then calculated as set out above.

The "pCART124 ratio" results for pCART191, 192, 193, 194, 197, 198, 200 and 201 are shown in FIG. 1, alongside the result for pCART124. All of the exemplary polypeptides of the invention shown here achieve at least equivalent potency relative to the IdeS control (pCART124). pCART194, 197, 200 and 201 all achieve much higher potency, even as high as 8.0 fold improvement over control for pCART197 and pCART201.

Interestingly pCART200 and 201 both involve modifications to the N terminal end. Also, pCART194 and 197 each have the N138R/K modification. A change to a positive amino acid at the position corresponding to position 139 of SEQ ID NO: 3 is expected to produce similar results to the N138R/K substitution. Positions 138 and 139 are situated in the loop of a beta hairpin structure spanning positions 134 to 144 of SEQ ID NO: 3. Based on the results obtained herein, changes to positive amino acids in either or both of positions 138 and 139 are expected to increase IgG cysteine protease activity.

Figure 2:
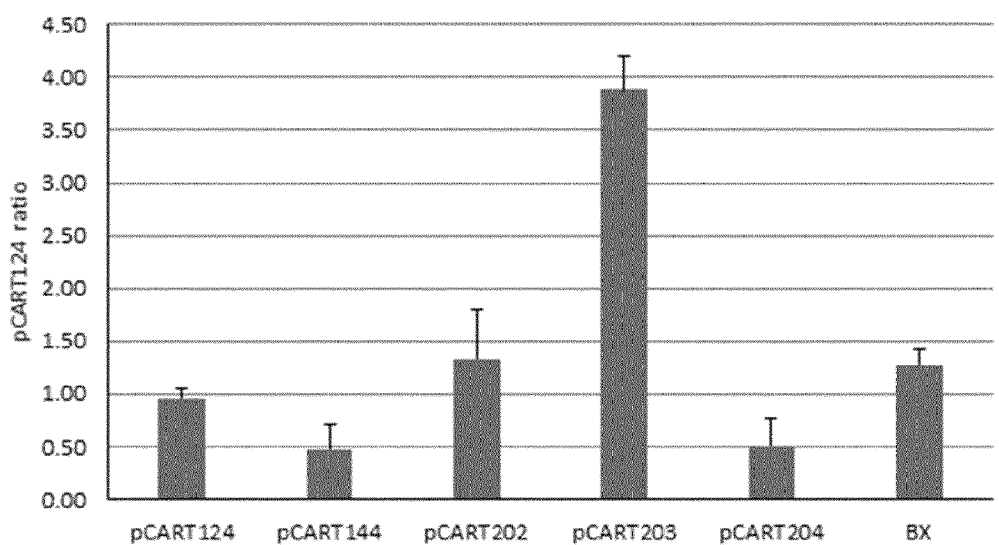

The results for pCART202, 203 and 204 are shown in FIG. 2. pCART203 in particular is around 3.5 fold more potent than IdeS. pCART202 is between 1 and 1.5 fold more potent than IdeS. pCART204 is of comparable potency to pCART144.

Visualisation of IgG Cleavage Patterns

The efficacy of the different pCART polypeptides was further evaluated by visualising on SDS-PAGE the cleavage products produced by a titration series of each polypeptide in different substrates. To test efficacy in pure IgG substrate, adalimumab (Humira) was used for IgG1 and denosumab (XGEVA) for IgG2. To test efficacy in a more complex physiological environment, some of the polypeptides were also titrated in in IVIg (Octagam). This allows the evaluation of the impact of neutralizing anti-IdeS antibodies on polypeptide activity. Cleavage patterns for each polypeptide are compared with the cleavage patterns of IdeS (BX1001865 and pCART124) in the same substrate. The protocol was follows:

For the pure IgG tests, each test polypeptide or control was diluted in a 1:3 steps titration series from 6.7 µg/ml down to 0.04 ng/ml in PBS with 0.05% BSA as supporting protein. 25 µl of each concentration was transferred to multi titre plates and the cleavage reaction was starting by adding 25 µl of either Humira or XGEVA (2 mg/ml). Thus each starting concentration of polypeptide is diluted 1:2 in the well, giving a titration series of 3.3 µg/ml down to 0.02 ng/ml.

For the IVIg tests, each test polypeptide or control was diluted in a 1:2 steps titration series from 30 µg/ml down to 0.015 ng/ml in PBS with 0.05% BSA as supporting protein. 25 µl of each concentration was transferred to multi titre plates and the cleavage reaction was starting by adding 25 µl of 10 mg/ml IVIg. Thus each starting concentration of polypeptide is diluted 1:2 in the well, giving a titration series of 15 µg/ml down to 0.0075 ng/ml.

The plates were incubated in 37° C. for 1.5 hours. The samples were mixed 1:4 in 2×SDS loading buffer and heated at 92° C. for 5 min. 10 µl were loaded on a polyacrylamide gel (15-well 4-20% Mini-PROTEAN® TGX™ precast gel (Biorad) which was read according to standard protocols.

Figure 3:
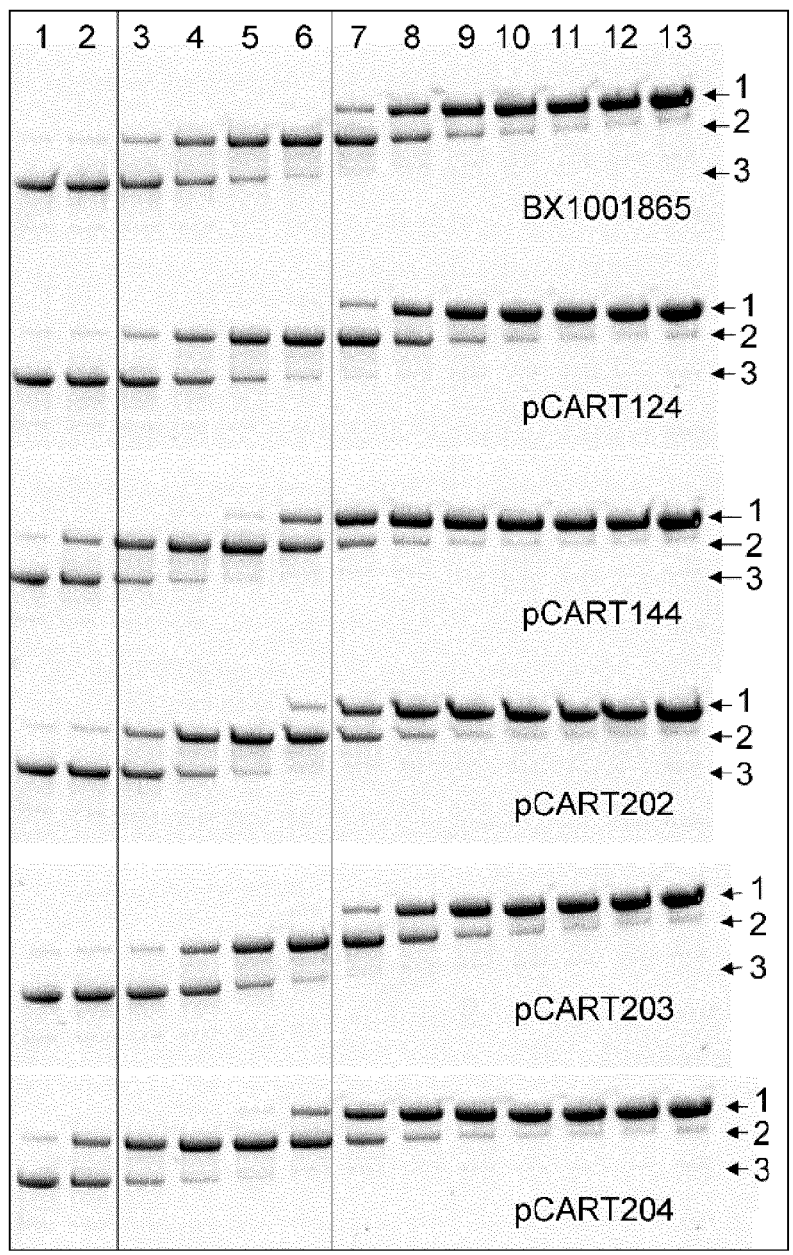
FIG. 3 shows the results of a representative SDS-PAGE gel used to visualize the cleavage products produced by incubation of IgG1 with polypeptides of the invention or controls.

FIG. 3 shows the cleavage patterns produced with IgG1 substrate for pCART202, 203 and 204 as compared to both IdeS controls (pCART124 and BX1001865) and IdeZ (pCART144). Enzyme concentrations go from 3.33 µg/ml (lane 1) down to 0.02 ng/ml (lane 12) in a 1:3 step dilution series. Intact adalimumab (without enzyme) is shown in lane 13. The arrows on the right indicate the different cleavage products from IgG. Arrow 1: Intact IgG; arrow 2: scIgG (single cleaved IgG—results from cleavage of first IgG heavy chain); arrow 3: F(ab')2 fragment (results from cleavage of second IgG heavy chain). Vertical lines were added to facilitate the comparison at the $1^{st}$ IgG heavy chain cleavage, where Intact IgG becomes scIgG (between lane 6 and 7) and at the $2^{nd}$ IgG heavy chain cleavage, where scIgG becomes $F(ab')_2$ fragment (between lane 2 and 3).

The enzyme IdeZ (pCART144) has lower cleavage efficacy of both the 1st and 2nd IgG heavy chain. IdeS (BX1001865 and pCART124) is about 3 fold more effective (i.e. one titration step) than pCART144 in cleavage of both heavy chains. Cleavage at 1.5 ng/ml (lane 8) for IdeS (BX1001865 and pCART124) equals the pCART144 (IdeZ) cleavage at 4.6 ng/ml (lane 7). BX1001865 and pCART124 show intense scIGg bands (arrow 2) at 4.6 ng/ml (lane 7) whereas pCART144 has only a weak scIgG band (arrow 2) at this concentration (lane 7).

Importantly, both pCART202 and pCART203 show increased potency in cleavage of IgG (lane 7 and lane 3) compared to IdeZ (pCART144), resulting in more intense scIgG bands (arrow 2) and more intense F(ab')2 bands (arrow 3). No increased efficacy is seen for the enzyme pCART204. The efficacy of pCART202 in cleaving the 2nd heavy chain is shown to be about the same as for IdeS (BX1001865 and pCART124) (compare lane 3). pCART202 is less effective than IdeS, but more effective than pCART144 for the 1st IgG heavy chain cleavage (compare lane 7). Enzyme pCART203 possess an even higher efficacy than IdeS in cleavage of primarily the 2nd heavy chain, resulting in a more intense F(ab')2 band (arrow 3) and a weaker scIgG band (arrow 2) compared with BX1001865 and pCART124 (arrow 3 and 2) at 0.37 µg/ml (lane 3).

Thus, overall FIG. 3 shows that a modifying the IdeZ sequence with the following modifications R70T, Y71del, N72Q, N73G, seen in both pCART202 and pCART203, increases the efficacy of cleavage of the 2nd IgG heavy chain as compared to pCART144 (IdeZ). Introducing in addition the L64_T65del modification also increases the efficacy of cleavage of the 1st heavy chain, seen for pCART203.

Figure 4:
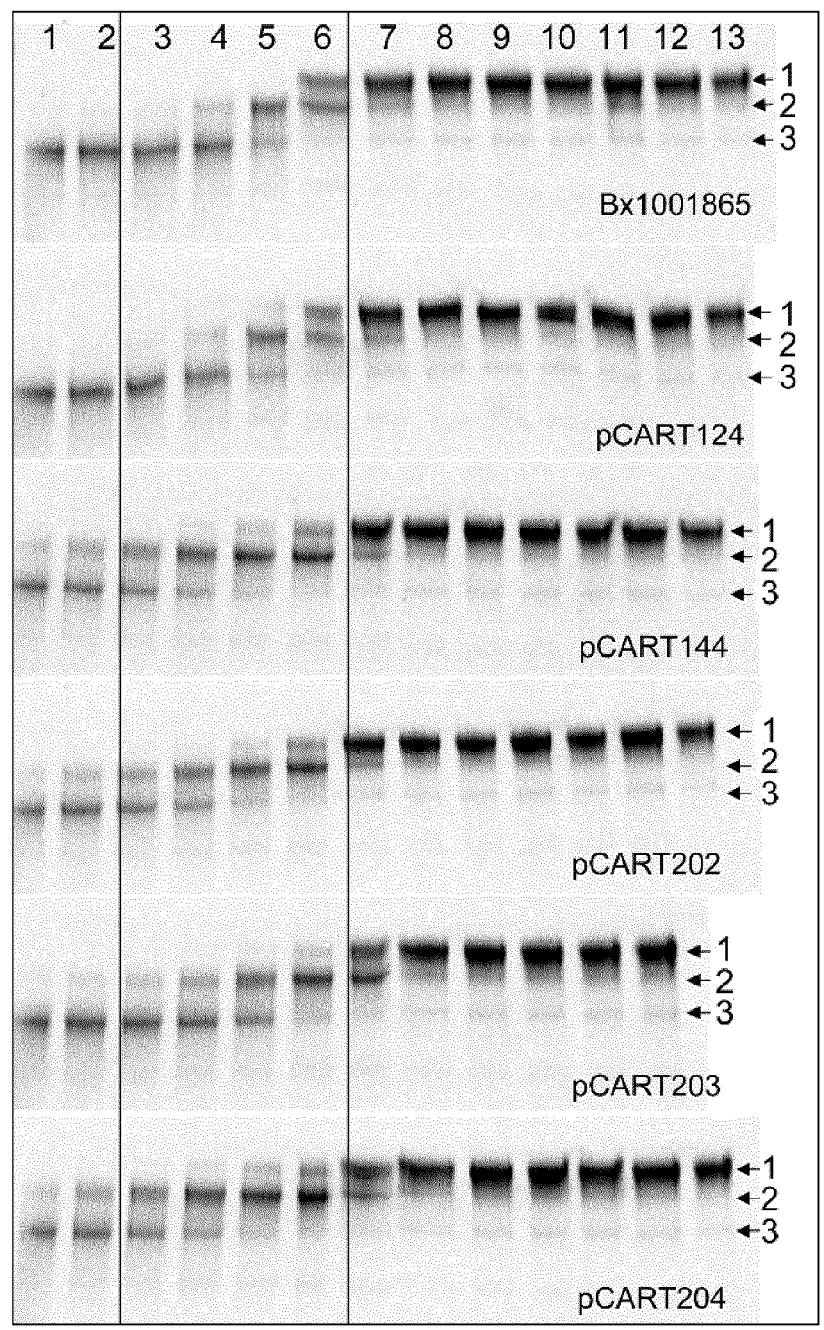
FIG. 4 shows the results of a representative SDS-PAGE gel used to visualize the cleavage products produced by incubation of IVIg with polypeptides of the invention or controls.

FIG. 4 shows the cleavage patterns produced with IVIg substrate for pCART202, 203 and 204 as compared to both IdeS controls (pCART124 and BX1001865) and IdeZ (pCART144). Enzyme concentrations go from 30 µg/ml (lane 1) down to 0.015 ng/ml (lane 12) in a 1:2 step dilution series. Intact IVIg (without enzyme) is shown in lane 13, with the exception of the image for pCART203, from which this lane is absent. The arrows on the right indicate the different cleavage products from IgG. Arrow 1: Intact IgG; arrow 2: scIgG (single cleaved IgG—results from cleavage of first IgG heavy chain); arrow 3: $F(ab')_2$ fragment (results from cleavage of second IgG heavy chain). Vertical lines were added to facilitate the comparison at the $1^{st}$ IgG heavy chain cleavage, where Intact IgG becomes scIgG (between lane 6 and 7) and at the $2^{nd}$ IgG heavy chain cleavage, where scIgG becomes $F(ab')_2$ fragment (between lane 2 and 3).

The enzyme pCART144 (IdeZ) shows more effective cleavage at the 1st IgG heavy chain (lane 6) compared to IdeS (BX1001865 and pCART124), resulting in a more intense scIgG band (arrow 2) and a weaker band of intact IgG (arrow 1). This is likely due to a lower level of binding by neutralizing anti-IdeS antibodies to pCART144 (IdeZ) compared to their recognition of IdeS. As seen for pCART202, pCART203 and pCART204 the increased efficacy in 1st heavy chain cleavage is true for all the IdeZ derived enzymes (lane 6). Concentrations of 0.94 ng/ml (lane 6) for pCART202, pCART203 and pCART204 result in an intense band of scIgG (arrow 2), with most of the IgG single cleaved, whereas the same concentration of IdeS results in less than 50% scIgG (lane 6).

However, pCART144 (IdeZ) is worse in cleavage of the 2nd heavy chain compared to IdeS (BX1001865 and pCART124). This results in a more intense scIgG band (arrow 2) from lane 5 (1.9 ng/ml of enzyme) and also in lanes 4 and 3, compared with IdeS for which the cleavage continues to F(ab')2 bands (arrow 3) already at the next titration step (lane 4, 3.75 µg/ml). Notably, pCART203 shows a capacity comparable to IdeS (BX1001865 and pCART124) at the 2nd cleavage site (lane 2, 3 and 4) and a higher cleavage efficacy than both IdeS and IdeZ (pCART144) at the 1st cleavage site (lane 7).

Enzyme pCART203 demonstrates IgG cleavage at 0.5 ng/ml (lane 7) and has generated mainly scIgG (arrow 2) at about 0.9 ng/ml (lane 6). This corresponds to a 2 fold increased efficacy compared to IdeS, which starts the cleavage at 0.9 ng/ml (lane 6) and has a dominating scIgG band at 1.9 ng/ml (lane 5). Overall FIG. 4 shows that modifying the IdeZ with the modifications L64_T65del, R70T, Y71del, N72Q and N73G increases the efficacy of cleavage of human IgG even in the presence of neutralizing ADA. This is clearly seen in pCART203 as compared to IdeS.

Figure 5:
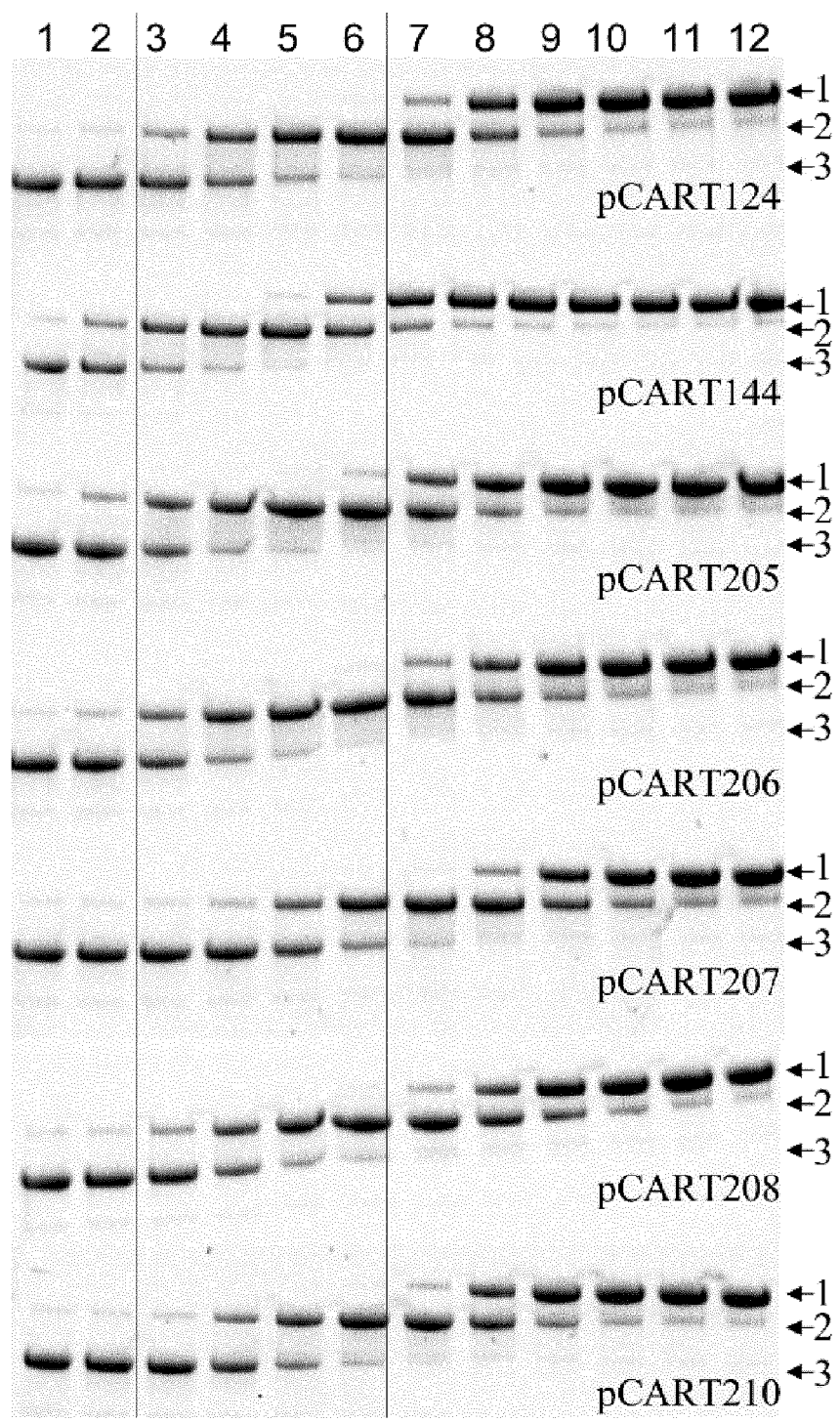
FIG. 5 shows the results of a representative SDS-PAGE gel used to visualize the cleavage products produced by incubation of IgG1 with further polypeptides of the invention or controls.

FIG. 5 shows the cleavage patterns produced with IgG1 substrate for pCART205, 206, 207, 208 and 210 as compared to both IdeS controls (pCART124 and BX1001865) and IdeZ (pCART144). Enzyme concentrations go from 3.33 µg/ml (lane 1) down to 0.02 ng/ml (lane 12) in a 1:3 step dilution series. The arrows on the right indicate the different cleavage products from IgG. Arrow 1: Intact IgG; arrow 2: scIgG (single cleaved IgG—results from cleavage of first IgG heavy chain); arrow 3: F(ab')$_2$ fragment (results from cleavage of second IgG heavy chain). Vertical lines were added to facilitate the comparison at the 1$^{st}$ IgG heavy chain cleavage, where Intact IgG becomes scIgG (between lane 6 and 7) and at the 2$^{nd}$ IgG heavy chain cleavage, where scIgG becomes F(ab')$_2$ fragment (between lane 2 and 3).

The enzyme pCART205 shows an increased capacity compared to pCART144 (IdeZ) in cleavage of both IgG heavy chains (lane 6 and 3), resulting in a more intense scIgG band (arrow 2, lane 6) and a very weak band of intact IgG (arrow 1, lane 6) and more intense F(ab')2 band (arrow 3, lane 3) compared to pCART144 (IdeZ) (lane 6 and 3). However, in the absence of neutralising ADA in this experiment (by contrast to that shown in FIG. 4), IdeS (pCART124) cleavage activity for pure IgG1 is higher than pCART205.

Polypeptides pCART207 and pCART210 both show increased IgG cleavage efficacy compared to both IdeS (pCART124) and IdeZ (pCART144) (lane 7 for 1st cleavage and lane 3 for 2nd cleavage). The most potent enzyme, pCART207, shows an approximate 3 fold increase of efficacy in cleavage of both IgG heavy chains compared to IdeS (pCART124). Complete conversion to scIgG (arrow 2) for pCART124 is obtained at 14 ng/ml (lane 6) whereas for pCART207 a single scIgG band (arrow 2) is seen already at 4.6 ng/ml (lane 7). A greater increase in efficacy for pCART207 as compared to pCART124 is seen in cleavage of the 2nd heavy chain. A more intense F(ab')2 band (arrow 3) is seen for pCART207 at 41 ng/ml (lane 4) than pCART124 shows at 0.37 µg/ml (lane 3).

pCART207 and pCART210 share the following modifications relative to the IdeZ sequence: L64_T65del, R70T, Y71del, N72Q, N73G, N138R. Thus overall FIG. 5 shows that these changes increase the efficacy of cleavage of human IgG1.

Figure 6:
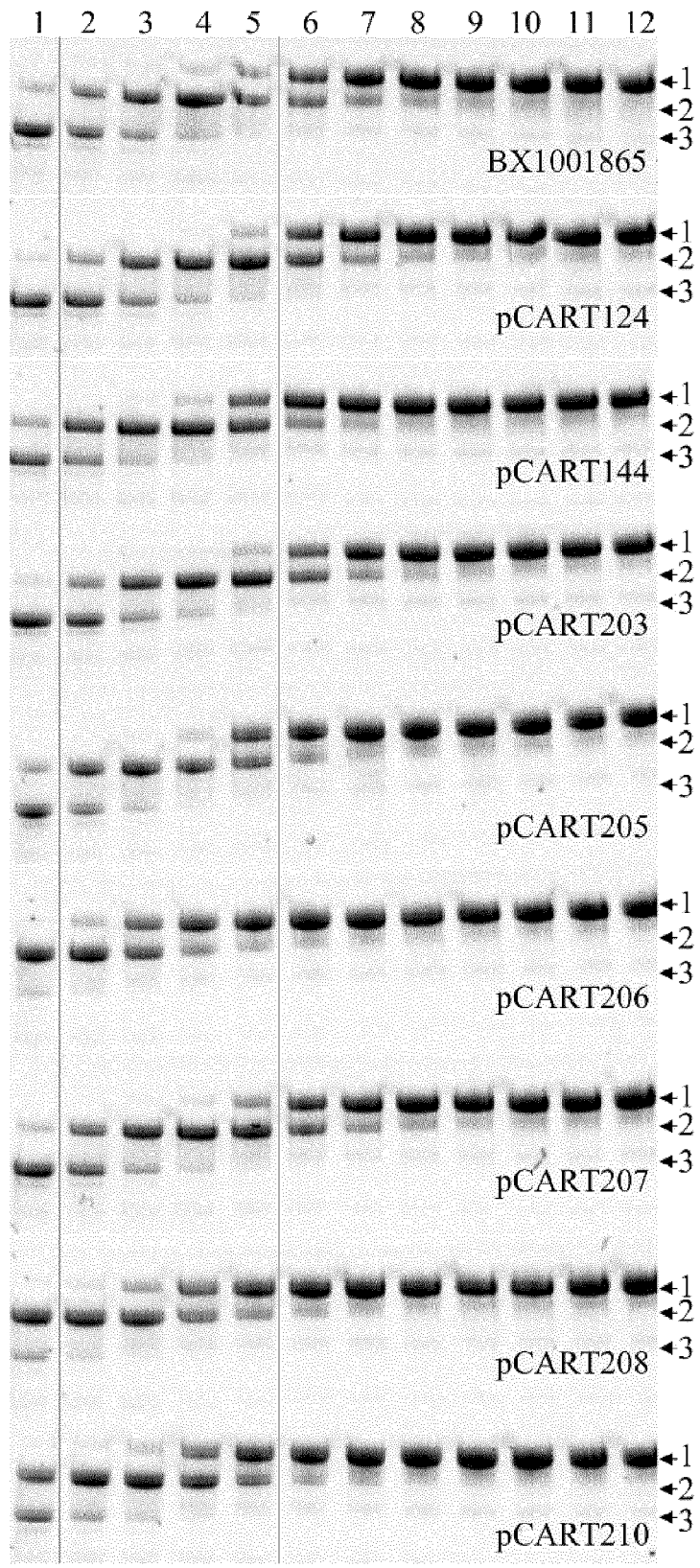
FIG. 6 shows the results of a representative SDS-PAGE gel used to visualize the cleavage products produced by incubation of IgG2 with polypeptides of the invention or controls.

FIG. 6 shows the cleavage patterns produced with IgG2 substrate for pCART203, 205, 206, 207, 208 and 210 as compared to both IdeS controls (pCART124 and BX1001865) and IdeZ (pCART144). Enzyme concentrations go from 3.33 µg/ml (lane 1) down to 0.02 ng/ml (lane 12) in a 1:3 step dilution series. The arrows on the right indicate the different cleavage products from IgG. Arrow 1: Intact IgG; arrow 2: scIgG (single cleaved IgG—results from cleavage of first IgG heavy chain); arrow 3: F(ab')2 fragment (results from cleavage of second IgG heavy chain). Vertical lines were added to facilitate the comparison at the 1$^{st}$ IgG heavy chain cleavage, where Intact IgG becomes scIgG (between lane 6 and 7) and at the 2$^{nd}$ IgG heavy chain cleavage, where scIgG becomes F(ab')2 fragment (between lane 2 and 3).

Enzymes pCART203 and pCART207 both show an approximate 3 fold increase in cleavage efficacy compared to pCART144 (IdeZ). pCART144 shows a single intense scIgG band (arrow 2) at a concentration of 0.12 pig/ml (lane 4), compared with a dominating scIgG band (arrow 2) for pCART203 and pCART207 at the lower concentration of 41 ng/ml (lane 5). pCART203 and pCART207 are comparable to IdeS (BX1001865 and pCART124) in efficacy of cleavage of both the 1$^{st}$ and 2$^{nd}$ IgG heavy chain (lane 6 and lane 2). However, in the absence of neutralising ADA in this experiment (by contrast to that shown in FIG. 4), IdeS (pCART124) cleavage activity is higher than each of pCART206, pCART208 and pCART210 for both heavy chains of pure IgG2. This can be seen from the single intense scIgG band (arrow 2) present even at the highest concentration of enzyme 3.3 µg/ml (lane 1) for pCART206 and pCART208. pCART205 derived from the IdeS/Z hybrid (pCART145) has about the same efficacy as IdeZ (pCART144) in cleavage of pure human IgG2 (lane 5 for 1$^{st}$ cleavage site and lane 2 for 2$^{nd}$ cleavage site), both resulting in a single scIgG band (arrow 2) at 0.12 µg/ml (lane 4) and a dominating F(ab')2 band at the highest concentration 3.3 µg/ml (lane 1).

Overall, FIG. 6 shows that the best modifications of IdeZ, i.e. which resulted in the highest increase of efficacy in cleaving IgG2, were those found in pCART203 and pCART207. These enzymes share the modifications L64_T65del, R70T, Y71del, N72Q, N73G, with pCART207 additionally possessing the N138R modification.

Figure 7:
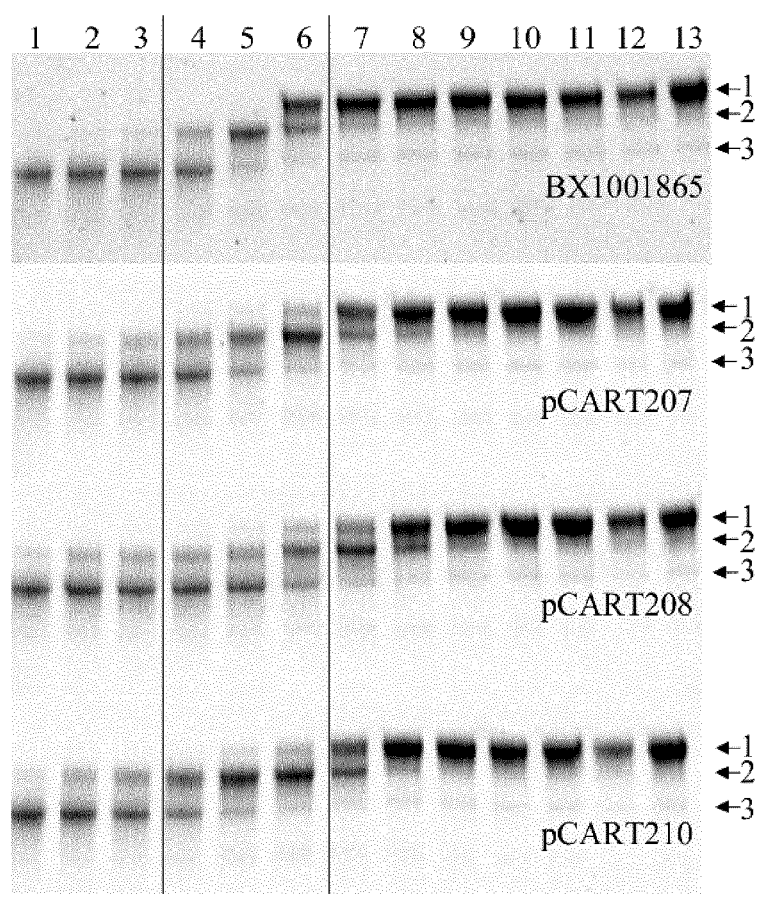
FIG. 7 shows the results of a representative SDS-PAGE gel used to visualize the cleavage products produced by incubation of IVIg with polypeptides of the invention or controls.

FIG. 7 shows the cleavage patterns produced with IVIg substrate for pCART207, 208 and 210 as compared to IdeS control (BX1001865). Enzyme concentrations go from 30 µg/ml (lane 1) down to 0.015 ng/ml (lane 12) in a 1:2 step dilution series. Intact IVIg (without enzyme) is shown in lane 13. The arrows on the right indicate the different cleavage products from IgG. Arrow 1: Intact IgG; arrow 2: scIgG (single cleaved IgG—results from cleavage of first IgG heavy chain); arrow 3: F(ab')2 fragment (results from cleavage of second IgG heavy chain). Vertical lines were added to facilitate the comparison at the 1$^{st}$ IgG heavy chain cleavage, where Intact IgG becomes scIgG (between lane 6 and 7) and at the 2$^{nd}$ IgG heavy chain cleavage, where scIgG becomes F(ab')$_2$ fragment (between lane 2 and 3).

pCART207, pCART208 and pCART210 all show increased efficacy compared to IdeS (BX1001865) in the cleavage of the 1$^{st}$ IgG heavy chain (lane 6). IdeS (BX1001865) has generated mainly scIgG (arrow 2) at a concentration of 1.9 ng/ml (lane 5). Similar results are obtained at 0.9 ng/ml (lane 6) for both pCART207 and pCART210, and at only 0.5 ng/ml (lane 7) for pCART208. In the case of pCART208 this is approximately a 4 fold increase in cleavage efficacy of the 1$^{st}$ heavy chain. In cleavage of the 2$^{nd}$ heavy chain pCART208 shows an improved cleavage efficacy, resulting in a dominating F(ab')2 band (arrow 3) at 1.9 ng/ml (lane 5), whereas IdeS (BX1001865) has only generated scIgG (arrow 2) at the same concentration.

Overall, FIG. 7 shows that pCART207, pCART208 and pCART210 have increased efficacy of cleavage of human IgG in the presence of anti-IdeS neutralizing antibodies (ADA), as compared to IdeS. A similar result was obtained for pCART206 (data not shown). pCART206, 207, 208 and 210 all share the following modifications relative to the IdeZ sequence: L64_T65del, R70T, Y71del, N72Q and N73G. In addition, pCART207, 208 and 210 also share the N138R modification. Thus, FIG. 7 also confirms that these different modifications increase the efficacy of cleavage of human IgG in the presence of neutralizing ADA.

Example 3—Assessment of Immunogenicity

Competitive Anti-IdeS Antibody Assay

This assay is based on competition between a test polypeptide and IdeS for binding to anti-IdeS antibody. A pre-incubation of test enzyme and IVIg will enable binding of anti-IdeS antibodies to the tested pCART enzyme. Thereafter the IVIg-enzyme-mix is added to an IdeS-coated plate and any anti-IdeS antibody not bound to test polypeptide will instead bind to the IdeS on the plate. All binding incubations was made in the presence of 2 mM iodoacetic acid (IHAc) to inhibit IgG cleavage and in high salt so that only high affinity binding occurs. After washing, a biotinylated goat anti-human F(ab')2-specific F(ab')2 fragment is used as detector. Poor recognition of test polypeptide by the anti-IdeS antibodies in IVIg will result in high binding of the anti-IdeS antibodies in IVIg to the plate, giving a high signal. Good recognition of test polypeptide by the anti-IdeS antibodies in IVIg will give the opposition result. The detailed protocol is as follows:

Reference IdeS (BX1001865) was coated overnight on multi-titre plates (5 µg/ml), then washed with PBS-T and blocked for 1 hour with 2% BSA in PBS supplemented with 2 mM IHAc and 1 M NaCl. A mixing plate was prepared with stepwise dilutions of test polypeptide and 20 µg/ml IVIg in PBS supplemented with 0.1% BSA, 2 mM IHAc and 1 M NaCl. The mixing plate was incubated for 1 hour at room temperature on a shaker. After incubation, the blocking solution was discarded from the IdeS-coated plate and 50 µl of each mixture from the mixing plate was transferred to the wells of the coated plate. After incubation for 1 hour room temperature on a shaker, the plate was washed with PBS-T and a detector, biotinylated goat anti-human F(ab')$_2$-specific F(ab')$_2$ fragment (20 000× diluted) was added. After incubation for 30 minutes the plate was washed and 40 000× diluted SA-HRP (Pierce) was added and incubated for 30 min. The plate was washed and developed using TMB One Component as a chromogenic substrate for HRP for 7 min, stopped with 0.5 M $H_2SO_4$. Absorbance (OD) was measured at λ=450 nm. The results were inverted (1/OD value) and presented as a ratio compared with pCART124 (1/(test polypeptide/pCART124)) for visualisation in bar diagrams.

Figure 8:
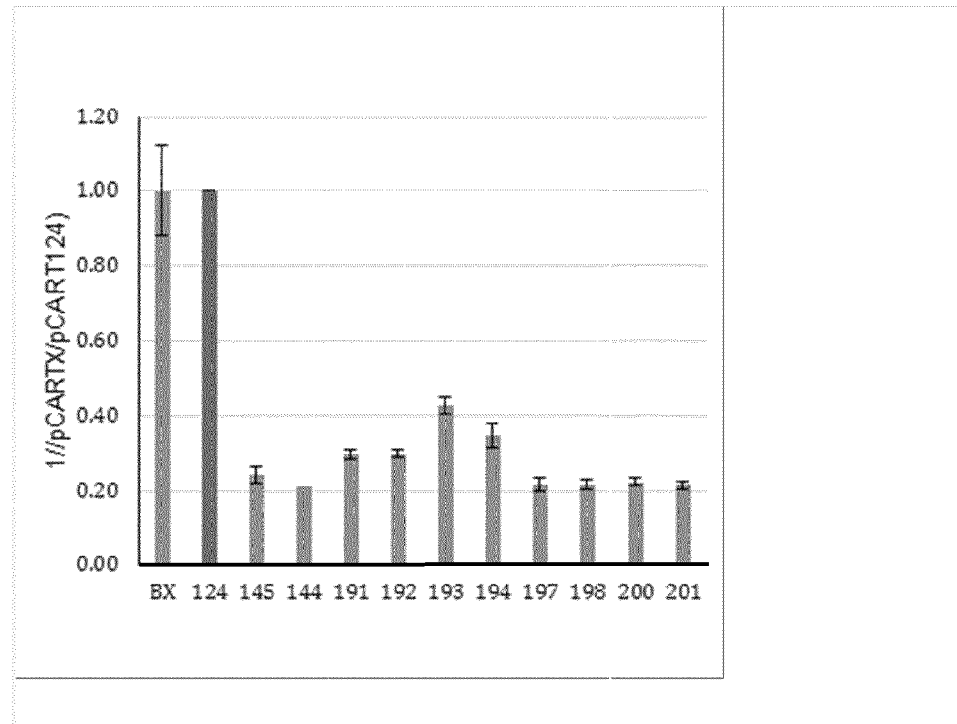
FIGS. 8 and 9 show the results of representative competition assays to determine the level of recognition of polypeptides of the invention by IdeS-specific antibodies, as compared to controls.
Figure 9:
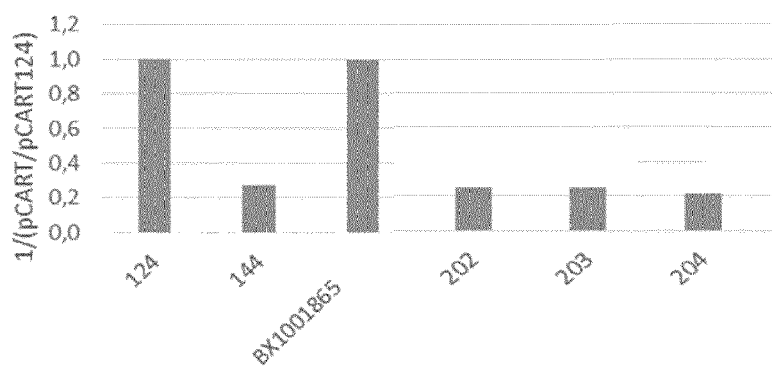

The results for pCART191, 192, 193, 194, 197, 198, 200 and 201 are shown in FIG. 8. The results for pCART202, 203 and 204 are shown in FIG. 9. All of the tested polypeptides show considerable reduction in anti-IdeS antibody recognition as compared to IdeS. The polypeptide showing the least reduction (pCART193) was recognised at a level approximately 60% lower than IdeS. The remaining tested polypeptides were 70 or even 80% lower than IdeS.

Anti-IdeS Titre Assay

This assay is based on comparing IVIg dilution titres. The different test polypeptide and control IdeS (BX10018865 and pCART124) were coated on micro titre plates. Binding of anti-IdeS antibodies to the test polypeptides or controls was evaluated by adding titrated amounts of IVIg (1:2 step dilution series from 40 to 0.625 µg/ml i.e. in titres corresponding to 1:250 down to 1:16000 diluted serum) to the plates. The dilution buffer is high salt concentration so that only high affinity binding occurs and includes 2 mM IHAc to inhibit IgG cleavage and in high salt so that only high affinity binding occurs. A cut off OD value was set in each experiment to approximately 3 times the blank. The documented result for each tested polypeptide was the dilution titre of IVIg that gave the lowest OD values (lowest binding of anti-IdeS antibody) above the cut off. In other words; less diluted IVIg is needed for polypeptides with low recognition by the anti-IdeS antibodies (ADA) and more diluted IVIg is needed for enzymes which are highly recognized by the ADA. In brief, the protocol was as follows:

Reference IdeS and each test enzyme was coated overnight on multi titre plates (2 µg/ml), washed with PBS-T and blocked for 1 hour with 2% BSA in PBS supplemented with 2 mM IHAc. The blocking solution was discarded from and 50 µl of stepwise dilutions of IVIg (dilution buffer: PBS IM NaCl+0.1% BSA+2 mM IHAc) was added and incubated for 1 hour at room temperature on a shaker. The plates were washed with PBS-T and a detector, biotinylated goat anti-human F(ab')2-specific F(ab')2 fragment (20 000× diluted) was added and incubated for 30 min. The plates were washed and 40 000× diluted SA-HRP (Pierce) was added and incubated for 30 min. The plate was washed and developed using TMB One Component as a chromogenic substrate for HRP for 7 min, stopped with 0.5 M $H_2SO_4$. Absorbance (OD) was measured at λ=450 nm.

Figure 10:
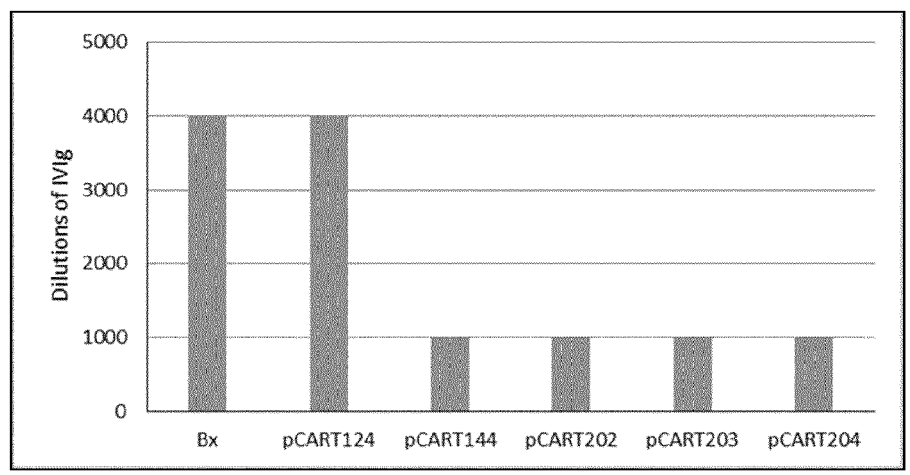
FIGS. 10 and 11 show the results of representative titration assays to determine the level of recognition of polypeptides of the invention by IdeS-specific antibodies, as compared to controls.

The results for pCART202, 203 and 204 are shown in FIG. 10. All three tested polypeptides scored 3× dilutions lower than IdeS for recognition by anti-IdeS antibodies.

Figure 11:
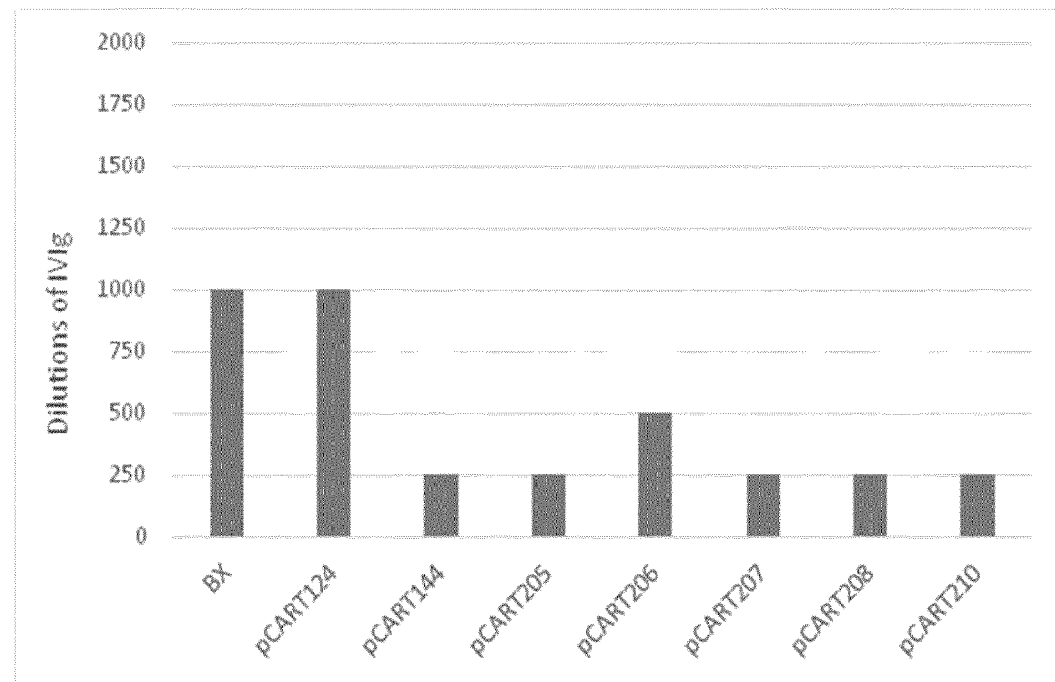

The results for pCART205, 206, 207, 208 and 210 are shown in FIG. 11. All except pCART206 scored 3× dilutions lower than IdeS for recognition by anti-IdeS antibodies. pCART206 scored 2× dilutions lower. Overall, the tested polypeptides are clearly less immunogenic than IdeS.

Summary

The tested polypeptides are generally more effective at cleaving human IgG than IdeZ and/or are at least as effective at cleaving human IgG as IdeS, and are also typically less immunogenic than IdeS.

Example 4—Assessment of Potency

Potency ELISA

Figure 18:
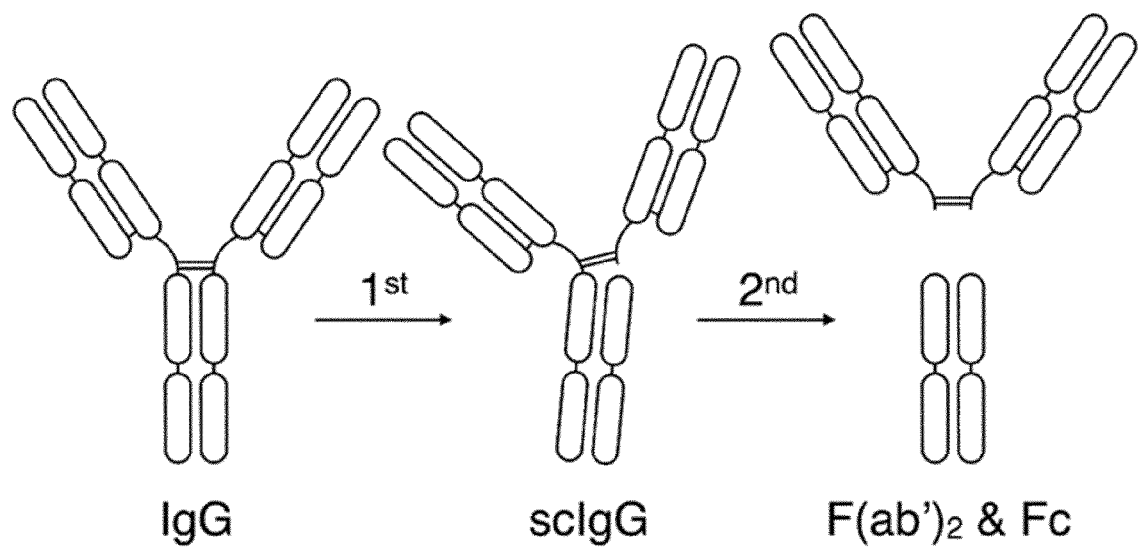
FIG. 18 Schematic representation of the cleavage of immunoglobulins by polypeptides of the invention.

To address the cleavage capacity of human IgG1 and IgG2, two ELISA-based potency assays were set up. One assay measuring IgG1 cleavage and the other IgG2 cleavage. EC50 (half maximal effective concentration) values were calculated for the different IgG cysteine protease polypeptides tested. The principle of the assays was to coat wells of a multi titre plate with a F(ab)$_2$-fragment directed to human IgG antibodies with specificity to the Fab region. Then titrated concentrations of IgG cysteine protease polypeptide (test or control) were incubated together with human IgG1 antibody (Humira) or human IgG2 antibody (XGEVA) in the wells. The quantity of intact or single cleaved human IgG (Humira or XGEVA) bound to the wells was measured using a detector antibody directed to human IgG with specificity against the Fc part of the antibody. The higher the concentration of a given IgG cysteine protease polypeptide in a well, the less intact human IgG antibody will be bound to the well, giving a lower signal. Similarly, a more potent IgG cysteine protease polypeptide will give a lower signal than a less potent IgG cysteine protease polypeptide when present at the same concentration. Titration dose-response curves were prepared for the IdeS control (pCART124) and all tested IgG cysteine protease polypeptides, in both the IgG1 (humira) and IgG2 (XGEVA) assay. EC50 values were also calculated for each tested variant, representing the concentration of a polypeptide where 50% of its maximal effect, in the second heavy chain cleavage of the IgG molecule, is observed i.e. the concentration where half of the IgG molecules are single cleaved and half are fully cleaved. A lower EC50 value represents a more effective IgG cysteine protease. The cleavage of the first IgG heavy chain, IgG to scIgG, is not visible in this assay because the Fc-part of the IgG is still present and can be detected by the Fc specific detector antibody (FIG. 18).

Brief summary of the laboratory protocol: Wells of multi titre plates were coated overnight (+2-8° C.) with Goat-anti-human Fab-specific F(ab)$_2$-fragment (0.5 pig/ml) (Jackson #109-006-097), then washed with PBS+0.05% Tween 20 (PBS-T) and blocked in 0.45% fish gelatin in PBS-T (block buffer) for 45-120 min at room temperature. Control IdeS (pCART124) and the IgG cysteine protease polypeptides to be tested were prepared as titration series in 1:4 dilution steps in block buffer with a starting concentration of 80

μg/ml. Equal volumes (25 μl) of human IgG1 (Humira) at a concentration of 0.5 μg/ml and the titrated amounts of IgG cysteine protease polypeptides were added to the wells and incubated 2 hours with shaking in a controlled temperature environment at 37° C. and then washed with PBS-T. Biotinylated mouse anti-human IgG Fc-specific (m-a-hIgG Bio II, Lot: C0013-ZC43C, Southern Biotech) (600 ng/ml) antibody was mixed with Strep-sulfo (200 ng/ml) and added to the multi titre plates. The plates were sealed with aluminum tape and incubated at +25° C. for 1 hour with shaking. The plates were then washed in PBS-T and 150 μl of 2× diluted Read buffer T (MSD read buffer T, Cat. no. R92TC-2) were added to each well. The plates were immediately read on a Plate reader, MSD (Meso Scale Discovery) QuickPlex SQ 120 Model 1300.

Efficacy assays visualised on gel: Assay conducted as described in Example 2 for cleavage of IgG1 (Humira), IgG2 (XGEVA) as well as cleavage of a pool of human IgG, IVIg (Octagam).

Results

Potency ELISA

Figure 12:
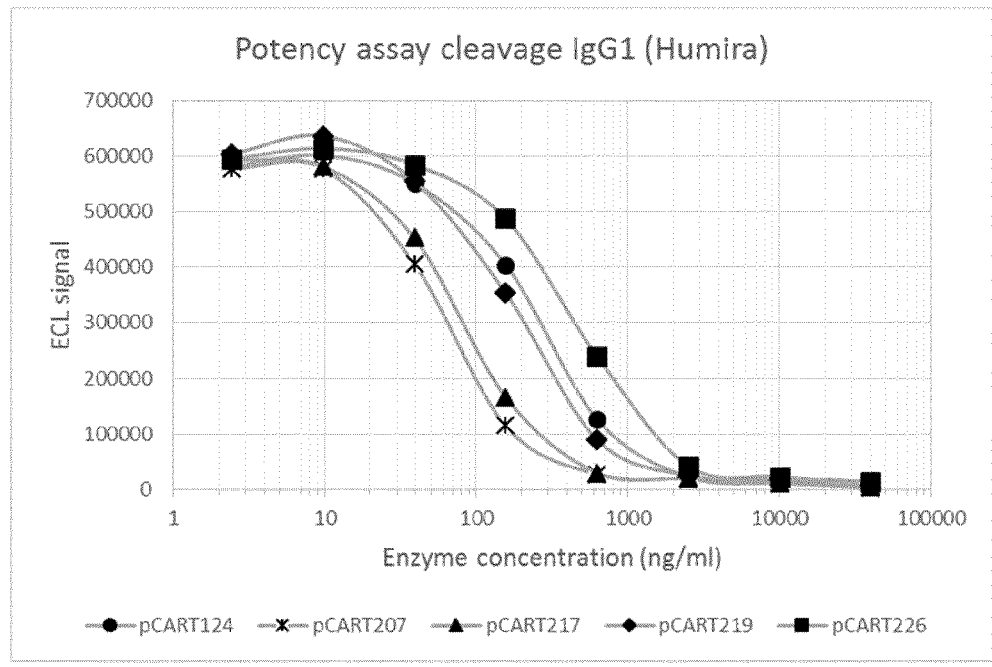
FIG. 12 shows representative titration curves for cleavage of IgG1 by different IgG cysteine protease polypeptides.
Figure 13:
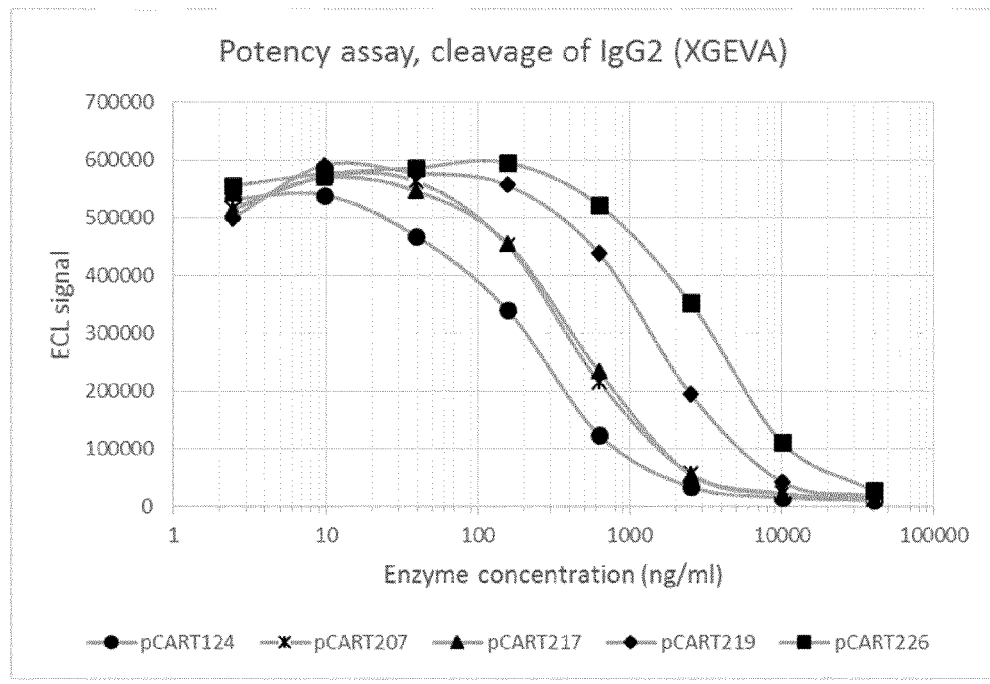
FIG. 13 shows representative titration curves for cleavage of IgG2 by different IgG cysteine protease polypeptides.

The resulting dose-response curves for the tested IgG cysteine proteases in the potency assays are shown in FIG. 12 (IgG1 cleavage) and FIG. 13 (IgG2 cleavage). pCART207, 217, 219 of the exemplary polypeptides of the invention tested here have improved potency (decreased EC50 values) in cleaving both heavy chains of IgG1 (FIG. 12) compared to the IdeS control pCART124 (table 1), with a fold improvement in potency of 1.4 for pCART219, 3.2 for pCART217 and as much as 4.0 for pCART207. pCART226 shows a somewhat lower potency than IdeS (pCART124) with a fold difference in EC50 of 0.6 (table 1). For cleavage of IgG2 (FIG. 13) all of the tested polypeptides show a lower potency compared to original IdeS (pCART124), with higher EC50 values (table 1) and a fold difference below 1, in cleavage of the second IgG heavy chain. However, all of the tested polypeptides are more potent than pCART144 (SEQ ID NO: 27) (data not shown) which is the sequence the IgG cysteine protease polypeptides of the invention are derived from.

Efficacy Assays Visualised on Gel

The cleavage of IgG1 (FIG. 14A) and IgG2 (FIG. 14B) visualised on gel clearly show the first and second heavy chain cleavage (the vertical lines in the figures mark the $1^{st}$ and $2^{nd}$ IgG heavy chain cleavage by BX1001865 and pCART124 cleavage). The * in the figures illustrate the approximate EC50 value i.e. the concentration where 50% of the IgG is single cleaved (scIgG) and 50% is fully cleaved (F(ab')$_2$). The data from the gels are summarised in table 2 (IgG cleavage) and table 3 (IgG2 cleavage). The cleavage of the $1^{st}$ heavy chain of IgG1 (Humira) is about the same, 1.5 ng/ml for IdeS (pCART124 and BX1001865), pCART207 and 217 but a somewhat higher concentration is needed to get a dominant scIgG band, about 4.6, for pCART219 and 226 (table 2). However, for the $2^{nd}$ heavy chain cleavage of IgG1 pCART207, 217 and 219 all demonstrate a higher efficacy than IdeS (pCART124 and BX1001864) (table 2), about 3× (one titration step) more effective in cleavage, about 370 ng/ml for IdeS and about 120 ng/ml for pCART207, 217 and 219. In cleavage of IgG2 (XGEVA) (FIG. 14B) pCART207, 217, 219 all show one titration step (1:3) lower efficacy and pCART226 has about two titration steps (1:6) lower efficacy compared to IdeS in the cleavage of both the $1^{st}$ and the $2^{nd}$ heavy chain (table 3). pCART229 shows about the same efficacy as IdeS (BX1001865 and pCART124) in cleavage of both the $1^{st}$ (4.6 ng/ml) and $2^{nd}$ (370 ng/ml) IgG heavy chain of IgG1 (Humira) (FIG. 15A and table 4), whereas cleavage of IgG2 (XGEVA) by pCART229 is about one titration step (1:3) less effective than IdeS in cleavage of both the $1^{st}$ and $2^{nd}$ IgG heavy chain (FIG. 15B and table 4).

Figure 16:
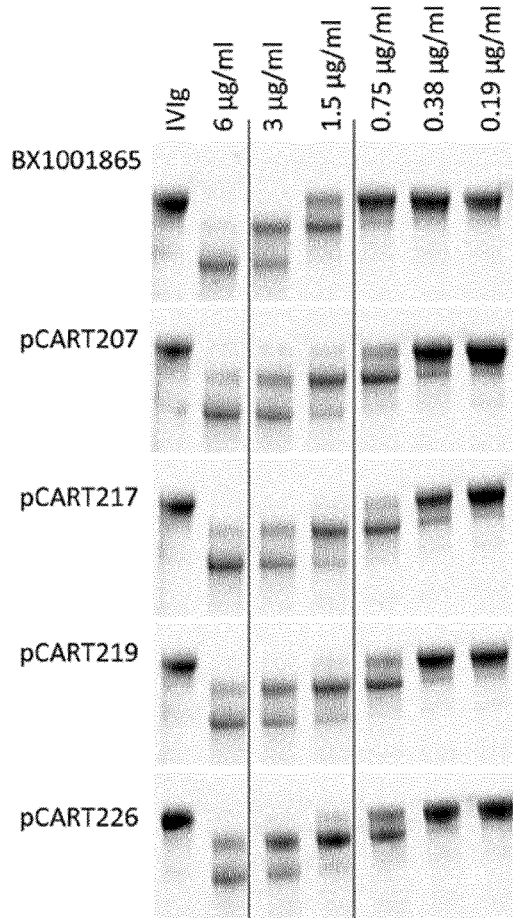
FIG. 16 shows the results of a representative SDS-PAGE used to visualize the cleavage products produced by incubation of IVIg with polypeptides of the invention or controls.

The IgG cysteine protease polypeptides pCART207, 217, 219 and 226 were also titrated in the human IgG pool, IVIg (Octagam) with IdeS (BX1001865) as control (FIG. 16). All of them showed a higher efficacy in cleavage of the $1^{st}$ IgG heavy chain of IVIg compared to IdeS. pCART207, 217, 219 and 226 all needed 0.75 μg/ml to achieve the $1^{st}$ cleavage whereas IdeS (BX1001865) needed 1.5 μg/ml to generate scIgG (FIG. 16 and table 5). In the $2^{nd}$ cleavage pCART207 and 217 are both more efficient than IdeS (BX1001865) with a concentration of 3 μg/ml to generate predominantly F(ab')$_2$ fragments and IdeS needs about 6 μg/ml (FIG. 16 and table 5). pCART219 and 226 are both less effective compared to IdeS in the second cleavage of the IgG pool IVIg. The cleavage of IVIg by pCART229 was analysed in a broader titration spectra with 1:2 dilutions from 30 μg/ml (FIG. 17) compared to the tested polypeptides in FIG. 16. The same efficacy is seen for IdeS (BX1001865 and pCART124) and pCART229 (FIG. 17) with a concentration of 1.9 μg/ml to generate scIgG and 7.5 μg/ml to give F(ab')2 fragments (table 6).

Summary of Figures for Example 4

FIG. 12. Titration curves for cleavage of IgG1 (Humira) by different IgG cysteine protease polypeptides.

FIG. 13. Titration curves for cleavage of IgG2 (XGEVA) by different IgG cysteine protease polypeptides.

Figure 14:
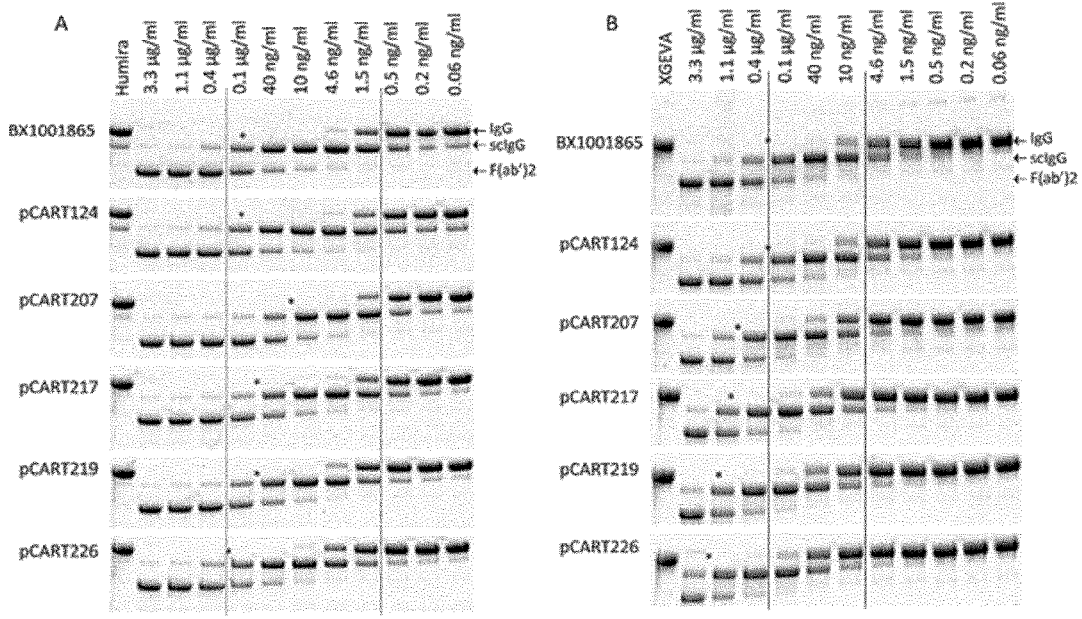
FIG. 14 shows the result of a representative SDS-PAGE used to visualize the cleavage products produced by incubation IgG with polypeptides of the invention or controls.

FIG. 14. IgG cleavage analyzed by SDS-PAGE using titrated (1:3 dilution from 3300 ng/ml) amounts of pCART207, 217, 219 and 226 with BX1001865 and pCART124 (original IdeS) as controls in the same cleavage experiment. A: cleavage of humira (IgG1) and B: cleavage of XGEVA (IgG2). Vertical lines mark the IdeS (BX1001865 and pCART124) concentrations needed to give the $1^{st}$ and $2^{nd}$ IgG heavy chain cleavage (where the amount of the cleaved product dominates over the uncleaved product). The * in the figures mark the approximate EC50 value in this experiment.

Figure 15:
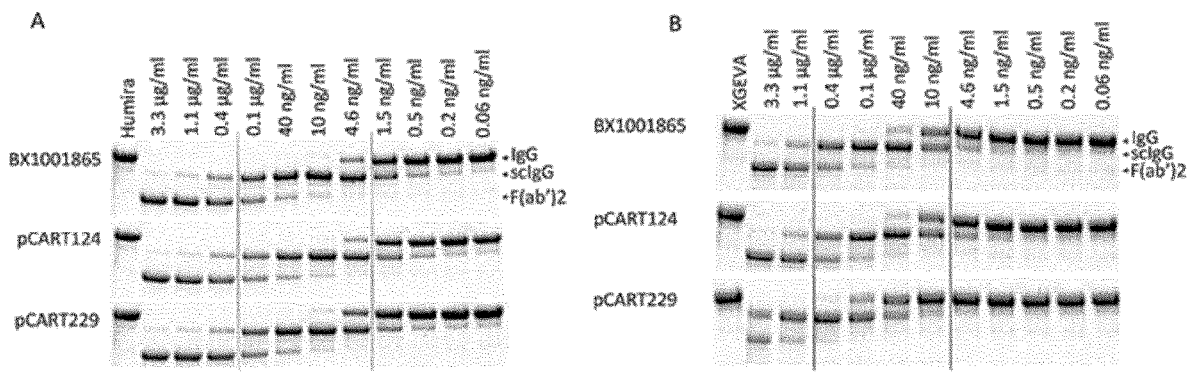
FIG. 15 shows the results of a representative SDS-PAGE used to visualize the cleavage products produced by incubation of IgG with polypeptides of the invention or controls.

FIG. 15. IgG cleavage analyzed by SDS-PAGE using titrated (1:3 dilution from 3300 ng/ml) amounts of pCART229 with BX1001865 and pCART124 (original IdeS) as controls in the same cleavage experiment. A: cleavage of humira (IgG1) and B: cleavage of XGEVA (IgG2). Vertical lines mark the IdeS (BX1001865 and pCART124) concentrations needed to give the $1^{st}$ and $2^{nd}$ IgG heavy chain cleavage (where the amount of the cleaved product dominates over the uncleaved product).

FIG. 16. IVIg cleavage analyzed by SDS-PAGE using titrated (1:2 dilution from 6 μg/ml) amounts of the tested IgG cysteine protease polypeptides and IdeS (BX1001865) as control in the same cleavage experiment.

Figure 17:
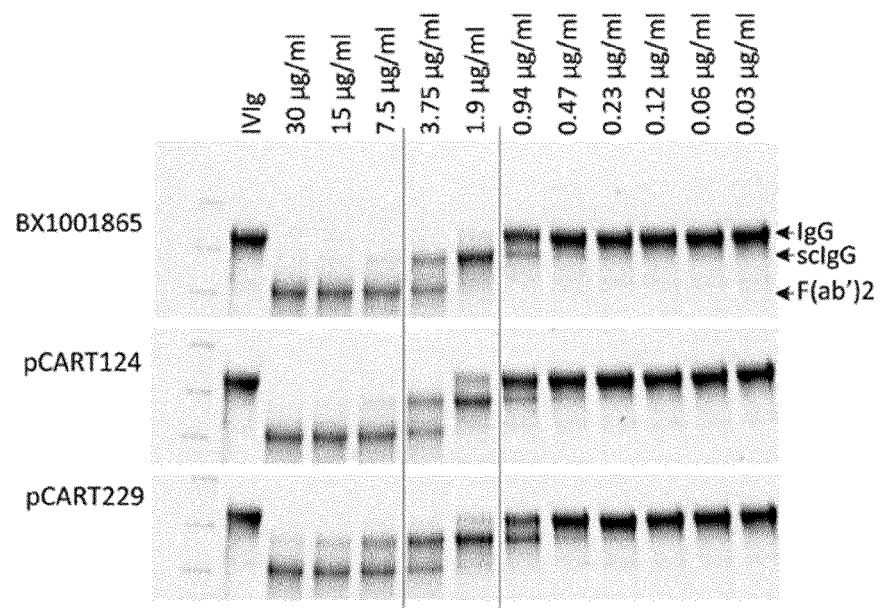
FIG. 17 shows the results of a representative SDS-PAGE used to visualize the cleavage products produced by incubation of IVIg with polypeptides of the invention or controls.

FIG. 17. IVIg cleavage analyzed by SDS-PAGE using titrated amounts (1:2 dilution from 30 μg/ml) of pCART229 with BX1001865 and pCART124 (original IdeS) as controls in the same cleavage experiment.

FIG. 18. Schematic representation of the cleavage of immunoglobulins by polypeptides of the invention. The enzymatic cleavage of the IgG is performed in two steps. First, one heavy chain of intact IgG is cleaved and single cleaved IgG (scIgG) is generated. Secondly, the next heavy chain is cleaved and the Fc-part is released. The Fc-part is still attached to the Fab-part in the scIgG molecule and since the detector antibody in the potency ELISA is recognizing the Fc-part of the IgG molecule the assay will not differentiate between complete IgG from scIgG.

Discussion and Conclusion

The lower EC50 values of pCART207, 217, 219 in the Humira potency ELISA demonstrate an improved potency in the $2^{nd}$ cleavage (from scIgG to F(ab')$_2$) of IgG1 compared to pCART124 (original IdeS). The somewhat lower activity of pCART226 in cleavage of IgG1 is shown in both the Humira potency ELISA and in the Humira efficacy assay analysed by SDS-PAGE.

It is demonstrated in the XGEVA potency ELISA that all of the tested polypeptides pCART207, 217, 219 and 226 have a lower potency compared to IdeS (pCART124) in cleavage of both IgG heavy chains of IgG2. However, when visualising the cleavage on gel instead it is clear that pCART207 has about the same activity as IdeS (BX1001865 and pCART124) in the $1^{st}$ IgG heavy chain cleavage, whereas it is about 3 times less effective (one titration step) in the $2^{nd}$ cleavage compared to IdeS. The same pattern is seen for pCART229 with a high efficacy in cleavage of IgG1, comparable to the activity of IdeS, but with a lower efficacy for cleavage of IgG2, primarily the cutting of the $2^{nd}$ IgG heavy chain. By analysing the IgG cleavage on gel the cutting of the $1^{st}$ heavy chain (from IgG to scIgG) becomes evident, this cleavage is invisible in the potency ELISA using an Fc-specific detector antibody. Most Fc-mediated actions of IgG are lost already in a single cleaved molecule (data not shown), which is central in a clinical situation where the main focus is to incapacitate pathogenic IgG molecules.

IVIg is a pool of human IgG containing approximately 65-70% IgG1, 35-30% IgG2 and IgG3/IgG4 sharing about 1%. Human IVIg also naturally contains anti-IdeS antibodies, from the IgG donor's earlier exposure to *S. pyogenes*, some of these antibodies will be neutralizing i.e. binding of these IdeS specific antibodies to IdeS will diminish or completely demolish the IdeS IgG protease activity. The results of IVIg cleavage by the different IgG cysteine protease polypeptides thereby display the overall cleavage of all four human IgG subclasses in about their normal ratio in human serum but also in the presence of the neutralizing anti-IdeS antibodies.

In general all IgG cysteine protease polypeptides tested have a lower efficacy in IgG2 cleavage compared to IgG1. pCART207, 217 and 219 are more efficient than IdeS in cleaving IgG1 but less efficient in cleaving primarily the $2^{nd}$ heavy chain of IgG2. The scIgG bands seen in FIG. 16 in the highest dose (6 µg/ml) of pCART207, 217, 219 and 226 and in FIG. 17 for pCART229 are most likely representing the IgG2 molecules in the IgG pool, IVIg (compare FIG. 14A with 14B and 15A with 15B).

TABLE 1

EC50 (ng/ml) measured by potency ELISA and fold difference in potency compared to original IdeS (pCART124).

|  | EC50 (ng/ml) in cleavage of IgG1 (Humira) | Fold improvement in potency | EC50 (ng/ml) in cleavage of IgG2 (XGEVA) | Fold improvement in potency |
| --- | --- | --- | --- | --- |
| pCART124 | 258 | 1 | 225 | 1 |
| pCART207 | 64 | 4.0 | 444 | 0.5 |
| pCART217 | 82 | 3.2 | 486 | 0.5 |
| pCART219 | 183 | 1.4 | 1508 | 0.15 |
| pCART226 | 433 | 0.6 | 3156 | 0.07 |

TABLE 2

Data for IgG1 (Humira) cleavage shown on gel (FIG. 14A). Concentration (ng/ml) of polypeptide needed to achieve $1^{st}$ and $2^{nd}$ IgG cleavage, where the cleaved product dominates in amounts over the uncleaved. Approximate EC50 value ((*) in FIG. 14A).

| ID | $1^{st}$ IgG heavy chain IgG to scIgG Conc. of enzyme (ng/ml) | $2^{nd}$ IgG heavy chain scIgG to F(ab')2 Conc. of enzyme (ng/ml) | Approximate EC50 value, i.e. equal amounts of scIgG and F(ab')2 (*) Conc. of enzyme (ng/ml) |
| --- | --- | --- | --- |
| BX1001865 | 1.5 | 370 | 100 |
| pCART124 | 1.5 | 370 | 100 |
| pCART207 | 1.5 | 120 | 10-40 |
| pCART217 | 1.5 | 120 | 40-100 |
| pCART219 | 4.5 | 120 | 40-100 |
| pCART226 | 4.5 | 370 | 100-400 |

TABLE 3

Data for IgG2 (XGEVA) cleavage shown on gel (FIG. 14B). Concentration (ng/ml) of polypeptide needed to achieve $1^{st}$ and $2^{nd}$ IgG cleavage, where the cleaved product dominates in amounts over the uncleaved. Approximate EC50 value ((*) in FIG. 14B).

| ID | $1^{st}$ IgG heavy chain IgG to scIgG Conc. of enzyme (ng/ml) | $2^{nd}$ IgG heavy chain scIgG to F(ab')2 Conc. of enzyme (ng/ml) | Approximate EC50 value, i.e. equal amounts of scIgG and F(ab')2 (*) Conc. of enzyme (ng/ml) |
| --- | --- | --- | --- |
| BX1001865 | 14 | 370 | 100-400 |
| pCART124 | 14 | 370 | 100-400 |
| pCART207 | 41 | 1100 | 400-1100 |
| pCART217 | 41 | 1100 | 400-1100 |
| PCART219 | 41 | 3300 | 1100 |
| pCART226 | 120 | 3300 | 1100-3300 |

TABLE 4

Data for IgG1 (Humira) cleavage and IgG2 (XGEVA) by pCART229 shown on gel (FIG. 15). Concentration (ng/ml) of polypeptide needed to achieve $1^{st}$ and $2^{nd}$ IgG cleavage (where the cleaved product dominates in amounts over the uncleaved).

| ID | $1^{st}$ IgG1 (Humira) heavy chain IgG to scIgG Conc. of enzyme (ng/ml) | $2^{nd}$ IgG1 (Humira) heavy chain scIgG to F(ab')2 Conc. of enzyme (ng/ml) | $1^{st}$ IgG2 (XGEVA) heavy chain IgG to scIgG Conc. of enzyme (ng/ml) | $2^{nd}$ IgG2 (XGEVA) heavy chain scIgG to F(ab')2 Conc. of enzyme (ng/ml) |
|---|---|---|---|---|
| BX1001865 | 4.6 | 370 | 14 | 1100 |
| pCART124 | 4.6 | 370 | 14 | 1100 |
| pCART229 | 4.6 | 370 | 122 | 3300 |

TABLE 5

Data for IVIg cleavage by pCART207, 217, 219 and 226 shown on gel (FIG. 16). Concentration (ng/ml) of polypeptide needed to achieve $1^{st}$ and $2^{nd}$ IgG cleavage, where the cleaved product dominates in amounts over the uncleaved.

| ID | $1^{st}$ IgG heavy chain IgG to scIgG Conc. of enzyme (ng/ml) | $2^{nd}$ IgG heavy chain scIgG to F(ab')2 Conc. of enzyme (ng/ml) |
|---|---|---|
| BX1001865 | 1500 | 6000 |
| pCART124 | 1500 | 6000 |
| pCART207 | 750 | 3000 |
| pCART217 | 750 | 3000 |
| PCART219 | 750 | 6000 |
| pCART226 | 750 | 6000 |

TABLE 6

Data for IVIg cleavage by pCART229 shown on gel (FIG. 17). Concentration (ng/ml) of polypeptide needed to achieve $1^{st}$ and $2^{nd}$ IgG cleavage, where the cleaved product dominates in amounts over the uncleaved.

| ID | $1^{st}$ IgG heavy chain IgG to scIgG Conc. of enzyme (ng/ml) | $2^{nd}$ IgG heavy chain scIgG to F(ab')2 Conc. of enzyme (ng/ml) |
|---|---|---|
| BX1001865 | 1900 | 7500 |
| pCART124 | 1900 | 7500 |
| pCART229 | 1900 | 7500 |

Example 5—ADA ELISA, a Competitive ELISA for ADA-IdeS Binding Sites

Anti-drug antibody (ADA) binding sites against IdeS was measured for "ADA" modified polypeptide of the invention (pCART207, 217, 219 and 226), using an ELISA, Meso Scale Discovery (MSD), based assay. The principle of the ELISA was to coat wells of a multi titre plate with original his-tagged-IdeS (pCART124). Most humans have antibodies against IdeS in their serum due to earlier infections of *S. pyogenes*. Here two different clinical human serum pools were used as standards for detection of ADA. The first pool is normal human serum from a serum pool of 100 individuals, called Human serum pool 1191807, and the second is a pool of serum from patients in the phase II study 13-HMe-dIdeS-02, called Phase II pool-2. These patients have been administered with IdeS once in a dose-range of 0.24-0.5 mg/Kg body weight and thereby have induced levels (approximately 50 times) of anti-IdeS ADA in their serum.

The outline of this competitive ADA ELISA is that IdeS (pCART124) is coated in the bottom of a micro titre plate. Human serum pools are pre-incubated together with the polypeptide to be tested for ADA recognition sites, or with the positive control IdeS (pCART124) in a molar ration of 1:100 with 100× excess of the tested polypeptide. The concentration of the two different serum pools used for pre-incubation is estimated from the standard curve to give approximately 80% binding to original IdeS. If the ADA binding sites have been abolished in the polypeptides tested, these polypeptides could not compete with the binding of ADA to the original IdeS at the bottom of the wells, i.e. a low signal demonstrates strong ADA-resemblance to the original IdeS (pCART124) and a high signal demonstrates weak ADA-resemblance to the original IdeS.

The concentration of both standards achieving approximately 80% binding at the linear section of the standard curve was about 200 ng ADA (IdeS)/ml. In the competitive pre-incubation this concentration of both standards were used separately and the concentration of the IgG cysteine protease polypeptides were used in a ratio of 100 times the ADA concentration, including the molar weight difference between an antibody of 150 kDa and IdeZ of approximately 35 kDa, 4.2 times, giving 100 times 200 ng/ml dividing with 4.2 giving approx. 5 µg/ml of the tested polypeptides. The standard serum containing 200 ng/ml ADA and the IdeS (pCART124) or tested polypeptides are pre-incubated together for 1 hour at room temperature (RT). As a control for maximum ADA binding, the same concentration of the standards were pre-incubated without IdeS (pCART124) or any other IgG cysteine proteases and used as 80% binding-max value. The lowest level of the standards curve, were used as lower limit values for the range of the calculation of the competition. The mean score for the standards pre-incubated with IdeS (pCART124) or the tested polypeptides were subtracted with the 80% standard binding value divided with 80% standard binding value subtracted with the lower limit values giving % competition value. The IgG cysteine protease polypeptide with the lowest % competition means that the most ADA binding epitopes have been abolished compared to original IdeS (pCART124).

Brief summary of the laboratory protocol: Wells of multi titre plates were coated overnight with pCART124 (1 µg/ml), washed 3 times with PBS-T and blocked for 1 hour with 0.45% fish skin gelatine and 2 mM of the cysteine protease inhibitor Iodoacetic acid (IHAc) in PBS.

Both standards were prepared as a titration series in 1:3 dilution steps in 0.45% fish skin gelatine and 2 mM IHAc in PBS, from 5000 ng ADA (IdeS)/ml to 2.5 ng ADA (IdeS)/ml to allow plotting of a standard calibration curve for the assay, with measurements at both the linear part and the maximum and minimum part of the standard curve. At the same time as the blocking of the plate, the standards and the IdeS (pCART124) or tested polypeptides were pre-incubated together for 1 hour at RT, i.e. the samples in a competition step, using 200 ng/ml ADA (standards) and 5 µg/ml IdeS control (pCART124) or IgG cysteine protease polypeptides to be tested.

The pCART124 coated plate was washed 3 times and then 50 µl pre-incubated samples or 50 µl standard were added to each well of the multi titre plate.

The plate was incubated at RT for 2 hours and then washed with PBS-T. Goat-anti-human F(ab) specific F(ab)$_2$ fragment-bio (Jackson #109-066-097, 0.65 mg/ml), (1000× diluted) was added as detector antibody and Streptavidin-Sulfo (MSD Cat. No: R32AD-1 or R32AD-5) (2000× diluted) in blocking buffer incubated for 1 hour at RT in the dark. The plate was washed 3 times and Read buffer T (MSD Read buffer T (4×) 4× diluted was added and the plate was analysed on a Plate reader, MSD (Meso Scale Discovery) QuickPlex SQ 120 Model 1300 directly.

Results and Discussion

Figure 19:
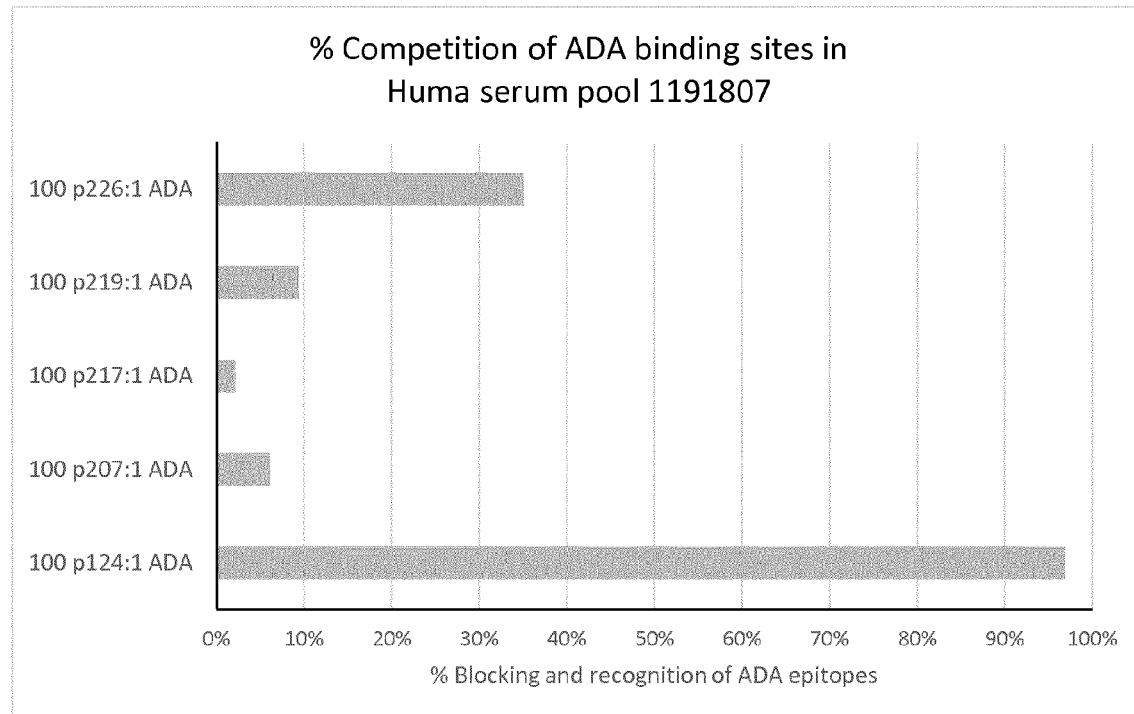
FIG. 19 shows the results of a representative % competition of ADA binding sites with polypeptides of the invention or controls.
Figure 20:
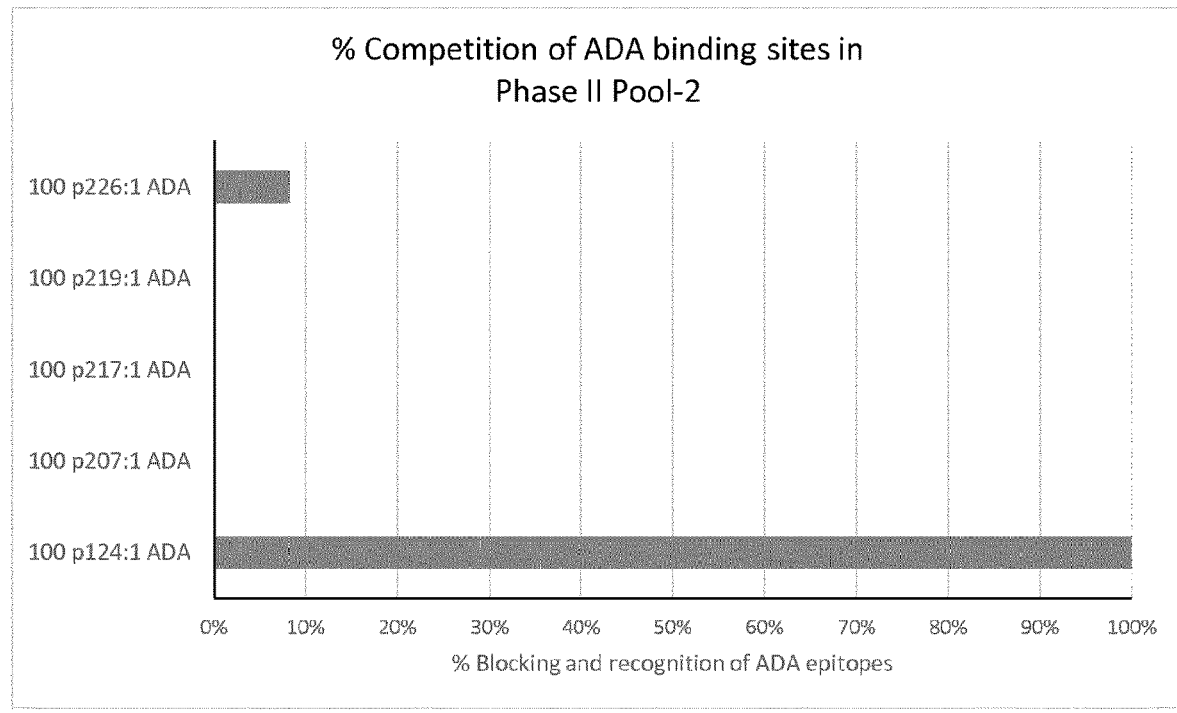
FIG. 20 shows the results of a further representative % competition of ADA binding sites with polypeptides of the invention or controls.

Percentage (%) blocking of IdeS-ADA binding sites for pCART207, 217, 219 and 226 are shown in FIG. 19 and FIG. 20 and the original IdeS pCART124 is used as positive control for 100% resemblance.

All tested IgG cysteine protease polypeptides, pCART207, 217, 219 and 226 occupy fewer ADA binding sites in human serum compared to original IdeS (pCART124). Patients that have been treated with IdeS once (Phase II pool-2) have developed more IdeS specific ADA and there were minimal recognition of pCART207, 217 and 219 (FIG. 20) compared to the serum pool from healthy volunteers (Human serum pool 1191807) (FIG. 19).

Example 6—Assessment of In Vivo Efficacy in an Octagam (Human IVIg) Mouse Model

In the present study BALB/c mice were injected intraperitoneally (i.p.) with human IVIg (Octagam). The concentration of human IVIg was administered at a dose of 900 mg/kg, to correlate to the human IgG plasma concentration (10 mg/ml).

Human IVIg was injected i.p. day 0. Twenty four hours (day 1) after the injection of human IVIg, PBS, IdeS controls (BX1001865 and pCART124), or the IgG proteases to be tested, pCART207, pCART217, pCART219 and pCART226, were administered intravenously (i.v.) at a dose of 1 mg/kg. Two hours later serum samples were collected and mice were sacrificed.

Efficacy ELISA

The principle of the assay was to coat wells of a multi titre plate with a F(ab')$_2$-fragment directed to human IgG antibodies with specificity to the Fab region. Then serum from mice treated with IVIg and IdeS controls (BX1001865 and pCART124) or the tested IgG cysteine protease polypeptide were added. The quantity of intact or single cleaved human IgG (IVIg) bound to the wells was measured using a detector antibody directed at human IgG (IVIg) with specificity against the Fc part of the antibody. The lower the detected concentration of intact human IgG antibody (IVIg) the more effective the IgG cysteine protease polypeptide is expected to be.

Brief summary of the laboratory protocol: Wells of a multi titre plate were coated overnight (+2-8° C.) with Goat-anti-human Fab-specific F(ab)$_2$-fragment (0.5 µg/ml) (Jackson #109-006-097), then washed with PBS+0.05% Tween 20 (PBS-T) and blocked in 2% BSA in PBS-T (block buffer) for 45-120 min at RT (room temperature). The Human Serum Protein Calibrator (DAKO #X0908) was used as a standard and added in a range from 0.5-300 ng/ml. The serum samples taken from mice treated with IVIg and different IgG cysteine protease polypeptides were thawed and diluted in block buffer 100 000 times before addition to the assay multi titre plate. The plate was incubated 2 hours with shaking at RT and then washed with PBS-T. Biotinylated mouse anti-human IgG Fc-specific (600 ng/ml) (Jackson #109-066-098) antibody was mixed with Strep-sulfo (200 ng/ml) (MSD #R32AD-1) and added to the multi titre plate. The plate was sealed with aluminum tape and incubated at RT for 1 hour with shaking. The plate was then washed in PBS-T and 150 µl of 2× diluted Read buffer T (MSD #R92TC-2) was added to each well. The plate was immediately analysed on a plate reader, MSD (Meso Scale Discovery) QuickPlex SQ 120 Model 1300 directly.

Efficacy Visualized on Gel

To visualize the human IgG cleavage in vivo in mouse 10 µl serum was diluted 1:10 in 90 µl PBS. Thereafter 10 µl diluted serum was mixed with 30 µl 4×SDS-PAGE loading buffer. 5 µl of IgG in-house marker was used to show the different IgG fragments (IgG, scIgG and F(ab')2). Samples were heated at 92° C. for 3 min (Thermo mixer compact, eppendorf) and briefly centrifuged before loading 10 µl on 4-20% Mini-Protean® TGX, Stain-Free™ gel (Cat. #456-8096, Biorad). Gels were run at 200 V for 40 min.

Results and Conclusion

In vivo cleavage of human IVIg (Octagam) by IdeS (BX1001865 and pCART124) and pCART207, 217, 219 and 226 were compared by studying the level of human IgG in serum by efficacy ELISA and by analysing the degradation of IgG by SDS-PAGE.

Figure 21:
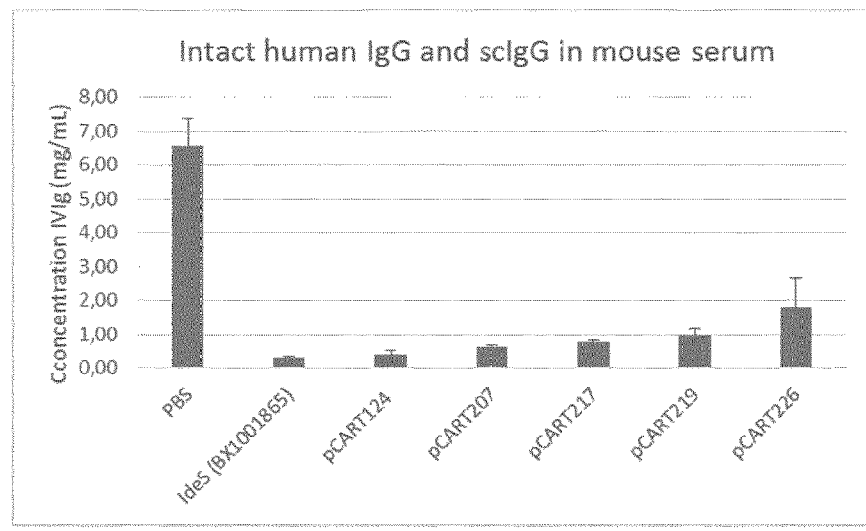
FIG. 21 shows the results of a representative efficacy ELISA used to determine the efficacy of the polypeptides of the invention in cleaving human IgG in vivo.

Treatment with IdeS (BX1001865 and pCART124) and the different IgG cysteine proteases pCART207, pCART217, pCART219 and pCART226 in IVIg-mice clearly demonstrated cleavage of human IgG in vivo in this mouse model (Table 7 and FIG. 21).

Figure 22:
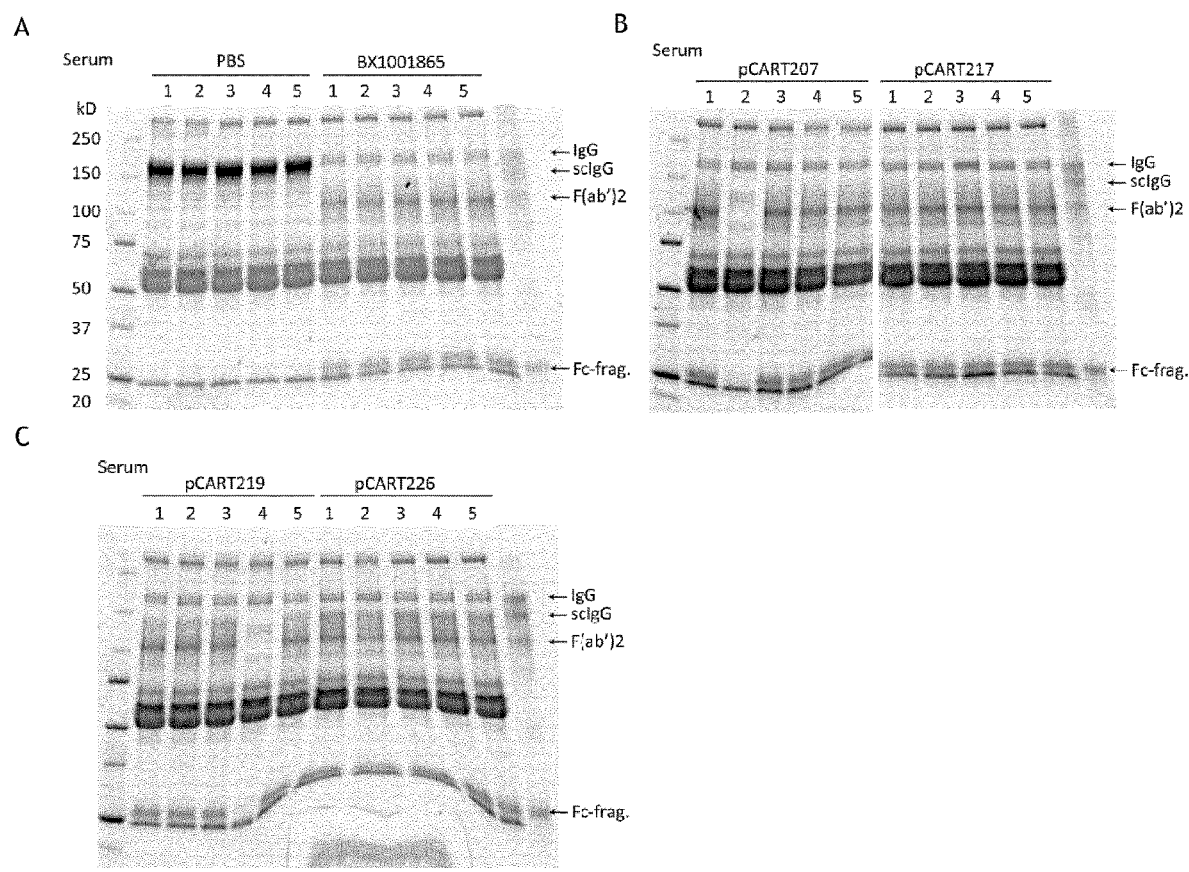
FIG. 22 shows the results of a representative SDS-PAGE used to visualize the IgG cleavage products produced in vivo by polypeptides of the invention.

Complete cleavage were shown for the IdeS control (BX1001865), pCART207 and pCART217, with no scIgG bands visible and significant F(ab')$_2$ bands on the gels (FIG. 22). pCART219 and pCART226 showed a lower efficacy in this mouse model with scIgG molecules still present in the mouse serum after two hours (FIG. 22C). However, no intact IVIg could be detected on the gel indicating that the higher concentration of IgG-Fc by the detector antibody (higher bar) for pCART219 and pCART226 in FIG. 21 comes from scIgG and not intact IgG. Mouse no: 2 in the pCART207 group and mouse no: 4 in the pCART219 group did not receive the IVIg injection (FIGS. 22B and C), therefor no IgG cleavage fragments were visible on the gel from these animals. The protein band patterns will represent the background proteins in BALB/c mouse serum. This shows that polypeptides of the invention cleave IgG in an in vivo model.

TABLE 7

Analysis of in vivo cleavage of human IgG in serum from mice treated with IdeS (BX1001865 and pCART124/the tested IgG cysteine proteases by the efficacy ELISA (average ± Stdev).

|  | Average (mg/mL) | Stdev |
|---|---|---|
| Control (PBS) | 6.58 | 0.80 |
| BX1001865 | 0.30 | 0.05 |
| pCART124 | 0.39 | 0.12 |
| pCART207 | 0.66 | 0.03 |
| pCART217 | 0.78 | 0.05 |
| pCART219 | 0.99 | 0.18 |
| pCART226 | 1.80 | 0.85 |

The invention claimed is:

1. A polypeptide having IgG cysteine protease activity and comprising a variant of the sequence of SEQ ID NO:4, which variant:
   (a) is at least 90% identical to SEQ ID NO: 4;
   (b) has a cysteine (C) at the position in said variant sequence which corresponds to position 102 of SEQ ID NO: 3;
   (c) has, at the positions in said variant sequence which correspond to positions 92, 272, 294 and 296 of SEQ ID NO: 3, a lysine (K), a histidine (H), an aspartic acid (D) and an aspartic acid (D), respectively; and
   (d) has deleted in its entirety the first twenty residues at the N terminus of SEQ ID NO: 4 (the contiguous sequence DDYQRNATEA YAKEVPHQIT);
   wherein said variant has cysteine protease activity and said polypeptide is more effective at cleaving human IgG1 than IdeZ; and
wherein said variant of the sequence of SEQ ID NO: 4:
   (1) has a positively charged amino acid at the position in said variant which corresponds to position 138 of SEQ ID NO: 3, optionally wherein said positively charged amino acid is arginine (R) or lysine (K);
   (2) has a positively charged amino acid at the position in said variant which corresponds to position 139 of SEQ ID NO: 3, optionally wherein said positively charged amino acid is arginine (R) or lysine (K); and/or
   (3) has at least one of the following modifications:
      i. a deletion of the leucine (L) and threonine (T) residues at the positions in said variant which correspond to positions 64 and 65 of SEQ ID NO: 3;
      ii. a threonine (T) in place of the arginine (R) at the position in said variant which corresponds to position 70 of SEQ ID NO: 3;
      iii. a deletion of the tyrosine (Y) at the position in said variant which corresponds to position 71 of SEQ ID NO: 3;
      iv. a glutamine (Q) in place of the asparagine (N) at the position in said variant which corresponds to position 72 of SEQ ID NO: 3;
      v. a glycine (G) in place of the asparagine (N) at the position in said variant which corresponds to position 73 of SEQ ID NO: 3;
      vi. an alanine (A) in place of the glutamic acid (E) at the position in said variant which corresponds to position 67 of SEQ ID NO: 3 and/or;
      vii. an asparagine (N) in place of the glutamine (Q) at the position in said variant which corresponds to position 68 of SEQ ID NO: 3.

2. The polypeptide according to claim 1, wherein said variant of the sequence of SEQ ID NO: 4 is at least 95% identical to SEQ ID NO: 4, respectively.

3. The polypeptide according to claim 1, which comprises or consists of the sequence of SEQ ID NO:9, optionally wherein said sequence includes an additional methionine at the N terminus and/or a histidine tag at the C terminus.

4. The polypeptide according claim 1, wherein said polypeptide is at least 2.0 fold more effective than IdeZ at cleaving human IgG, when measured in the same assay.

5. The polypeptide according to claim 1 which is less immunogenic than IdeS, wherein the immunogenicity of said polypeptide is no more than 85% of the immunogenicity of IdeS when measured in the same assay.

6. A composition comprising the polypeptide according to claim 1 and at least one pharmaceutically acceptable carrier or diluent.

7. The polypeptide according to claim 1, wherein said variant of the sequence of SEQ ID NO: 4 is at least 95% identical to SEQ ID NO: 17.

8. The polypeptide according to claim 1, wherein the variant of SEQ ID NO: 4 has deleted in its entirety the first twenty residues at the N terminus of SEQ ID NO: 4 (the contiguous sequence DDYQRNATEA YAKEVPHQIT) and sequence identity to SEQ ID NO: 4 is measured over residues 21-315.

9. The polypeptide according to claim 1, which comprises or consists of the sequence of SEQ ID NO: 17 or 19, optionally wherein said sequence includes an additional methionine at the N terminus and/or a histidine tag at the C terminus.

* * * * *